US006846638B2

(12) United States Patent
Shipwash

(10) Patent No.: US 6,846,638 B2
(45) Date of Patent: Jan. 25, 2005

(54) METHOD AND SYSTEM FOR RAPID BIOMOLECULAR RECOGNITION OF AMINO ACIDS AND PROTEIN SEQUENCING

(75) Inventor: Edward Shipwash, San Francisco, CA (US)

(73) Assignee: NanoBioDynamics, Inc., Berkeley, CA (US)

( * ) Notice: Subject to any disclaimer, the term of this patent is extended or adjusted under 35 U.S.C. 154(b) by 0 days.

(21) Appl. No.: 09/927,424

(22) Filed: Aug. 9, 2001

(65) Prior Publication Data

US 2002/0058273 A1 May 16, 2002

Related U.S. Application Data

(60) Provisional application No. 60/224,551, filed on Aug. 10, 2000.

(51) Int. Cl.[7] ............... G01N 33/53; G01N 33/566; G01N 33/567; C12M 1/34; C12M 3/00
(52) U.S. Cl. ............. 435/7.1; 435/287.1; 435/287.2; 436/501; 436/503; 436/63; 436/86; 436/172
(58) Field of Search ................... 435/7.1, 287.1, 435/287.2, 6, 7.2, 7.21, 70.1, 71.1, 24; 436/501, 503, 63, 86, 172

(56) References Cited

U.S. PATENT DOCUMENTS

| | | |
|---|---|---|
| 5,111,221 A | 5/1992 | Fare et al. |
| 5,183,740 A | 2/1993 | Ligler et al. |
| 5,225,374 A | 7/1993 | Fare et al. |
| 5,354,654 A | 10/1994 | Ligler et al. |
| 5,643,722 A | 7/1997 | Rothschild et al. |
| H1775 H | 1/1999 | Ligler et al. |
| 6,007,690 A | 12/1999 | Nelson et al. |
| 6,020,209 A | 2/2000 | Narang et al. |
| 6,100,541 A | 8/2000 | Nagle et al. |
| 6,103,199 A | 8/2000 | Bjornson et al. |
| 6,165,335 A | 12/2000 | Lennox et al. |
| 6,221,640 B1 * | 4/2001 | Tao et al. ............ 435/183 |

OTHER PUBLICATIONS

Berg. B. H., "Purification of Aminoacyl–tRNA Synthetase Kinase Activities Associated with Threonyl– and Tyrosyl–tRNA Synthetases Isolated from Bom:NMRI Mouse Liver", Bioch. Mol. Biol. Int., vol. 29, pp. 949–958 (1993).*

(List continued on next page.)

Primary Examiner—Jeffrey Fredman
Assistant Examiner—Teresa Strzelecka
(74) Attorney, Agent, or Firm—Townsend and Townsend and Crew LLP

(57) ABSTRACT

Methods, compositions, kits, and apparatus are provided wherein the aminoacyl-tRNA synthetase system is used to analyze amino acids. The method allows very small devices for quantitative or semi-quantitative analysis of the amino acids in samples or in sequential or complete proteolytic digestions. The methods can be readily applied to the detection and/or quantitation of one or more primary amino acids by using cognate aminoacyl-tRNA synthetase and cognate tRNA. The basis of the method is that each of the 20 synthetases and/or a tRNA specific for a different amino acid is separated spatially or differentially labeled. The reactions catalyzed by all 20 synthetases may be monitored simultaneously, or nearly simultaneously, or in parallel. Each separately positioned synthetase or tRNA will signal its cognate amino acid. The synthetase reactions can be monitored using continuous spectroscopic assays. Alternatively, since elongation factor Tu:GTP (EF-Tu:GTP) specifically binds all AA-tRNAs, the aminoacylation reactions catalyzed by the synthetases can be monitored using ligand assays. Microarrays and microsensors for amino acid analysis are provided. Additionally, amino acid analysis devices are integrated with protease digestions to produce miniaturized enzymatic sequenators capable of generating either N- or C-terminal sequence and composition data for a protein or peptide. The possibility of parallel processing of many samples in an automated manner is discussed.

62 Claims, 30 Drawing Sheets

OTHER PUBLICATIONS

Schmitt, A. P. et al., "Msn2p, a zinc finger DNA–binding protein, is the transcriptional activator of the multistress response in *Saccharomyces cerevisiae*", PNAS, vol. 93, pp. 5777–5782 (1996).*

Beaulande, M. et al., "Human cytosolic asparaginyl–tRNA synthetase: cDNA sequence, functional expression in *Escherichia co* and characterization as human autoantigen", Nucl. Acids Res., vol. 26, pp. 521–524 (1998).*

Shipwash. "Microarrays for Amino Acid Analysis and Protein Sequencing" Aug. 10, 1999, NanoNano Technology, vol. 1, pp. 1–21.*

VWR International "Molecular size exclusion chromatography", 2000, pp. 1–2.*

Demandolx, D "Guidelines for multifluorescence confocal imaging: acquisition, processing and display" 1997, Microscopy and Analysis, vol. 48, pp. 5–7.*

Schimmel, P., "Aminoacyl tRNA Synthetases: General Scheme of Structure–Function Relationships in the Polypeptides and Recognition of Transfer RNAs", *Annu. Rev. Biochem.*, 56:125–158 (1987).

Freist, W., "Mechanisms of Aminoacyl–tRNA Synthetases: A Critical Consideration of Recent Results", *Biochemistry*, 28:6787–6795 (1989).

Schimmel, P., "Aminoacylaton of RNA oligonucleotides: minimalist structures and origin of specificity", *FASEB J.*, 7:282–9 (1993).

Cusack, S., "Aminoacyl–tRNA synthetases", *Curr. Opin. Struc. Biol.*, 7:881–9 (1997).

Negrutskii et al., "Functional Interaction of Mammalian Valyl–tRNA Synthetase with Elongation Factor EF–1α in the Complex with EF–1H", *JBC*, 274:4545–4550 (1999).

Lloyd et al., "A broadly applicable continuous spectrophotometric assay for measuring aminoacyl–tRNA synthetase activity", *Nucl. Acids. Res.*, 23:2886–2892 (1995).

Reed et al., "Mechanisms of the Transfer of Aminoacyl–tRNA from Aminoacyl–tRNA Synthetase to the Elongation Factor 1α", *JBC*, 269:32932–36 (1994).

Lechler et al., "Overproduction of Phenylalanyl–tRNA Synthetase from *Thermus thermophilus* HB8 in *Escherichia coli*", *Protein Expr. Purif.*, 8:347–57 (1996).

Bausch et al., "Analysis and overexpression in *Escherichia coli* of a *staphylococcal* gene encoding seryl–tRNA synthetase", *Biochim. Biophys. Acta*, 1397:169–74 (1998).

Martinis et al., "Aminoacyl–tRNA synthetases: A new image for a classical family", *Biochimie*, 81:683–700.

Schimmel et al., "Aminoacyl tRNA synthetases as targets for new anti–infectives", *FASEB J.*, 12:1599–609 (1998).

DeGuzman et al., "Protein—RNA Recognition", *Biopolymers (Nucleic Acid Sciences)*, 48:181–95 (1998).

Freist et al., "Glutamyl–tRNA Synthetase", *Biol. Chem.*, 378:1313–29 (1997).

Freist et al., "Glycyl–tRNA Synthetase", *Biol. Chem.*, 377:343–56 (1996).

Cusak, S., "Eleven down and nine to go", *Nat. Struct. Biol.*, 2:824–31 (1995).

Fukai, S., "Structural Basis for Double–Sieve Discrimination of L–Valine from L–Isoleucine and L–Threonine by the Complex of tRNA$^{Val}$ and Valyl–tRNA Synthetase", *Cell*, 103:793–803 (2000).

Ibba et al., "Aminoacyl–tRNA Synthesis", *Ann Rev. Biochem. Sci.*, 69:617–50 (2000).

Ibba et al., "The Adaptor hypothesis revisited", *Trends Biochem.*, 25:311–6.

Freist et al., "Histidyl–tRNA Synthetase", *Biol. Chem.*, 380:623–46 (1999).

Cavarelli et al., "Recognition of tRNAs by aminoacyl–tRNA synthetases", *FASEB J.*, 7:79–86 (1993).

Webb, M.R., "A continuous spectrophotometric assay for inorganic phosphate and for measuring phosphate release kinetics in biological systems", *Proc. Nat'l Acad. Sci. USA*, 89:4884–4887 (1992).

Pellequer et al., "Measurement of kinetic binding constants of viral antibodies using a new biosensor technology", *J. Immunol. Meth.*, 166:133–143 (1993).

Blank et al., "Overexpression and Purification of *Thermus thermophilus* Elongation Factors G, Tu, and Ts from *Escherichia coli*", *Protein Expr. Purif.*, 6:637–45 (1995).

Moore et al., "Molecular Mimicry in Protein Synthesis?", *Science*, 270:1453–4 (1995).

Bilgin et al., "Solution Structure of the Ternary Complex between Aminoacyl–tRNA, Elongation Factor Tu, and Guanosine Triphosphate", *Biochemistry*, 37:8163–72 (1998).

Liljas, A.M., "Ribosomal proteins and elongation factors", *Curr. Opin. Struct. Biol.*, 5:721–7 (1995).

Negrutskii et al., "Eukaryotic Translation Elongation Factor 1α: Structure, Expression, Functions, and Possible Role in Aminoacyl–tRNA Channeling", *Prog. Nucleic Res. Mol. Biol.*, 60:47–78 (1998).

Krab et al., "EF–Tu, a GTPase odyssey", *Biochim Biophysics Acta*, 1443: 1–22 (1998).

Clark, J., "The ternary complex of EF–Tu and its role in protein biosynthesis", *Curr. Opin. Struct. Biol.*, 7:110–6 (1997).

Schmitt et al., "Molecular recognition governing the initiation of translation in *Escherichia coli*. A review", *Biochimie*, 78:543–54 (1996).

Cai et al., "Interaction of Mitochondrial Elongation Factor Tu with Aminoacyl–tRNA and Elongation Factor Ts", *J. Biol. Chem.*, 275:20308–14 (2000).

Nissan et al., "The crystal structure of Cys–tRNA$^{Cys}$–EF–Tu–GDPNP reveals general and specific features in the ternary complex and in tRNA", *Structure Fold Des.*, 7:143–56 (1999).

Liu et al., "F–actin Sequesters Elongation Factor 1α from Interaction with Aminoacyl–tRNA in a pH–dependent Reaction", *J. Cell. Biol.*, 135:953–63 (1996).

Reshetnikova et al., "Crystals of Intact Elongation Factor Tu from *Thermus themophilus* Diffracting to High Resolution", *J. Mol. Biol.*, 221:375–7 (1991).

Wagner et al., "Interaction of Guanosine Nucleotides and Their Analogs with Elongation Factor Tu from *Thermus thermophilus*", 34:12535–12542 (1995).

Nissen et al., "Crystal Structure of the Ternary Complex of Phe–tRNA$^{Phe}$, EF–Tu, and a GTP Analog", *Science*, 270:1464–1472 (1995).

Janiak et al., "Fluorescence Characterization of the Interaction of Various Transfer RNA Species with Elongation Factor Tu–GTP: Evidence for a New Functional Role for Elongation Factor Tu in Protein Biosynthesis", *Biochemistry*, 29:4268–4277 (1990).

Zubritsky, E., "Microplate Fluorometers Reach Critical Mass", *Anal. Chem.*, 71:39A–43A (1999).

Robeiro et al., "Purification of Aminoacyl–tRNA by Affinity Chromatography on Immobilized *Thermus thermophilus* EF–Tu–GTP", *Anal. Biochem.*, 228:330–335 (1995).

Nie et al., "Optical Detection of Single Molecules", *Ann. Rev. Biophys. Biomol. Struct.*, 26:567–596 (1997).

Wu et al., "A Continuous Spectrophotometric Assay for the Aminoacylation of Transfer RNA by Alanyl–Transfer RNA Synthetase", *Anal. Biochem.*, 211:320–323 (1993).

Oliver, I.T., "Spectrophotometric Method for the Determination of Creatine Phosphokinase and Myokinase", *Biochem. J*, 61:116–122 (1955).

Light, A., "Leucine Aminopeptidase (LAP)", *Meth. Enzymol.*, 11:426–436 (1967).

Breddam et al., "Determination of C–Terminal Sequences by Digestion With Serine Carboxypeptidases: The Influence of Enzyme Specificity", *Carlsberg Res. Comm.*, 52:55–63 (1987).

Roger, G., "Immobolized Derivatives of Leucine Aminopeptidase and Aminopeptidase M", *J. Biol. Chem.*, 248:1807–1812 (1973).

Martin et al., "Use of Carboxypeptidase Y for Carboxy—Terminal Sequence Determination in Proteins", *Carlsberg Res. Comm.*, 42:99–102 (1977).

Klarskov et al., "C–Terminal Sequence Determination of Peptides Degraded with Carboxypeptidases of Different Specificities and Analyzed by 252–Cf Plasma Desorption Mass Spectrometry", *Anal. Biochem.*, 180:28–37 (1989).

Thiede et al., "MALDI–MS for C–terminal sequence determination of peptides and proteins degraded by carboxypeptidase Y and P", *FEBS Letts*, 357:65–9 (1995).

Bonetto et al., "C–Terminal Sequence Analysis of Peptides and Proteins Using Carboxypeptidases and Mass Spectrometry after Derivatization of Lys and Cys Residues", *Anal. Chem.*, 69:1315–1319 (1997).

Chinali, G., "Isolation of tRNA isoacceptors by affinity chromatography with immobilized elongation factor Tu from *Escherichia coli*", *J. Biochem. Biophys. Meth.*, 34:1–10 (1997).

Giovane et al., "Interaction studies between elongation factor Tu and anthraniloyl–fluorescent analogues of guanyl nucleotides", *Eur. J. Biochem.*, 227:428–432 (1995).

Eccleston et al., "Interaction of a Fluorescent Analogue of GDP with Elongation Factor Tu: Steady–State and Time–Resolved Fluorescence Studies", *Biochemistry*, 26:3902–3907 (1987).

Iwane et al., "Single molecular assay of individual ATP turnover by a myosin–GFP fusion protein expressed in vitro", *FEBS Letts.*, 407:235 (1997).

Patterson, D.M., "C–Terminal Ladder Sequencing via Matrix–Assisted Laser Desorption Mass Spectrometry Coupled with Carboxypeptidase Y Time–Dependent and Concentration–Dependent Digestions", *Anal. Chem.*, 87:3971–3978 (1995).

Johnson et al., "Distance Moved by Transfer RNA During Translocation from the A Site to the P Site on the Ribosome", *J. Mol. Biol.*, 156:113–140 (1982).

Watson et al., "Macromolecular Arrangement in the Aminoacyl–tRNA–Elongation Factor Tu–GTP Ternary Complex. A Fluorescence Energy Transfer Study", *Biochemistry*, 34:7904–7912 (1995).

Dreher et al., "Quantitative Assessment of EF1α•GTP Binding to Aminoacyl–tRNAs, Aminoacyl–viral RNA, and tRNA Shows Close Correspondence to the RNA Binding Properties of EF–Tu", *JBC*, 274:666–72 (1999).

Nyrén et al., "Inorganic Pyrophosphatase–Based Detection Systems", *Analytical Biochemistry*, 220:46–52 (1994).

Ekins, "Ligand assays: from electrophoresis to miniaturized microarrays", *Clinical Chemistry*, 44:2015–2030 (1998).

Huang et al., "Determination of L–phenylalanine based on an NADH–detecting biosensor," *Anal. Chem.*, 70:991–7 (1998).

Lee et al., "Application of a flow injection fibre optic biosensor for the analysis of different amino acids", *Biosens Bioelectron*, 9:29–32 (1994).

Campanella et al., "Analysis of L–dopa in pharmaceutical preparations and of total phenols content in urine by means of an enzyme–amperometric sensor", *J Pharm Biomed Anal*, 11:1099–104 (1993).

Thoma et al., "Automated phenylthiocarbamyl amino acid analysis of carboxypeptidase/aminopeptidase digests and acid hydrolysates", *Journal of Chromatography*, 537:153–165 (1991).

Nyrén et al., "Inorganic Pyrophosphatase–Based Detection Systems", *Analytical Biochemistry*, 220:39–45 (1994).

Nyrén et al., "Enzymatic Method for Continuous Monitoring of Inorganic Pyrophosphate Synthesis", *Analytical Biochemistry*, 151:504–509 (1985).

Forrest et al., "Aminoalkyl Adenylate and Aminoacyl Sulfamate Intermediate Analogues Differing Greatly in Affinity for their Cognate *Staphylococcus aureus* Aminoacyl tRNA Synthetases", *Bioorganic & Medicinal Chemistry Letters*, 10:1871–1874 (2000).

Ribeiro et al., "Purification of Aminoacyl–tRNA by Affinity Chromatography on Immobilized *Thermus thermophilus* EF–Tu–GTP", *Analysis Biochemistry*, 228:330–335 (1995).

Bilgin et al., "Solution Structure of the Ternary Complex between Aminoacyl–tRNA, Elongation Factor Tu, and Guanosine Triphosphate", *Biochemistry*, 37:8163–8172 (1998).

Ohlson et al., "Use of monoclonal antibodies for weak affinity chromatography", *Journal of Chromatography A*, 758:199–208 (1997).

Dunn et al., "Quantitative Affinity Chromatography. Determination of Binding Constants by Elution with Competitive Inhibitors", *Proc. Nat. Acad. Sci. USA*, 71:2382–2385 (1974).

Winzor, "Recent developments in quantitative affinity chromatography", *Journal of Chromatography*, 597:67–82 (1992).

Rabbany et al., "Assessment of Heterogeneity in Antibody—Antigen Displacement Reactions", *Anal. Chem.*, 69:175–182 (1997).

Narang et al., "Multianalyte Detection Using a Capillary–Based Flow Immunosensor", *Analytical Biochemistry*, 255:13–19 (1998).

Remy et al., "Purification of Yeast Phenylalanyl–tRNA Synthetase by Affinity Chromatography, on a tRNA$^{Phe}$––Sepharose Column", *FEBS Letters*, 27:134–138 (1972).

Louie et al., "Affinity Purification of Aminoacyl–tRNA", *Analytical Biochemistry*, 141:402–408 (1984).

Chang et al., "Continuous Spectrophotometric Assay for Aminoacyl–tRNA Synthetases", *Analytical Biochemistry*, 142:369–372 (1984).

Shipwash, Edward, "Microarrays for Amino Acid Analysis and Protein Sequencing", *Physics*, Abstract physiscs/9908021.

\* cited by examiner

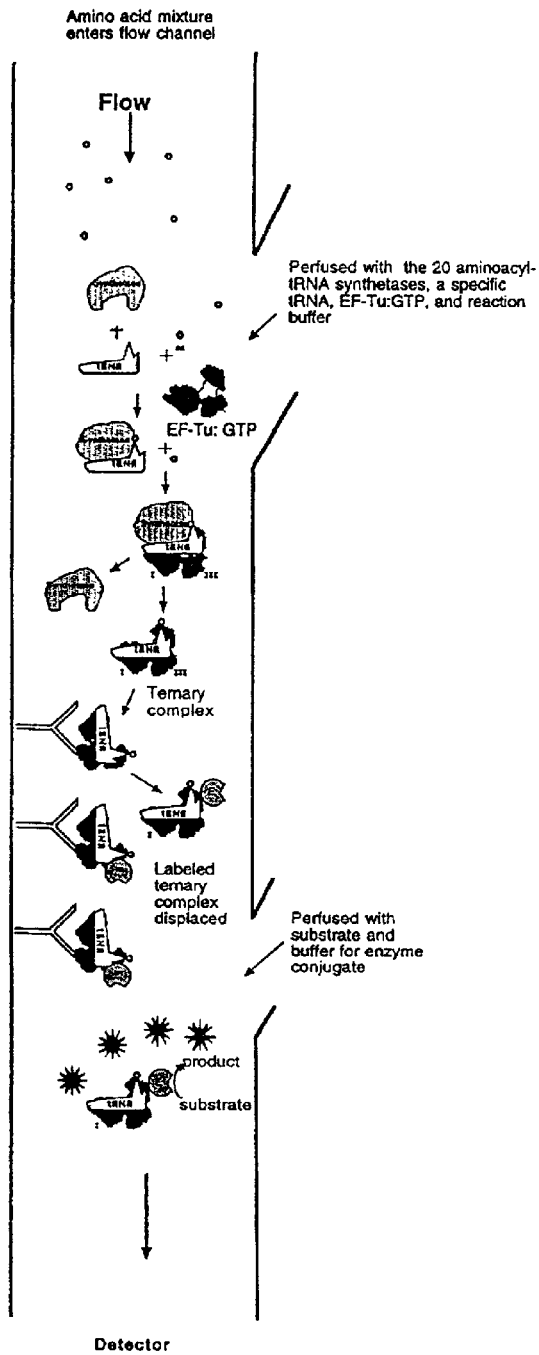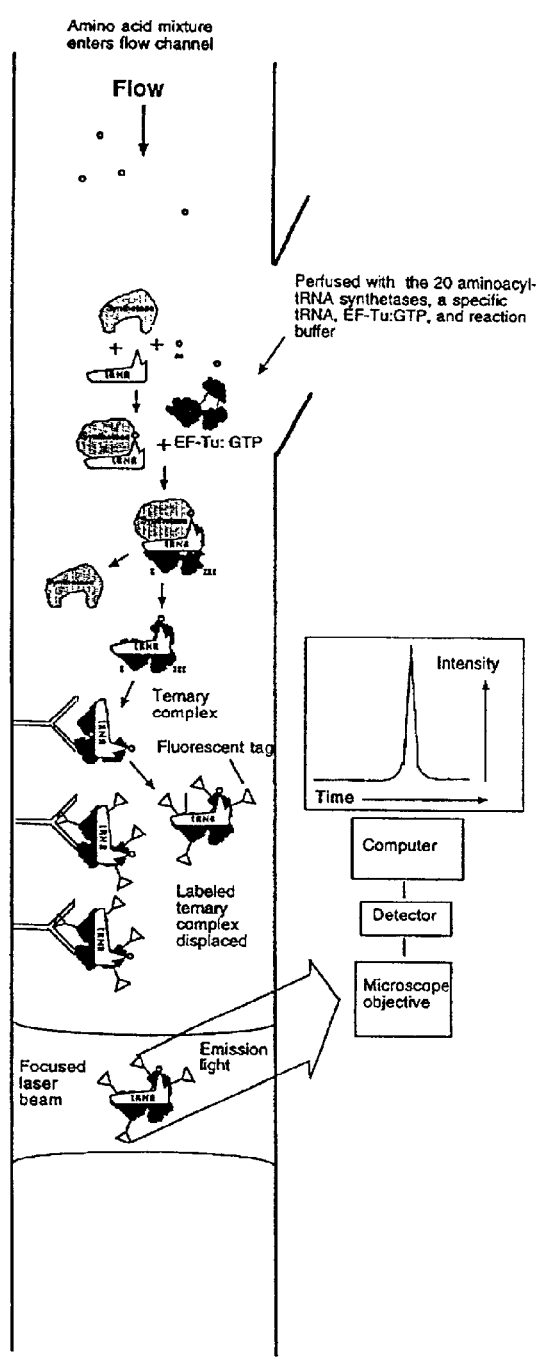
FIG. 7A
FIG. 7B

Biosensors

Using biosensor technology the biospecifically eluted substance may be detected by a change in signal at the transducers surface resulting form the displacement. The following examples illustrate this embodiment of the inventioin. Any of the biosensor technologies may be employed in these embodiments of the invention. Suitable biosensors include but are not limited to surface plasmon biosensors, optical fibers, electrochemical biosensors, and piezoelectric biosensors.

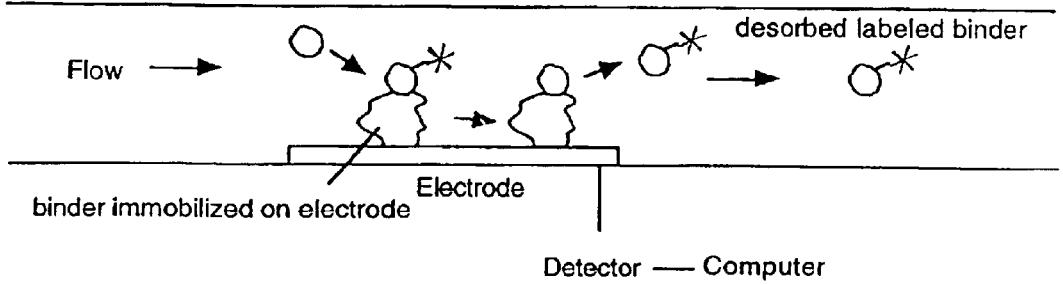

In this embodiment of the invention, the dicrease in signal at the electrode surface is proportional to the eluted labeled molecule.

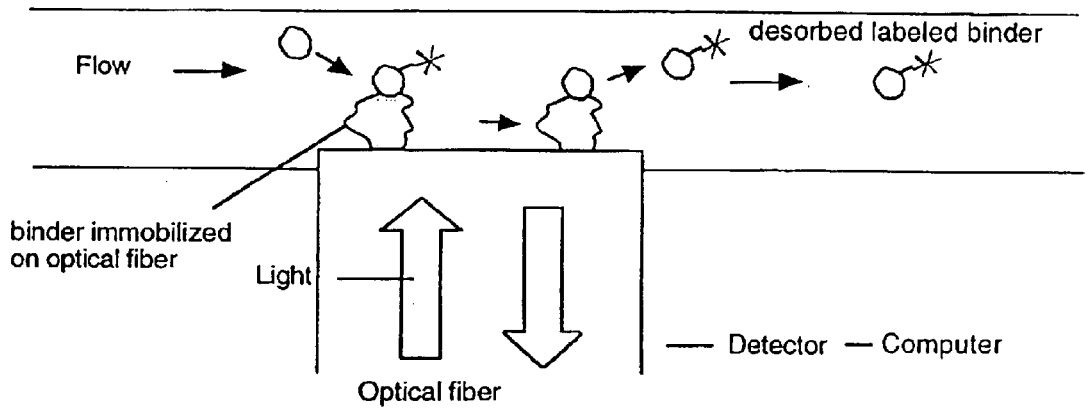

In this embodiment of the current invention, the decrease in signal at the surface of an optical fiber or optical waveguide bearing the substance having a reversibly bound labeled molecule is proportional to the eluted labeled molecule.

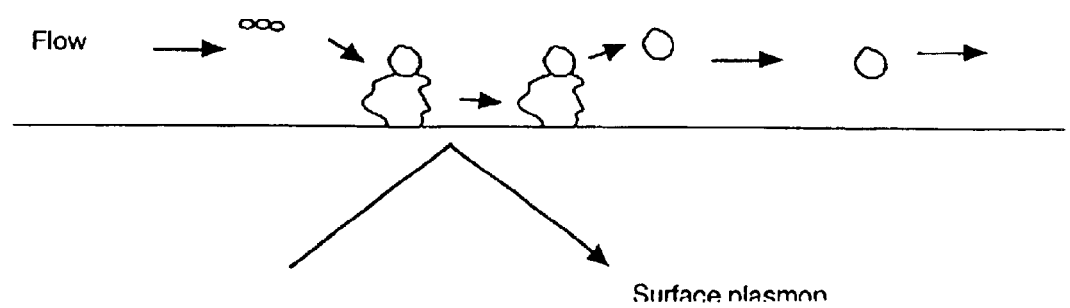

FIG. 24

METHOD AND SYSTEM FOR RAPID BIOMOLECULAR RECOGNITION OF AMINO ACIDS AND PROTEIN SEQUENCING

CROSS-REFERENCES TO RELATED APPLICATIONS

This application claims priority under 35 U.S.C. § 119(e) of U.S. Patent Application No. 60/224,551 filed on Aug. 10, 2000 which is incorporated herein by reference.

FIELD OF THE INVENTION

This invention relates to devices and methods for rapid biomolecular recognition based detection of amino acids in a sample; and, more particularly, to the application of biomolecular recognition techniques to rapid analysis of protein amino acid composition and amino acid sequences in protein.

BACKGROUND

Amino acids are among the most important biochemical substances in nature. Of particular interest are the 20 natural or primary protein amino acids, which are alanine, cysteine, aspartic acid, glutamic acid, phenylalanine, glycine, histidine, isoleucine, lysine, leucine, methionine, asparagine, proline, glutamine, arginine, serine, threonine, valine, tryptophan, and tyrosine. In addition to being the building blocks of all proteins, the 20 natural amino acids play important roles in metabolism Thus, amino acid analysis is of broad interest, having applications in virtually every aspect of biochemical research, biotechnology (agriculture, medicine), clinical medicine, food technology and large-scale proteome projects. Amino acid analysis is applied to a vast range of samples of differing complexity, including simple purified peptides and proteins in analytical biochemistry and pharmacology; complex biological samples from plants, animals, and microbes; body fluids in clinical chemistry; human and animal foods and nutritional supplements. In addition, amino acid analysis is crucial to protein chemistry and is used for routine quality control and screening of biological samples.

Research in protein chemistry is dependent upon the analysis of amino acids. Amino acid analysis is used not only to identify a protein, but is the only reliable method for determining the molar concentration of a protein. For example, amino acid analysis may be used to determine the protein-protein interaction ratios in various complexes. When coupled with exopeptidase digestions, amino acid analysis can be used for protein end group (N-terminal and C-terminal) amino acid compositional and amino acid sequence analysis. Such protein end group amino acid analysis can be used to identify proteins and provide important information about the primary structure of proteins. It is especially important to determine the N- and C-terminal sequence "tag" (short N- or C-terminal amino acid sequence) of intact proteins. This information is used to verify the start and stop point of a protein or gene, and is important in allowing PCR cloning of a complete gene, as well as identifying limited proteolysis.

In large-scale proteome projects, where the aim is to characterize all proteins expressed by the genome, there is great interest in amino acid analysis for the purpose of protein identification and characterization. For example, amino acid analysis is used to identify proteins separated by two-dimensional polyacrylamide gel electrophoresis where thousands of proteins are separated in a single experiment.

Further, with the ever-increasing use of proteins as therapeutics, amino acid analysis finds wide applications in drug research and development. In the pharmaceutical industry, amino acid analysis is used to quantitate a protein or peptide of interest including drugs intended for human use, in quality control testing of protein based drugs, and in protein identification and analysis.

Amino acid analysis is also routinely used in quality control analysis of amino acid containing products including proteins, peptides, pharmaceuticals, industrial enzymes, nutritional supplements and foods where amino acids are both important nutrients and indicators of protein composition. In clinical medicine, amino acid analysis is used to detect metabolic disorders. For example, amino acid analysis is used in the detection of phenylketonuria (PKU) in newborns and in following the metabolic state and dietary compliance of PKU patients.

Accordingly, there is a high demand for rapid, sensitive, and inexpensive methods for amino acid analysis. Unfortunately, current methods for amino acid analysis and protein end group analysis remain labor-intensive, slow, complicated, inaccurate, and insensitive. Historically, the determination of amino acids in protein hydrolysates and other samples has proven to be a difficult problem. The current art employs chromatography methods to separate the amino acids. Various chromatographic and electrophoretic techniques have been developed to resolve amino acids, including gas chromatography, reverse-phase chromatography with precolumn derivatization with various reagents, and ion exchange chromatography with postcolumn derivatization and capillary electrophoresis. These methods are complicated because the 20 primary amino acids do not differ from one another in any systematic way that is conducive to this analysis. Therefore, the separation of these 20 components is difficult. The task is further complicated by the similar structures and properties of many of the amino acids such as leucine, isoleucine, serine, and threonine, or tyrosine and phenylalanine. This method of analysis is further hindered by the sample composition. Samples are often a complex mixture of different substances such as proteins, carbohydrates, lipids, etc. The presence of these compounds interferes with the analysis, since they may bind to the stationary phase during chromatography, thereby limiting the capacity or blocking the column. In addition, most amino acids lack a strong chromophore for detection; hence amino acids need to be derivatized for detection. All of this translates into slow, tedious, expensive and inaccurate analysis.

The classical amino acid analyzers employ ion exchange chromatography to separate the amino acids followed by postcolumn reaction with ninhydrin. These complicated instruments, still in common use, are relatively insensitive (commonly nanomole detection, with lower limits of 200 to 500 picomoles of amino acids), slow, expensive and require an inordinate amount of time and effort to process a single sample. An additional complication is the relative instability of the ninhydrin reagent. "Within-run" and "between-run" precisions are often poor for an automated instrument. Additionally, these systems require relatively large amounts of sample for analysis. For example, they can require as much as 1 microgram of protein. This requirement can be problematic in analyzing very small amounts of sample material.

The current art for amino acid analysis and protein end group analysis also presents major obstacles for the production of protein and polypeptide based products, bioresearch, and proteome projects. Viability of techniques for amino acid analysis are driven increasingly by the needs for greater sensitivity, higher throughput, and lower costs. The more important amino acid identification becomes the more the inadequate the existing methodology In short, the prior art techniques do not provide the rapid precise analysis required in today's environment, given the increased importance and demand for amino acid analysis. Therefore, a new approach to amino acid analysis is needed that is simple, rapid, sensitive, inexpensive and easy to use. Furthermore, methods and systems are needed that are suitable for miniaturization and multiplexing for the analysis of multiple samples in parallel. In addition, a need exists for real-time amino acid analyzers that can monitor amino acids in situ or in process control situations where samples are run periodically and results are desired quickly. Amino acids have important roles in metabolism and it is desirable to be able to analyze amino acids in vivo and in situ (e.g., in organisms and cell cultures)

At the molecular level, essentially all biological functions are mediated through the selective binding of ligands and receptors. In the past few decades, devices and systems applying "biomolecular recognition" phenomena for the analysis of samples used in diagnostics, research, therapeutics, and various monitoring processes have been developed.

This technique utilizes aspects of biological molecules at a molecular level. The identification of the sites and action of ligand-receptor interactions is essential for a molecular understanding of biology and pathology and for the development of novel therapeutics and other products including anti-microbial agents and pesticides. For example, enzymes, antibodies, receptors and nucleic acids respectively bind their substrates, antigens, ligands or complimentary strands with high specificity in the presence of thousands of other biomolecules. This specific binding is referred to as "biomolecular recognition". For example, antibodies may recognize a single amino acid change in a protein. Likewise, enzymes specifically bind substrates in the presence of a multitude of molecules having similar structures, even when these other molecules are present in higher concentrations. For example, the accuracy of protein synthesis is insured by the specificity of a family of enzymes, called aminoacyl-tRNA synthetases. These enzymes act to charge tRNAs with their cognate amino acids.

New technologies are revolutionizing genomic research. For example, on-line microfluidic systems have been described for high-throughput DNA genotyping (Zhang et al, (1999) *Anal Chem* 71: 1138–45), polymerase chain reactions, and DNA sequencing reactions (Wooley et al. (1996) *Anal. Chem.* 68: 720–723). Results from massively parallel and quantitative gene expression measurements analyzing up to 40,000 genes at a time and whole-genome variant detection methods show the power and accuracy of combining biorecognition phenomena with miniaturized array based methods (Lipshutz, et al. (1999) *Nat. Genet.* 21: 20–24). Microarrays detect gene expression levels in parallel by measuring the hybridization of mRNA to many thousands of genes immobilized at high spatial resolution on a surface (Reviewed in Watson et al. (1998) *Curr. Opin. Biotech.* 9:609–614). Highly resolved detection is generally achieved by the laser induced fluorescence of a labeled probe. Capillary array electrophoresis, where many capillaries are run and detected in parallel, has recently been developed for rapid DNA sequencing (reviewed in Kheterpal and Mathies (1999) *Anal. Chem.* 71:31A–37A).

Unfortunately, recent advances in rapid micro gene analysis have not been duplicated for protein or polypeptide analysis or for amino acid analysis. This lack of development is unfortunate because, as stated above, protein and polypeptide amino acid compositional and amino acid sequence analysis are pivotal to biological research and the applications for amino acid analysis are vast. Thus, there is a long-felt need for new means of amino acid analysis which is simpler, faster, and cheaper.

N- and C-terminal amino acid sequence information can be used to verify start and stop points of protein coding sequences, to identify proteins and to identify proteolytic degradation products. Terminal sequences as short as four or five amino acid can often be useful in designed oligonucleotides for polymerase chain reaction or hybridization analyses.

Using carboxypeptidases and aminopeptidases along with amino acid analysis for protein end group sequencing is known. Over the years, these enzymes have been used in discontinuous kinetic assays for protein end group sequencing. Proteins are typically digested by these enzymes and samples of the digests are taken at various time points and analyzed later using an amino acid analyzer. However, due to the nonlinear rate of hydrolysis by these enzymes, kinetic assays have been unsuccessful in most cases. When an analyte varies rapidly and unpredictably, as in the case here, a continuous (real time) assay is needed. However, no continuous amino acid analyzers exist.

Further, automated methods are not presently available for identifying C-terminal sequences of proteins. C-terminal sequence tags are more specific than N-terminal sequence tags of the same length, but no reliable, sensitive method for C-terminal protein sequencing is currently available. Accordingly, new rapid methods for amino acid analysis and end-group protein sequencing are needed.

It would be advantageous to have a real time amino acid analyzer which could be used with exopeptidases, enzymes that remove amino acids sequentially (i.e., one at a time) from a protein's N- or C-terminus, to create integrated protein end group sequenators which microsystems would be suitable for generating either N- or C-terminal sequence tags from intact proteins or peptides on a microscale.

It would further be advantageous to have a method which alleviates at least some of the bottlenecks associated with drug discovery and large scale proteome projects created by the inadequacies in the current methods of amino acid analysis and allows rare proteins and peptides that can be isolated only in minute amounts to be analyzed for amino acid composition. Further, it would be advantageous to have a method, which requires only a tiny amount of sample for each measurement, shorter analysis time, and in situ and real time analyses. Further, it would be advantageous to have a system, which could be mass-produced at lower costs, thus enabling disposable, inexpensive amino acid analysis. Further, it would be advantageous to have a system for the simultaneous analysis of many samples and achieve greater sensitivity. Quite surprisingly, the present invention fulfills these and other needs.

SUMMARY OF THE INVENTION

The instant invention provides methods, compositions, kits, and systems for the detection or analysis of the primary protein amino acids by biomolecular A recognition. The methods, compositions, kits, and systems may be used to analyze an amino acid either individually or in combination with other amino acids. The amino acids may be analyzed in parallel and/or simultaneously. The methods, compositions, kits, and systems of the present invention analyze each amino acid by detecting the reaction products of amino acid-specific proteins that interact predominantly with the corresponding primary amino acid acid. The extent or rate of the interaction provides a measure of the amount of the amino acid present. The primary protein amino acids which are identifiable in accordance with the instant invention are arginine, alanine, cysteine, aspartic acid, glutamic acid, phenylalanine, glycine, histidine, isoleucine, lysine, leucine, methionine, asparagine, proline, glutamine, serine, threonine, valine, tryptophan, and tyrosine.

Methods, compositions, and apparatus are disclosed for the detection or analysis of one or more primary protein amino acids using biomolecular recognition. In one aspect, the invention employs amino acid-specific enzymatic reactions to produce reaction products that may be detected. In a preferred embodiment, the invention employs enzymatic reactions which form amino acid-specific reaction products and those amino acid-specific reaction products are detected. In each case, the extent of these reactions and their reaction products will vary according to the amount or concentration of the analyte amino acid.

In one aspect of the invention, the reactions may be catalyzed by amino acid-specific enzymes which are spatially separated or differentially labeled. The location of the reaction or nature of the label thereby serves to identify the amino acid being analyzed. In a further embodiment, the reactions are analyzed simultaneously or nearly simultaneously, primarily through detection and identification of the reaction products.

In another aspect, the reactions are catalyzed by enzymes and the amino acid-specific substrates are spatially separated or differentially labeled. The location of the reaction or the differential label serves thereby to identify the amino acid being analyzed. In a further embodiment, the reactions are analyzed simultaneously or nearly simultaneously, primarily through detection and identification of the reaction products.

In accordance with the invention, the binding of a specific enzyme may be identified in a number of ways. For example, the binding may be measured directly. Alternatively, the binding to the specific enzyme may be detected by monitoring the reaction(s). The reactions may be monitored by following the conversion of reactants into unique products or intermediates. Products may also be coupled to other enzymatic reaction products to produce detectable products.

Alternatively, in accordance with the instant invention, products can first be bound by other biomolecular recognition molecules and the resultant product or complex detected by use of ligand assays (binding assays). An exemplary binding assay uses high-specificity fluorescent or chemiluminescent labels.

In accordance with another aspect of the invention, immobilization chemistries can be used for direct and indirect identification and/or detection of an amino acid.

In still another aspect of the invention, certain homogeneous binding assays are used to monitor the reaction or reactants. The physiochemical properties of the tracer or label changes upon binding to the receptor thus allowing direct monitoring of the bound form without prior separation of the bound form from the unbound. For example, suitable homogeneous binding assay systems may use labels detectable by time-resolved fluorescence, fluorescence correlation spectroscopy, fluorescence polarization, fluorescence energy transfer and scintillation proximity assays.

In another aspect of the invention, the reactants or reaction products are detected by antibodies, proteins, peptides, or oligonucleotides which specifically bind a specified molecule with the desired affinity. Antibody engineering, phage display, combinatorial chemistry, and directed evolution are used to produce such detector molecules.

In another aspect of the invention, methods of miniaturization and automation are used to detect specific amino acid(s). Ultrasensitive ligand assays using laser-induced fluorescence have sensitivities approaching the single molecule level. Accordingly, the present methods can be used to measure the concentration of amino acids in small amounts of sample, at high sensitivity and at relatively low cost. The microscale systems of the present invention can be adapted for continuous or discontinuous operation.

A number of reactions may be employed. Particularly preferred reactions are the reactions catalyzed by the aminoacyl-tRNA synthetases. In this case, the primary protein amino acids which are identifiable in accordance with this invention are those, which in preparation for protein synthesis, are attached to their corresponding or cognate tRNAs by the corresponding or cognate aminoacyl-tRNA synthetase. Specifically, these primary amino acids are arginine, alanine, cysteine, aspartic acid, glutamic acid, phenylalanine, glycine, histidine, isoleucine, lysine, leucine, methionine, asparagine, proline, glutamine, serine, threonine, valine, tryptophan, and tyrosine.

The reactions catalyzed by the aminoacyl-tRNA synthetases are:

a. Aminoacyl-tRNA synthetase+AA+ATP⇌Aminoacyl-tRNA synthetase:AA-AMP+PPi (Reaction A)

b. Aminoacyl-tRNA synthetase:AA-AMP+tRNA-⇌AA-tRNA+AMP+Aminoacyl-tRNA synthetase (Reaction B).

In accordance with the instant invention, the identification of each amino acid (AA) by its cognate synthetase may be determined by following the formation of aminoacyl-tRNA synthetase:Amino Acid AMP (AA-AMP) and/or inorganic pyrophosphate (PPi) in accordance with Reaction A or by following the formation of aminoacyl-tRNA and/or AMP in Reaction B and/or combinations thereof. A number of suitable buffers for the reactions catalyzed by the synthetases and the binding of AA-tRNAs to the EF-Tu:GTP complex are known in the art.

In accord with the present invention, an aminoacyl-tRNA synthetase:AA-AMP Reaction A is formed and detected in the absence of the corresponding tRNA. In other embodiments, amino acids are analyzed by monitoring the formation of the AMP or aminoacyl-tRNAs in Reaction B.

In still another aspect, at least one primary amino acid is contacted with at least one aminoacyl-tRNA synthetase to yield an aminoacyl-tRNA synthetase:AA-AMP+PPi and the aminoacyl-tRNA:synthetase:AA-AMP reaction product is then contacted with cognate tRNA to produce AA-tRNA+AMP and a product of this second reaction is detected.

In another aspect of the invention, an elongation factor such as 1A.GTP, or EF-Tu:GTP in bacteria, binds the aminoacyl-tRNA to be detected and the amino acid identified by location of the binding or by the differential labeling associated with the binding.

In accordance with the broad aspect of the instant invention, at least one primary protein amino acid, present in a sample, is detected using biomolecular recognition by contacting at least one aminoacyl tRNA synthetase with the primary protein amino acid to yield detectable products or co-products wherein said primary protein amino acid is selected from the group consisting of arginine, alanine, cysteine, aspartic acid, glutamic acid, phenylalanine, glycine, histidine, isoleucine, lysine, leucine, methionine, asparagine, proline, glutamine, serine, threonine, valine, tryptophan, tyrosine and mixtures thereof to form a unique detectable product, and detecting such unique detectable product.

In accordance with another aspect of the invention, sequential detection of specific primary protein amino acids in a protein is accomplished by initially combining the protein with a carboxypeptidase or an aminopeptidase to liberate amino acids, sequentially, and reacting the released amino acid with a specific aminoacyl tRNA synthetase to yield the aminoacyl tRNA synthetase:Amino Acid AMP complex.

In another aspect of the invention, a single amino acid can preferably be targeted for measurement by detecting the AA-tRNA product of Reaction B by binding the product to an elongation factor.

In accordance with the instant invention, arrays having a plurality of aminoacyl tRNA synthetases and/or specific tRNAs are provided. The aminoacyl tRNA synthetases and/or specific tRNAs are positioned into or transported through a separate chamber (e.g., microwell, microcapillary or microchannel) or immobilized in a separate location on a surface (e.g., bead, microparticle or microchip), or immobilized on a separate bead or particle, or on a separate transducer (e.g., an optical fiber, electrode or piezoelectric crystal). A plurality of synthetase reactions may thus be monitored in a spatially resolved manner.

Spatially resolved microarrays and microflow systems are also provided. These systems allow multianalyte analysis methods and may use multiple labels or separately positioned biorecognition molecules and spatially specific detectors to provide amino acid-specific analysis of a sample. The systems of the present invention optionally include such detectors as laser-induced fluorescence and imaging detectors (e.g., CCD detectors), scanning detectors (e.g., confocal scanners), piezoelectric detector systems or surface plasmon resonance detection systems.

In accordance with the present invention, microscale elongation factoraminoacyl-tRNA (AA-tRNA) synthetase systems and methods are employed for analyzing any one of, or up to all twenty of, the primary amino acids. By monitoring the reactions catalyzed by the enzymes simultaneously or in a spatially resolved manner, the primary amino acids can be quantitated, semi-quantitated, and/or identified. For instance, elongation factor 1 Alpha (i.e., elongation factor 1A, EF1A) from eukaryotic cells or elongation factor Tu (EF-Tu) from prokaryotic cells when bound to GTP binds to AA-tRNAs produced in Reaction B with high affinity. For instance, bacterial EF-Tu binds to an aminoacyl tRNA with a Kd of about $10^{-9}$ M but not a tRNAs lacking an aminoacyl moiety. Wheat germ EF-1A:GTP bounds AA-tRNA with a similarly high Kd of about $10^{-9}$ M. (See Dreher T W (1999) *JBC* 274:666–72. Thus, known ligand assays can then be used to monitor the concentration of amino acids in a sample.

Other features, objects and advantages of the invention and its preferred embodiments will become apparent from the detailed description and claims which follow.

BRIEF DESCRIPTION OF THE DRAWINGS

FIG. 5A is a schematic drawing of a continuous flow C-terminal nanosequenator.

FIG. 5B further illustrates a continuous flow C-terminal nanosequenator of the present invention.

FIG. 5C is a schematic drawing of a flow optical fiber nanosequenator for use with the current invention.

FIGS. 7A–7B show two modes for ultrasensitive amino acid analysis in continuous microflow displacement systems.

FIG. 8B illustrates an embodiment where each synthetase and the elongation factor are indirectly immobilized as microspots via a ligand-ligand binding system.

FIG. 8C shows an embodiment in which tRNAs, one specific for each of the protein amino acids, are arrayed as microspots. Amino acids in a sample are attached to the tRNAs by their cognate synthetases, and fluorescently labeled EF-Tu:GTP binds the arrayed AA-tRNAs.

FIG. 8D illustrates an embodiment of a high density C-terminal end group analysis microarray.

In FIG. 19A, the ternary complex is labeled with an enzyme label and reversibly bound inside a microchannel using an antibody that specifically binds the ternary complex.

FIG. 19B shows an amino acid analyzer microbiosensor that uses continuous flow displacement with electrochemical detection.

FIG. 24 is a schematic of three biosensors for use as detectors according to the present invention. The biosensors are electrochemical, optical waveguide, and plasmon resonance biosensors.

DETAILED DESCRIPTION OF THE INVENTION

Figure 1A:
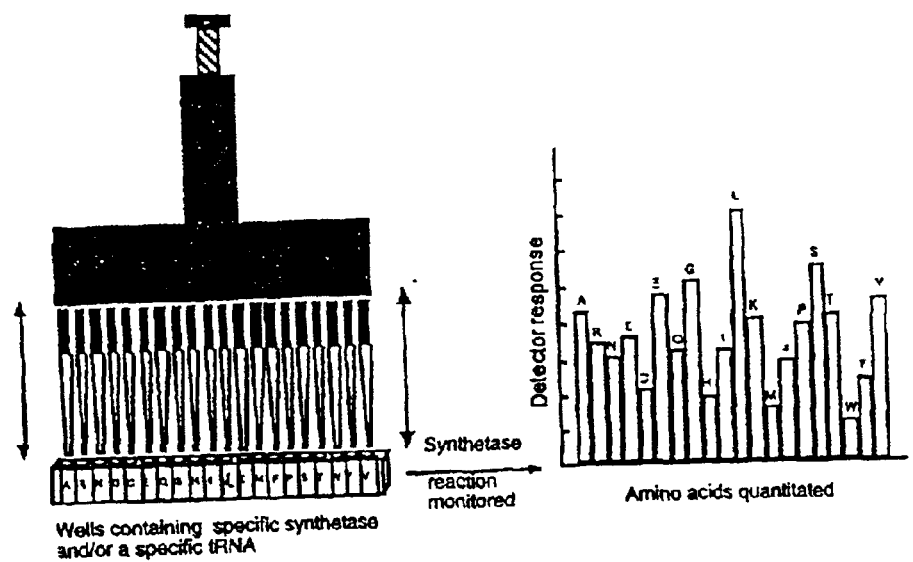
FIG. 1A illustrates an enzymatic amino acid analyzer having a multichannel pipettor, suitable for simultaneously mixing and dispensing a solution of the primary amino acids into the amino acid specific wells in a microtiter plate format FIG. 1B graphically illustrates an ultrasensitive ligand assay for the determination of the aminoacyl tRNA as a ternary complex in a microtiter plate format FIGS. 2A and 2B generally illustrate some tRNA and synthetase microarrays according to the present invention.

The present invention will now be described more fully hereinafter with reference to the accompanying drawings, in which some preferred embodiments of the invention are shown.

Unless otherwise defined, all technical and scientific terms used herein have the same meaning as commonly understood by one of ordinary skill in the art to which this invention belongs. Each publication, patent application, patent, and other reference cited herein is incorporated by reference in its entirety to the extent that it is not inconsistent with the present disclosure.

It is note here that as used in this specification and the appended claims, the singular forms "a," "an," and "the" include plural reference unless the context clearly dictates otherwise.

As used herein, the primary amino acids/protein primary aminoacids are the following amino acids commonly found in proteins. These amino acids have three- and one-letter abbreviations routinely used in the art: A, Ala, Alanine; C, Cys, Cysteine; D, Asp, Aspartic Acid; E, Glu, Glutamic Acid; F, Phe, Phenylalanine; G, Gly, Glycine; H, His, Histidine; In, Ile, Isoleucine; K, Lys, Lysine; L, Leu, Leucine; M, Met, Methionine; N, Asn, Asparagine; P, Pro, Proline; Q, Gln, Glutamine; R, Arg, Arginine; S, Ser, Serine; T, Thr, Threonine; V, Val, Valine; W, Try, Tryptophan; Y, Tyr, Tyrosine.

An "array" has a plurality of means for separately analyzing a plurality of the primary amino acids or a plurality of amino acid samples. Arrays can be based on spatial separation of biomolecular recognition elements or on the differential labeling of such elements. For example, in a differential labeling array, analyte-specific biorecognition molecules (e.g., aminoacyl-tRNA synthetases or tRNAs) may be uniquely labeled so that each synthetase or tRNA specific for a different amino acid is uniquely identified by the label. In a spatial array, for example, each unique tRNA or synthetase may be uniquely localized (e.g., immobilized to a uniquely labeled particles or spot such as a microtiter well), thereby forming an array. Each specific synthetase or tRNA bearing a unique label in this case is an array.

In the present context, a reaction fluid or buffer comprises an appropriate buffer the substrates, ions, and factors necessary for the subject reaction to occur. Examples of reaction buffers for the various reactions are provided below. A reaction fluid for the aminoacyl synthetease reaction buffer would require, among other constitutents, at least one aminoacyl-tRNA synthetase and usually at least one cognate tRNA.

As used herein, a molecular sieve separates molecules according to size or molecular weight. A molecular sieve can include a selectively permeable membrane, a microdialysis membrane or a microdialysis probe. In a preferred embodiment, free amino acids pass while proteins and other molecules of greater than about 6 kDa are retained.

In the present application, two components of a device are in fluid communication with one another if liquid can pass from one to the other. The flow of liquid can be due to diffusion, capillary action, gravity or due to the action of a pump, such as a microfluidic pump.

As used herein, two components are in electronic communication if an electronic signal can pass from one to the other (in at least one direction). For example, a signal from a detectable tag in a ternary complex is passed, in electronic form, from the detection system to a computer microprocessor where the signal can be processed and/or recorded.

When an electronic signal is decoded, information about the presence and/or quantity of at least one primary amino acid is generated by the computer or microprocessor.

A biorecognition molecule is one which preferentially binds to another molecule. Biomolecular recognition molecules comprise aminoacyl-tRNA synthetases, tRNAs, elongation factors, antibodies, antibody fragments, aptamers, peptides, nucleic acids, oligonucleotides, peptide nucleic acids, ribosomes, proteins, or fragments thereof, that retain biorecognition binding activity.

The biorecognition element can be a partner in an immobilization system, for example, when a component is linked to biotin, streptavidin or avidin can serve as a biorecognition element. If the streptavidin or avidin is bound to a surface, it can then mediate binding of a molecule linked to biotin.

An antibody can serve as a biorecognition element for a particular molecule to which it binds, or an oligonucleotide can serve as a biorecognition element for a nucleic acid molecule (or region thereof) which is complementary to the oligonucleotide, and surface localization can be thus mediated.

As with antibodies, oligonucleotides or peptide aptamers that specifically recognize an analyte can be produced using known methods. Aptamers are a particularly attractive class of biomolecular recognition elements. Apatamers can now be provided which can recognize virtually any class of target molecule with a high affinity. (See Jayasena S D (1999) *Clin Chem* 45:1628–50; Kusser W. (2000) *J. Biotechnol.* 74: 27–39; Colas P. (2000) *Curr Opin Chem Biol* 4:54–9.) Aptamers which specifically bind arginine and AMP have been described as well (see Patel D J and Suri A K, (2000) *J. Biotech.* 74:39–60.

Elongation factor IA or Tu:GTP can serve as a biorecognition element for an aminoacyl-tRNA. Other examples are obvious to one of ordinary skill in the art.

A sample, as used herein, can be any material in which the determination of the presence or quantity of at least one primary amino acid is carried out. The sample can be a biological sample including, but not limited to, blood, serum, cerebrospinal fluid, fermentation broth, proteolytic digest or cell culture medium. Pharmaceutical and nutritional supplement compositions and other food products are also within the scope of "sample".

In a preferred embodiment, the method is applied to amino acid samples derived from protein end group sequencing by carboxypeptidase or aminopeptidase digestation of the protein. Over the years, these enzymes have been used in discontinuous kinetic assays for protein end group sequencing. Proteins are typically digested by these enzymes and samples of the digests are taken at various time points and analyzed later using an amino acid analyzer.

The use of controls and standard curves for determining the concentration of an analyte are well known fundamentals in the art. For instance, the concentrations of amino acids in a sample may be determined by reacting the amino acid with a cognate aminoacyl-tRNA synthetase and measuring the formation of a product and comparing that value with one or more corresponding values obtained in the same way using one or more standard samples of known amino acid concentrations. A preferred embodiment provides a standard curve for each of the primary amino acids to be analyzed. In another preferred embodiment, a microprocessor receives the detection signal and thereby analyzes the data according to a standard curve to provide a signal indicative of the amount or concentration of the amino acid in the sample tested.

Aminoacyl-tRNA Synthetase-Based Methods

Preferred embodiments of the present invention utilize one or more of the following reactions catalyzed by the aminoacyl-tRNA synthetases (reviewed in Schimmel, P. (1987) *Annu. Rev. Biochem.* 56:125–158; Friest, W. (1989) *Biochemistry* 28:6787–6785; Schimmel P. (1993)) *FASEB J.* 7:282–9; and Cusack S. (1997) *Curr. Opin. Struc. Biol.* 7:881–9) to detect and or quantitate the amino acid(s):

a. Aminoacyl-tRNA synthetase+AA+ATP⇌Aminoacyl-tRNA synthetase:AA-AMP+PPi (Reaction A)

b. Aminoacyl-tRNA synthetase:AA-AMP+tRNA⇌AA-tRNA+AMP+Aminoacyl-tRNA synthetase (Reaction B).

In the above reactions, the aminoacyl tRNA synthetase and the tRNA substrate each are specific to a particular amino acid. The reaction may be followed by measuring any of the reactants or intermediate complexes. As described in detail below, particularly preferred embodiments measure an amino acid-specific product, the aminoacyl-tRNA synthetase:AA-AMP complex or the AA-tRNA. Other embodiments may measure the AMP or PPi products of an above reaction. For example, AMP may be detected or measured by reacting it with an AMP binding protein or nucleic acid (e.g., an RNA apatamer).

Reaction Conditions

The reactions employed to detect amino acids in the subject invention will be conducted in a suitable buffer and conditions that depend on the particular assay format, biomolecules, and biochemicals used for detection of the amino acids.

Buffers including wash buffers, reaction buffers, and binding buffers, elution buffers and the like are known to those or ordinary skill in the arts. See, for example, Negrutskii B. S. et al. (1999) *JBC* 274: 4545–4550; Lloyd A. J. et al. (1995) *Nucl. Acids Res.* 23:2886–2892; and Reed V. S. et al. (1994) *JBC* 269: 32932–36 which are each herein incorporated by reference.

tRNA aminoacylation may be measured with 20 mM imidazole-HCl buffer, pH 7.5, 3 mM KCl, 15% glycerol, 0.5 mM DTE, 5 mMMgCl$_2$, 3 mM ATP, 25° C., and saturating amounts of about 100 uM of tRNA, excess EF-Tu:GTP (e.g., 100 uM with GTP at 1 mM, and 50 ug/ml inorganic pyrophosphatase.

Examples of suitable buffers for the reactions catalyzed by the aminoacyl-tRNA synthetases include but are not limited to the following:

1. 30 mM HEPES-KOH, pH 7.6, 10 mM MgCl$_2$, 50 mM KCl, 1 mM dithiothreitol, 1 mM ATP, 1–300 uM tRNA, 1 nM-300 uM aminoacyl-tRNA synthetase(s), inorganic pyrophosphatase (10 U/ml)23–37° C.

2. 50 mM Tris-HCl, pH 7.9, 10 mM MgCl2, 50 mM KCl, 2 mM dithiothreitol, 2 mM ATP.

3. 80 mM Tris-HCl, pH 7.8, 100 mM KCl, 10 mM MgCl$_2$, 3 mM ATP, 35° C.

4. 100 uM tRNA, 150 mM Tris-HCl, pH 7.5, 75 mM KCl, 100 mM MgCl$_2$, 5 mM ATP, 1 nM-300 uM aminoacyl-tRNA synthetase.

When the product of Reaction A is to be detected and otherwise, inorganic pyrophosphatase is optionally added to prevent the reverse direction of Reaction A (synthetase+ATP+AA⇌synthetase:AA-AMP+PPi) and to eliminate possible inhibition of the synthetases by pyrophosphate.

In the case of gluatminyl, glutamyl, and arginyl-tRNA synthetases, formation of the aminoacyl adenylation product of Reaction A also requires the cognate tRNA.

Where the amino acid analysis is to be quantitative, the reagents used to detect the amino acids are preferably in molar excess over the amino acids in solution. Sufficient EF-Tu:GTP preferably is provided to bind every AA-tRNA in the sample. Where amino acids are converted into AA-tRNAs, tRNAs are also preferably in excess. ATP is preferably also in molar excess. Likewise, in some embodiments where amino acids are detected by forming AA-AMP complexes with the aminoacyl-tRNA synthetases, the synthetases and ATP (or analog thereof) are preferably in excess over the amino acids in the sample. Where the reactions catalyzed by the synthetases are monitored by coupling the reaction product to other enzymatic pathways, an excess of ATP, coupling enzymes, and other chemicals and biochemicals used to detect reaction products is optimally employed.

Enzymatic assays where the aminoacyl tRNA synthetases form AA-tRNAs which subsequently bind to elongation factor:GTP complexes are also known in the art (see, Negrutskii et al. (1999) *JBC* 274: 4545–4550). For example, tRNA aminoacylation and binding to elongation factor:GTP complexes may be conducted at room temperature (25° C.) in a suitable buffer, e.g., 20 mM imidazole-HCl (pH 7.5) 3 mM KCl, 0.5 mM DTE (1,4-dithioerythritol), 5 mM MgCl$_2$, 5 mM ATP, 1 mM GTP.

Aminoacyl tRNA Synthetase

A variety of aminoacyl tRNA synthetases may be used and such enzymes are well known in the art. For instance, the aminoacyl tRNA synthetases from both eukaryotes and prokaryotes are well known. Aminoacyl tRNA synthetases isolated from both prokaryotes and eukaryotes are suitable. The aminoacyl tRNA synthetases are isolated in substantially pure form, particularly with respect to other aminoacyl tRNA synthetases having different amino acid binding to the other amino acids. Preferably, the aminoacyl tRNA synthetases of the present invention are substantially free of other amino acid synthetases and, in relative terms by weight, preferably have no more than 10 to 5%, and most preferably less than 1% of another type of aminoacyl tRNA synthetase. The aminoacyl tRNA synthetases may be made by recombinant techniques or provided from the native gene product.

Preferred aminoacyl tRNA synthetases are selected according to temperature, storage and reaction condition stabilities. One of ordinary skill in the art would appreciate how to screen aminoacyl tRNA synthetases to determine those having a sufficient or optimal stability to temperature, storage, and reaction conditions.

The aminoacyl synthetases from a variety of procaryotes or eucaryotic organisms can be employed in the subject invention and are generally available from commercial sources. Methods for overexpressing the aminoacyl tRNA synthetases are known to one of ordinary skill in the art. For example, see Lechler A. et al. (1996) *Protein. Expr. Purif.* 8:347–57 and Bausch N. et al. (1998) *Biochim. Biophys. Acta* 1397:169–74.

As aminoacyl tRNA synthetases are essential enzymes in protein biosynthesis, they are particularly well characterized. They are reviewed in the following references herein incorporated by reference: Martinis S A et al. *Biochimie* 81:683–700.; Schimmel P. et al. (1988) *FASEB J.* 12:1599–609; DeGuzman R. N. et al. (1988) 48:181–95; Freist W. et al. (1997) *Biol Chem.* 378:1313–29; Freist W. et al. (1996) 377:343–56. Cusak S. (1995) *Nat. Struct. Biol.* 2:824–31; Fukai S. (200) *Cell* 103:793–803; Ibba M and D. Soll (2000) *Ann Rev. Biochem.* 69:617–50; Ibba M. et al. *Trends Biochem. Sci.* 25:311–6; Freist W. et al. (1999) *Biol. Chem.* 380:623–46; and Cavaerli J. et al. (1993) *FSEB J.* 7:79–86.

Detection of the AA-AMP:Synthetase Complex

This reaction product can be detected in a number of ways. For example, ATP may be fluorescently or radioactively abeled in such a way that the fluorescent label would be incorporated into the AA-AMP: synthetase complex. In this case the fluorescent label can be attached to a part of the ATP that remains with the AA-AMP (i.e., it can not be attached to the alpha or beta phosphates that are removed). The fluorescently labeled AA-AMP:synthetase product may be detected using a fluorescent binding assay, for example, a fluorescence polarization assay or other fluorescence binding assays such as those based on fluorescence correlation. This assay is continuous and does not require an immobilization step.

Other methods of detecting the AA-AMP:synthetase complexes involve the immobilization of the aminoacyl-tRNA synthetases. The AA-AMP synthetase complexes may be detected without using a labeling step. For example, the synthetases may be immobilized onto biosensor surfaces such as surface plasmon resonance-based or piezoelectric crystal-based biosensors and the binding of the AA-AMP to the immobilized aminoacyl-tRNA synthetases may be detected directly by the biosensor. When the synthetase is immobilized onto a surface plasmon resonance-based biosensor, the mass change upon binding an AA-AMP can be followed in real time and used to quantitatively detect amino acids cognate to the immobilized synthetase.

Other methods of detecting the AA-AMP:synthetase complex are envisaged that involve both immobilization of the synthetases as well as labeling. Labeled ATP (e.g., radiolabeled or fluorescently labeled ATP) is used as a substrate and becomes incorporated into the AA-AMP:synthetase complexes. The amino acids are detected by detecting the label in the immobilized complex.

Other label-based assays known in the arts may be employed to monitor the binding of AA-AMPs to the aminoacyl-tRNA synthetases. These assays include, but are not limited, to those based on fluorescence polarization, scintillation proximity assays, and fluorescence correlation spectroscopy (Reviewed in Tetin, S. W and Hazlett, T. L (2000) *Methods* 20: 341–361; and Fernandes, P. B. (1998) *Curr. Opin. Chem. Biol.* 2:597–603).

Detection of the Inorganic Pyrophosphate

The reaction product inorganic pyrophosphate (PPi) may be detected in solution without immobilization or labeling. For example, an assay that continuously monitors PPi production in the first step catalyzed by the aminoacyl-tRNA synthetases may be used. In this example synthetase-dependent PPi production is monitored in the presence of excess pyrophosphatase to generate about 2 mol phosphate (Pi) per mol of aminoacyl-AMP (AA-AMP) formed. The Pi is then detected. For example, phosphate production may be coupled to the phosphorolysis of a chromogenic substrate. For example, the chromogenic nucleoside 2-amino 6-mercapto 7-methylpurine (AMMP) may be used. The AMMP base has a high absorbance at 360 nm relative to AMMPR (Webb, M R, 1992, *Proc. Natl. Acad. Sci.* USA, 89 4884–4887) and so provides a spectrophotometric signal that can be continuously followed. The reaction scheme is:

(1) aminoacyl-tRNA synthetase+AA+ATP$\leftrightharpoons$aminoacyl-tRNA synthetase:AA-AMP+PPi (catalyzed by the aminoacyl-tRNA synthetases);

(2) PPi+$H_2O\leftrightharpoons$2Pi (catalyzed by inorganic pyrophosphatase);

(3) 2Pi+2 AMMPR$\leftrightharpoons$2-ribose 1-phosphate+2 AMMP (catalyzed by purine nucleoside phosphorylase).

This method has been used to monitor Reaction A. (See, Lloyd et al, 1995, *Nucleic Acid Research* 23: 2886–2892)

In addition, a fluorescent probe has been described that can readily measure inorganic phosphate (Pi) as released by enzymes, such as inorganic pyrophosphatase, in real time in biological systems (Brume et al. (1994) *Biochemistry* 33: 8262–8271). This reaction can be used to detect the PPi produced in Reaction A and hence amino acids.

Continuous methods for following the formation of PPi as produced in Reaction A are known in the art and are suitable for use in some embodiments of the current invention. For example, a continuous spectrophotometric assay for measurement of inorganic phosphate that is released from PPi upon hydrolysis by inorganic pyrophosphatase has been used to follow Reaction A. (See, Lloyd et al. (1995) *Nucleic Acids Res.* 23:2886–2892). In addition, a fluorescent probe has been described that can measure inorganic phosphate as released by enzymes such as inorganic pyrophosphatase in real time in biological systems (See, Brume et al. (1994) *Biochemistry* 33:8262–8271).

Detection of the Aminoacyl tRNA

In another assay to follow the reactions catalyzed by the synthetases, the formation of AA-tRNAs in Reaction B is monitored. The reaction product AA-tRNA may be monitored by binding it to a molecule that specifically binds AA-tRNAs and detecting the AA-tRNAs after they have bound the molecule. For example, antibodies or oligonucleotide aptamers that specifically bind AA-tRNAs may be produced using known methods and used to bind and detect AA-tRNAs. Other proteins that specifically bind AA-tRNAs may be employed.

The critical fidelity of protein synthesis depends upon the remarkable ability of the synthetases to recognize their cognate amino acids and tRNAs and upon the ability of EF-Tu:GTP to discriminate between AA-tRNAs and tRNAs. Rather than separating the amino acids by chromatography, each synthetase or a tRNA specific for a different amino acid is separately positioned, and the amino acids are analyzed from a mixture by monitoring the reactions catalyzed by the synthetases in a spatially resolved manner.

By using a macromolecule that specifically binds the AA-tRNAs with high affinity, ligand binding assays that are far more sensitive than spectroscopic assays to follow the aminoacylation reactions are produced, as described herein. The art has produced powerful screening methodologies that allow selection of biological molecules (antibodies, antibody fragments, peptides, proteins, and nucleic acids) that bind a specific molecule with the desired specificity and affinity. Protocols that allow one to select (directly or after in the laboratory evolution) a biomolecular ligand that specifically binds the desired molecule are well established in the art. Hence, molecules that speifically bind AA-tRNAs are used to follow the reactions catalyzed by the synthetases. Biomolecules that specifically bind AA-tRNAs with the desired affinities can be selected using known methods. Examples of molecules that specifically bind the AA-tRNAs include, without limitation, antibodies or parts of antibodies, oligonucleotides (e.g., DNA or RNA aptamers), peptides, or proteins or parts of proteins.

A ternary complex probe, as used herein, specifically binds to the complex of aminoacyl-tRNA bound to an elongation factor. It can be a complex-specific antibody or an aptamer. For flow displacement systems, the antibody or other ternary complex probe used to reversibly bind the labeled molecule is chosen to have a relatively fast dissociation rate constant. Dissociation rate constants can be determined rapidly using biosensor technology (Pellequer et al. (1993) *J. Immunol. Meth.* 166:133–143).

The current invention additionally provides a novel assay for following the formation of all AA-tRNAs using a binding assay. Elongation factor Tu complexed to GTP binds all AA-tRNAs with high affinity forming a stable ternary complex. Therefore, by following the binding of AA-tRNAs to the elongation factor:GTP binary complex, he overall reactions catalyzed by the synthetases is monitored. This assay is especially advantageous. Since both AA-tRNAs and the elongation factor are macromolecules, ultrasensitive assays may be devised that employ, for example, high specific activity labels. This assay is applicable to microchannel and microarray systems as well as affinity biosensors.

For example, the protein elongation factor Tu, when complexed with GTP (EF-Tu:GTP), binds each of the AA-tRNAs with high specificity, thus forming a stable ternary complex (EF-Tu:GTP-AA-tRNA). EF-Tu; GTP (or a fragment thereof which retains the sensitive and specific binding of AA-tRNA) or a homologous protein such as elongation factor a alpha or mitochondrial EF is a useful binder of (i.e., ligand for) AA-tRNAs in this invention. Accordingly, if EF-Tu:GTP is present with the synthetases and tRNAs the following reaction will occur:

Preferred elongation factor are factors from thermophillic organism such as EF-Tu from *Thermus thermophilus* which is described in detail by Grillenbeck B J et al. (1995) *Protein Expr. Purif.* 6:637–45. Methods for purifying, and overexpressing elongation factors are described in the prior art. For example, Ribierio et al. teach a method for overexpressing EF-Tu from *Thermus thermophilus*. The gene coding for EF-Tu was expressed under the control of the tac promoter. A detailed description of the purification of the elongation factor is described therein. Further information on the elongation factors is found in Nissen et al. (1995) *Science* 270:1453–4; Bilgin N. et al. (1998) *Biochemistry* 37:8163–72. Reviews of the elongation factors Lijas A. and M. (1995) *Curr Opin. Struct. Biol.* 5:721–7; Negretskii B. S., et al. (1998) *Prog. Nucleic Acid Res. Mol Biol.* 60:47–78; and Krab I. M. and Parmeggiani A. (1998) *Biochim Biophysics Acta* 1443:1–22. See also Nyborg J. (1977) *Curr Opin Struct. Biol.* 7:110–6; Schmitt E. et al. (1966) *Biochimie* 78:543–54; Cai Y. C. et al. (2000) *J. Biol. Chem.* 275:20308–14; Nissen P. et al. (1999) *Structure Fold Des.* 7:143–56; Liu G. et al. (1996) *J. Cell Biol.* 135:953–63; Liljas A and Garber M.(1995) *Curr Opin Struct Biol.* 5:721–7; and Reshetnikova L. S. et al. (1991) *J. Mol. Biol.* 221:375–7. Each of the preceding references is herein incorporated by reference in their entirety.

The ternary complex maybe further stabilized by substituting a nonhydrolyzable GTP analog such as GDPNP, as known in the art (Wagner et al. (1995) *Biochemistry* 34:12535–12342; Nissen et al. (1995) *Science* 270:1464–1472). Both EF-Tu:GTP and EF-Tu; GDPNP have a high affinity for all AA-tRNAs while effectively discriminating against tRNAs which are not aminoacylated. The amount of ternary complex formed is generally proportional to the concentration of the amino acid cognate to the tRNA and synthetase present. Hence, the amino acids are identified and quantitated by following the formation of the ternary complex. This can be accomplished by labeling either the tRNAs, elongation factor, ternary complex, or a ternary complex probe (a molecule that specifically binds the ternary complex (e.g., antibody, aptamer, peptide, ribosome or ribosomal subunit) and quantifying the label. tRNAs have been fluorescently labeled (see, e.g., Janiak et al. (1990) *Biochemistry* 29:4268–4277). The fluorescently labeled tRNAs are functional in aminoacylation and in binding to elongation factors. Alternatively, the ligand assays may be based on label-free affinity biosensors (e.g., surface plasmon resonance-based biosensors or piezoelectric biosensors). Ligand assays using fluorescent labels typically achieve femtomole or attomole sensitivities (Zubritsky, E. (1999) *Anal. Chem.* 71-39A–43A).

In other assays used to detect AA-tRNAs, either the molecules that specifically bind AA-tRNAs or the tRNAs are immobilized. For example, if EF-Tu:GTP (or another molecule that specifically binds AA-tRNAs) is immobilized, it may be used to capture AA-tRNAs. The captured AA-tRNAs may be detected without a labeling step. For example, captured AA-tRNAs may be analyzed by mass spectrometry. Each unique amino acid attached to an isoacceptor tRNA will have a unique mass that will allow the amino acid to be identified. Captured molecules may be detected by using any method for the detection of tRNAs. These include staining with dyes such as ethidium bromide. Additionally, PCR based methods may be used to amplify captured tRNAs for detection. Further, the EF-Tu:GTPs, tRNAs or synthetases may be immobilized onto biosensor surfaces such as surface plasmon resonance-based biosensors, thermal sensors, and acoustic wave devices that do not require a label to monitor a binding reaction. The binding of AA-tRNAs to the immobilized EF-Tu:GTPs are detected by certain biosensors without a labeling step.

Immobilized tRNAs may also be used to detect amino acids by detecting the formation of AA-tRNAs. Where tRNAs are immobilized they are contacted with a cognate amino acid and a cognate aminoacyl-tRNA synthetase. The synthetases attach cognate amino acids to the immobilized tRNAs forming immobilized AA-tRNAs. The immobilized AA-tRNAs are then contacted with a molecule that specifically binds the AA-tRNAs and the binding of this molecule to the immobilized AA-tRNAs is detected. This may be achieved without using a labeling step. For instance, the tRNAs may be immobilized on biosensor surfaces. Certain biosensors such as surface plasmon resonance-based biosensors, thermistors, and acoustic-wave devices detect binding reactions without a labeling step. Hence, the binding of EF-Tu:GTP (or another molecule that specifically binds AA-tRNAs) to AA-tRNAs on the surfaces of certain biosensors may be monitored without a labeling step.

Alternatively, a molecule that specifically binds AA-tRNAs can be labeled and then contacted with the immobilized AA-tRNAs. The labeled molecule is detected after binding the immobilized AA-tRNAs by detecting the label. Alternatively, or additionally the immobilized tRNAs may be labeled with fluorescent labels and the change in fluorescence after or upon binding the AA-tRNA specific molecule is detected by the change in fluorescence upon binding.

Heterogeneous binding assays for amino acid analysis are provided herein. For example, either the EF-Tu:GTP or tRNA is immobilized on a surface. After reaction with the aminoacyl-tRNA synthetases and the amino acid sample, the tRNAs are converted into AA-tRNAs which bind EF-Tu:GTP forming the ternary complex EFTu:GTP:AA-tRNA. The free member of the binding complex, AA-tRNA or EF-Tu:GTP, which may optionally be labeled, is captured by the immobilized member of the complex. In embodiments where the EF-Tu:GTP is immobilized, the AA-tRNAs may be captured and detected. In other embodiments, the tRNAs may be immobilized. After reaction with the aminoacyl-tRNA synthetases and amino acid sample, immobilized AA-tRNAs are produced. The AA-tRNAs are reacted with EF-Tu:GTP which binds to AA-tRNAs with high affinity. A wash step is employed to remove unbound substances and the captured member of the ternary complex is detected.

Another example of a heterogeneous binding assay of the subject involves immobilizing the aminoacyl-tRNA synthetases and monitoring the binding of AAA-MP to the immobilized complexes. In this embodiment, each aminoacyl-tRNA synthetase is immobilized to a surface. The immobilized synthetases are reacted with amino acids and ATP in reaction buffer and the binding of the AA-AMP to the synthetase is monitored. For heterogeneous assays a wash step is employed. Labeled ATP, (e.g., radiolabeled or fluorescently labeled) is used. A wash step is used to remove unbound assay components (e.g., the unbound labeled ATP). Next, the labeled AA-AMP is detected. The synthetases may be immobilized to beads, the bottoms of wells, e.g., the bottom of microtiter plate wells, optical fibers, microchips, filters, films, or other surfaces. In labeling the ATP for this embodiment it is essential to have the label in a part of the ATP molecule that remains with the AA-AMP complex. That is, the label may be in the ribose, adenine or alpha phosphate.

As set forth above, additional aspects of the present invention include ultrasensitive ligand assays for amino acid analyses. In this method, separately positioned synthetases or tRNAs are used in devices for quantitatively or semi-quantitatively discriminating among the 20 amino acids. The synthetase reactions may be followed in one of several methods known in the art. The synthetase reaction may be monitored by following the binding of AA-tRNAs to EF-Tu:GTP. Although the elongation factor is one preferred binder of the AA-tRNAs, another molecule that specifically binds AA-tRNAs can be used with the same effects. Where the binder is referred to a EF-Tu:GTP it is to be understood that this protein is a preferred binder and that other molecules that specifically bind AA-tRNAs can be used with the same results.

Systems for following the formation of the AA-tRNA-EF-Tu:GTP complexes are an additional aspect of the present invention. A variety of ligand assay formats may be used to monitor the binding of the AA-tRNAs to EF-Tu:GTP. By immobilizing one component of the ternary complex (either the tRNA or EF-Tu:GTP) and labeling the other component, the formation of the ternary complex can be followed as the labeled molecule is 'captured' onto the surface. The EF-Tu:GTP can be immobilized to a surface and the formation of the ternary complex on the surface can be monitored by capturing labeled tRNA molecules. Alternatively, the formation of the AA-t-RNA-ligand complex can be measured in a homogeneous ligand assay. In this case, each of the 20 specific synthetases/tRNAs are positioned in separate wells, immobilized on separate beads or transported (e.g., by microfluidic pumps) through separate microchannels, depending on the physical configuration chosen for the assay. The binding of the AA-tRNA to its specific ligand (e.g.-Tu:GTP) can be monitored using an ultrasensitive homogeneous ligand assay (for example, fluorescent techniques). As mentioned above, the binding of AA-tRNAs to their ligand can be monitored in microfluidic arrays or microwells using position-sensitive detectors.

Recently, immobilized EF-Tu:GTP from *Thermus thermophilus* has been used to purify AA-tRNAs by affinity chromatography (Robeiro et al. (1995) *Anal. Biochem.* 228:330–335; Chinali et al. (1997) *Ann. Rev. Biophys. Biomol. Struct.* 26:567–596). Like the free factor, the immobilized EF-Tu:GTP binds AA-tRNAs but not unacylated tRNAs. Hence, immobilized elongation factor retains its specificity for AA-tRNAs. Accordingly, tRNAs (one specific for each amino acid) are immobilized at set locations, and the formation of the ternary complex on all 20 tRNAs is monitored simultaneously or nearly simultaneously. In this case, the ternary complexes are detected with labeled elongation factors or labeled probes that bind the ternary complex. Other ligand assay formats of the present invention employ ternary complex probes (systems that specifically recognize charged AA-tRNA-EF-Tu:GTP complexes) to capture and/or detect the ternary complex. Macromolecules that specifically recognize the ternary complex include, but are not limited to, ribosomes and ribosomal subunits (e.g., cognate mRNA-charged small ribosomal subunits). Optionally, antibodies or oligonucleotide aptamers that specifically bind the ternary complex are used.

Ultrasensitive ligand assays have relied on labeling one component of the reaction with a high-specificity-activity label (e.g., radioactive, fluorescent, or electrogenic labels) or a label that can participate in an amplification reaction (e.g., enzyme labeling). Label detection is a key determinant of sensitivity. Fluorescence is a very sensitive detection method, and laser-induced fluorescence is desirably used for sensitive amino acid detection in the present invention. Since tRNAs, elongation factors, ternary complexes or ternary complex probes can be labeled with multiple copies of fluorescent tags or with amplifying labels, one can develop ligand assays for amino acid analysis with a sensitivity many orders of magnitude greater than in commonly available methods for amino acid analysis.

Amino acid analysis can be performed with tRNA arrays of the present invention by introducing a solution of the 20 synthetases in aminoacylation buffer along with the amino acid mixture to be analyzed. The AA-tRNAs formed on an array can be detected by binding a fluorescently labeled elongation factor. Alternatively, each synthetase can be co-immobilized to a different microspot with EF-Tu:GTP to construct synthetase microarrays. Bound ternary complexes can then be detected by capturing fluorescently labeled tRNAs.

Detection of Adenosine Monophosphate (AMP)

The reaction product AMP may also be monitored and used for amino acid analysis according to the present invention. For example, the formation of AMP may be monitored in a continuous spectrophotometric assay as taught in Wu, M. X and Hill, K. A. W (1994) *Anal. Biochem.* 211:320–323).

The formation of AMP can be followed in a continuous spectrophotometric assay. (Wu, M. X. and Hill, K. A. W. (1994) *Anal. Biochem.* 211:320–323). The aminoacyl-tRNA synthetase-dependent formation of AMP is enzymatically coupled to the lactate dehydrogenase oxidation of NADH. Oxidation of NADH is monitored at 340 nm in the presence of excess coupling enzymes, ATP, and phosphoenolpyruvate. This assay is applicable to all 20 of the aminoacyl-tRNA synthetases. Multienzyme coupling assays of this type are well established in the arts and have been successfully applied to the kinetic study of a vast number of enzymes over the years (see, e.g., Oliver, I. T. (1955) *Biochem. J* 61: 116–122) and this approach allows the production of sensitive assays for following the reactions catalyzed by the aminoacyl-tRNA synthetases.

Alternatively, AMP may be detected by binding it to an AMP binding molecule (e.g., an oligonucleotide aptamer or antibody. The AMP binding molecule or AMP may be optionally labeled.

Assay Format

Any binding known in the art such as competitive, displacement, or capture assays may be employed in detecting the reaction products or ternary complex.

Binding assays may be classified into heterogeneous and homogeneous assays. Heterogeneous binding assays are those binding assays that involve physical separation, at some stage of the procedure, of a binding complex being analyzed from other components in the assay. On the other hand, homogeneous binding assays do not involve physical separation of the binding complex being analyzed. Labels may be attached to one or more members of a binding complex to facilitate detection of binding without separating the binding complex from other assay components. Both heterogeneous and homogeneous binding assays are within the scope of the subject invention.

Homogeneous binding assays for amino acid analysis are a further aspect of the subject invention. These assays include but are not limited to fluorescence resonance energy transfer (FRET) assays, fluorescence polarization assays, scintillation proximity assays, and assays based on fluorescence correlation spectroscopy. For reviews of these assay types see Sundberg, (2000) *Curr. Opin. Biotechnol.* 11: 47–53; Fernandez (1998) *Curr. Opin. Chem. Biol.* (1998) 2: 597–603; Qwicki (2000) *J. Biomol. Screen.* 5:297–306; Tetin et al. (2000) *Methods* 20: 341–61; and Van Craenenbroeck et al. (2000) *J. Mol. Recognit.* (2000) 13: 93–100.

Array Formats

Arrays permit many assays to be performed in parallel. For example, array-based biosensors are used for multianalyte sensing (see Michael K. L et al, (1998) *Anal Chem* 70: 1242–6).

The present invention provides miniaturized bioanalytical systems employing biomolecular recognition molecules and ultrasensitive detection methods that allow the analysis of multiple small samples in parallel and even in near real time. Current bioinstruments (reviewed in Cunningham, A. J. (1998) *Introduction to Bioanalytical Sensors*, John Wiley and Sons, New York) include integrated Microsystems of higher speeds.

Current methods for multianalyte analysis can be classified into two formats, assays, based on more than one label, and assays, based on spatially separated zones, for each biorecognition molecule specific for a different analyte. Biorecognition elements that recognize different analytes may be immobilized on spatially separated zones or positioned into separate chambers and the assays may be monitored simultaneously using position-sensitive detectors (for review, see Ekins, R P (1998) *Clin. Chem* 44:2015–30).

A variety of different arrays and detectors can be employed in the practice of the present invention. Arrays used in the subject invention can be biosensor, microparticle, microbead, microsphere, microspot, microwell, microfluidic arrays, and the like. The substrates for the various arrays can be fabricated from a variety of materials, including plastics, polymers, ceramics, metals, membranes, gels, glasses, silicon and silicon nitride, and the like. The arrays can be produced according to any convenient methodology known to the art. A variety of array and detector configurations and methods for their production are known to those skilled in the art and disclosed in U.S. Pat. Nos. 6,043,481; 6,043,080; 6,039,925; 6,025,129; 6,025,601; 6,023,540; 6,020,110; 6,017,496; 6,004,755; 5,976,813; 5,872,623; 5,846,708; 5,837,196; 5,807,522; 5,736,330; 5,770,151; 5,711,915; 5,708,957; 5,700,637; 5,690,894; 5,667,667; 5,633,972; 5,653,939; 5,658,734; 5,624,711, 5,599,695; 5,593,839; 5,906,723; 5,585,639; 5,584,982; 5,571,639; 5,561,071; 5,554,501; 5,534,703; 5,529,756; 5,527,681; 4,472,672; 5,436,327; 5,429,807; 5,424,186; 5,412,087; 5,405,783; 5,384,261; 5,474,796; 5,274,240; and 5,242,974. The disclosures of these-patents are incorporated by reference herein.

The arrays may be positioned into the bottom of microwells, microchannels or on the surfaces such as planar waveguides. The area of Micro-Total Analysis Systems (mu TAS), otherwise known as "Microsystems" or "Lab-on-a-chip", is used to describe miniaturized sensing devices and systems that integrate microscopic versions of the devices necessary to process chemical or biochemical samples, thereby achieving completely automated and computer controlled analysis on a microscale. Micro/miniaturized total analysis systems developed so far may be classified into two groups. One is a MEMS (Micro Electro Mechanical System), which uses pressurized flow controlled by mechanical flow control devices (e.g., microvalves, micropumps or centrifugal pumps). The other types use electrically driven liquid handling without mechanical elements. Currently, Microsystems are being produced in both academic and commercial settings. The term "microsystem" is used herein to describe both types of miniaturized systems. A variety of integrated Microsystems, MEMS, and microsystem devices are well known to the art. See, for example, U.S. Pat. Nos. 6,043,080; 6,042,710; 6,042,709; 6,036,927; 6,037,955; 6,033,544; 6,033,546; 6,016,686; 6,012,902; 6,011,252; 6,010,608; 6,010,607; 6,008,893; 6,007,775;

6,007,690; 6,004,515; 6,001,231; 6,001,229; 5,992,820; 5,989,835; 5,989,402; 5,976,336; 5,972,710; 5,972,187; 5,971,355; 5,968,745; 5,965,237; 5,965,001; 5,964,997; 5,964,995; 5,962,081; 5,958,344; 5,958,202; 5,948,684; 5,942,443; 5,939,291; 5,933,233; 5,921,687; 5,900,130; 5,887,009; 5,876,187; 5,876,675; 5,863,502; 5,858,804; 5,846,708; 5,846,396; 5,843,767; 5,750,015; 5,770,370; 5,744,366; 5,716,852; 5,705,018; 5,653,939; 5,644,395; 5,605,662; 5,603,351; 5,585,069; 5,571,680; 5,410,030; 5,376,252; 5,338,427; 5,325,170; 5,296,114; 5,274,240; 5,250,263; 5,180,480; 5,141,621; 5,132,012; 5,126,022; 5,122,248; 5,112,460; 5,110,431; 5,096,554; 5,092,973; 5,073,239; 4,909,919; 4,908,112; 4,680,201; 4,675,300; and 4,390,403, all of which are incorporated by reference herein.

Arrays useful in the present invention vary according to their transduction mechanisms and include surface acoustic wave sensors, microelectrodes, solid-state sensors, and fiber-optic sensors. However, optical, electrochemical and piezoelectric crystal arrays are preferred. These systems may be used to analyze amino acids in volumes of less than 1 microliter with a sensitivity many orders of magnitude greater than current amino acid analyzers.

It is now possible to fabricate complex miniaturized systems for total biochemical analysis. This technology represents a combination of several disciplines that include microfabrication, microfluidics, microelectronmechanical systems, chemistry, biology, and engineering. Miniaturized devices can be electrical, such as microelectrodes and signal transducers; optical such as photodiodes and optical waveguides; and mechanical, such as pumps. In the new field of microfluidics, the integration of automated microflow devices and sensors allow very precise control of ultra-small flows on microchip platforms (Gravesen et al. (1993) *J. Micromech. Microeng.* 3:168–182; Shoji and Esashi (1994) *J. Micromech. Microeng.* 4:157–171). Many different flows can be combined in all sorts of ways and mixed on the same chip. Existing technology also allows the integration of intersecting channels, reaction chambers, mixers, filters, heaters, and detectors to perform on-chip reactions in sub-nanoliter volumes in a highly controlled and automated manner with integrated data collection and analysis (Colyer et al. (1997) *Electrophoresis* 18:1733–1741; Effenhauser et al. (1997) *Electrophoresis* 12:2203–2213).

Laser-induced fluorescence is generally the detection method of choice for microarray and microflow systems. There are many examples in the literature describing single molecule detection using laser-induced fluorescence as a detection method. For example, spatially resolved detection may be achieved using confocal laser scanners or high sensitivity imaging detectors such as CCD cameras.

Microarray Formats

Microarrays or microfluidic systems of the present invention are a further aspect of the invention. These systems analyze tiny amounts of amino acid containing samples with high sensitivity. These systems advantageously offer femtomole or attomole concentration detection, which sensitivity is made possible by the use of fluorescence detectors that possess higher sensitivities than do present analyzers.

The present invention also sets forth methods of amino acid analysis based on biomolecular recognition phenomenon using small amounts or reagent and sample in microscale or nanoscale devices. The proposed methods are ultrasensitive, inexpensive and rapid. Furthermore, the methods are suitable for multiplexing to create high throughput systems. Whereas existing technology is applicable to nanomole or picomole quantities, the present methods and devices optionally allow the analysis of femtomole and attomole quantities of amino acids. The functional elements are biological molecules, and hence methods known in the art can be used to optimize the system (e.g., such known methods as directed evolution, protein and oligonucleotide engineering, phage display, antibody engineering, and combinatorial chemistry can be used to obtain biomolecules for optimum system operation). This can be accomplished using the amino acid biosensors described herein. Furthermore, the continuous amino acid analyzers described herein can be integrated with other enzymatic systems, thus creating integrated Microsystems.

The miniaturized, real time amino acid analyzers described herein can be used with exopeptidases, enzymes that remove amino acids sequentially (i.e., one at a time) from a proteins N- or C-terminus, to create integrated protein end group sequenators. These Microsystems are suitable for generating either N-or C-terminal sequence tags from intact proteins or peptides.

Generally, array technology is the method of choice for high throughput analysis. Microarrays, wherein thousands of different bioaffinity molecules are immobilized on a surface in a defined and spatially resolvable fashion (usually as spots 10–100 $\mu$m in diameter) and used to capture ligands, have been developed for both nucleic acids and proteins (Fodor et al. (1991) *Science* 251:767–773; Lueking et al. (1999) *Anal. Biochem.* 270:103–111). This microarray technology is applied in the present invention to provide amino acid analysis microchips. The 20-fold spatial distribution of the recognition elements in the microarrays of the present invention is preferably achieved by arraying either 20 specific tRNAs or the 20 specific aminoacyl-tRNA synthetases.

Techniques for detection of amino acids in the integrated Microsystems and microarrays include, but are not limited, to fluorescence emissions, optical absorbance, chemiluminescence, Raman spectroscopy, refractive index changes, acoustic wave propagation measurements, electrochemical measurement, and scintillation proximity assays. There are many demonstrations in the literature of single molecules being detected in solution using fluorescence detection. A laser is commonly used as an excitation source for ultrasensitive measurements and the fluorescence emission can be detected by a photomultiplier tube, photodiode or other light sensor. Array detectors such as charge coupled device (CCD) detectors can be used to image the analytes spatially distributed on an array.

Several microchip fluorescent detection systems are commercially available. These include the Hewlett Packard's BioChip Imager with epi-fluorescence confocal scanning laser system having a 50 micrometer, 20 micrometer, or 10 micrometer resolution. This instrument detects less than 11 molecules of the dye Cy5/square micrometer and has a dynamic range of four orders of magnitude. General Scanning's ScanArray 3000 is a scanning confocal laser with a 10 micrometer resolution that can detect 0.5 molecule of fluorescin/micrometer$^2$ (or less than 0.15 attomole of end labeled nucleotide) taking 4 minutes to scan a 10 micrometer by 10 micrometer chip. Molecular Dynamics' Avalanche confocal scanners have a resolution of 10 micrometers and can detect less than 10 molecules of Cy3 molecules/square micrometer on chips taking 5 minutes to scan the entire chip.

Methods for the spatially resolved and ultrasensitive detection of fluorescently labeled molecules in microfluidic channels are disclosed, for example, in U.S. Pat. Nos. 5,933,233 and 6,002,471. Instrumentation for the detection of single fluorescent molecules is described in U.S. Pat. No. 4,979,824 and reviewed in Sinney et al, (2000) *J Mol Recognit*, 13, 93–100; Nie, S. and Zare, R. N. (1997) *Ann.*

*Rev. Biophys. Biomol. Struc.* 26, 567–96; Rigler, R. (1995) *J Biotechnol.* 41, 177–186; Chan, W. C. and Nie, S (1998) *Science* 281, 2016–8; and Nie, S. and Emory, S. R. (1997) *Science* 275, 1102–6. CCD imagers for confocal scanning microscopes are disclosed in U.S. Pat. Nos. 5,900,949, 6,084,991, and 5,900,949. Capillary array confocal scanners are described in U.S. Pat. No. 5,274,240. CCD array detectors suitable for microchips are described in U.S. Pat. Nos. 5,846,706, and 5,653,939. Detector systems for optical waveguide microarrays are disclosed in U.S. Pat. Nos. 6,023,540, 5,919,712, 5,552,272, 5,991,048, 5,976,466, 5,815,278, 5,512,492.

Mass sensing biosensors such as piezoelectric sensors are known, for example, as disclosed in U.S. Pat. Nos. 4,236, 4,735, and 6,087,187 and are suitable for use in the present invention to construct amino acid biosensor arrays.

Microtiter Arrays

Rapid, automated and simultaneous testing of multiple samples are commonly performed in microwell formats. The microtiter plate has become a popular format for biological assays because it is easy to use, is readily integrated into an automated process and provides multiple simultaneous testing on a simple disposable device. The traditional 96-well format is being replaced with microwells with larger numbers of smaller wells. These provide plates with 192–20,000 wells with volumes that range from 125 microliters to 50 nanoliters (Reviewed in Kricka (1998) *Clinical Chemistry* 44:2008–2014). A range of new micropipetting systems based on ink-jet principles have been developed for delivery of nanoliter volumes of samples and reagents to microwells (for example, see, Rose and Lemmo (1997) *Lab Automat News:* 2:12–9; Fischer-Fruholz (1998) *American Lab*; Feb 46–51). The new high-density, low volume microwell format has been adapted for a diverse range of analytical methods. Most are simple homogeneous assays such as scintillation proximity assays, fluorescence polarization assays, time resolved fluorescence, fluorescence energy transfer, and enzyme assays.

Advantageous properties of substrates for the microarrays of the subject invention are those for substrates of traditional microarrays: ease of manufacture and processing, compatibility with detection systems, good material strength, and low nonspecific biomolecule adsorption. The substrate material should allow efficient immobilization of biomolecules either directly or through an intermediate surface coating. Glass, silicon, and plastic substrates are commonly used for microarray production and are examples of suitable substrates for use in some preferred embodiments of the subject invention. Glass has a number of favorable qualities. These include transparency, and the compatibility with radioactive and fluorescent samples. However, a variety of other materials are suitable substrates. Polypropylene also has favorable physical and chemical properties. For example, Boehringer Mannheim uses small disposable polystyrene carriers onto which microdots are deposited using inkjet technology (Ekins (1998) *Clin. Chem.* 44:2015–2030). As mentioned above, biomolecule immobilization on chips may be accomplished by various means including, but not limited to, adsorption, entrapment, and covalent attachment. Covalent attachment is the preferred method for "permanent" immobilization. Functionalized organosilanes have been used extensively as an intermediate layer for biomolecule immobilization on glass and silicon substrates. Silanes are commercially available that contain an ever-increasing number of reactive functional groups suitable for biomolecule conjugation either directly or via a cross-linker.

Microarray Printing Technologies

The microarrays of the current invention can be made using existing technologies for array construction. The microarrays of the current invention may be produced, for example, by deposition of tiny amounts of aminoacyl-tRNA synthetase or tRNA bearing solution in a predetermined pattern on a surface using arraying robots (As reviewed, for example, in Schena (ed) (2000) "Microarray Biochip Technology" Eaton Publishing, Natick, Mass.; Schena (ed) (2000) "DNA Microarrays A Practical Approach", Oxford University Press). The volume delivered is typically in the nanoliter or picoliter range.

The technologies for spotting arrayed materials onto a substrate fall into two categories: noncontact and contact dispensing. Noncontact dispensing involves the ejection of drops from a dispenser onto the surface. Contact printing involves direct contact between the printing mechanism and the solid support. For example, to construct protein or tRNA microarrays of the current invention, a high-precision contact-printing robot may be employed to deliver nanoliter volumes of proteins or tRNAs to surfaces yielding spots of about 150 to 200 micrometers in diameter.

A variety of chemically derivatized substrates can be printed and imaged by commercially available arrayers and scanners. For example, slides that have been treated with an aldehyde-containing silane reagent are commonly available (e.g., from TeleChem International, Cupertino, Calif.). The aldehydes react with primary amines on proteins or amine modified nucleic acids to form a Schiff's base linkage. Substrates for microarray construction may be coated by a protein layer and the proteins to be spotted may be attached to this protein layer using chemical crosslinking. For example, MacBeath et al (2000), supra, teach a method for spotting proteins on microarrays. The proteins are printed in phosphate-buffered saline with 40% glycerol included to prevent evaporation of the nanodroplets. They attached a layer of bovine serum albumin (BSA) to the surface of a glass substrate. Glass treated with an aldehyde-containing silane reagent readily react with amines on a protein's surface to form a covalent attachment forming a molecular layer of BSA. The BSA on the surface is then activated using a chemical cross-linking reagent (e.g., N,N'-disuccinimidyl carbonate). The activated residues on the BSA then react with residues on the printed protein to form covalent linkages. Printed proteins are displayed on top of the BSA monolayer rendering them accessible to macromolecules in solution.

Another example of a known method for microarray construction involves the in situ synthesis of unique oligonucleotides on a solid support. Proteins or other biomolecules may be attached to oligonucleotides having complimentary sequences to those positioned on the array in known locations. These oligonucleotide bearing biomolecules are then bound to the arrays in known locations by complimentary base pairing (for a review of this method, see, Niemeyer et al. (1998) *Analytical Biochem.* 268, 54–63.)

Multianalyte Testing

Simultaneous multianalyte testing is now possible, and any known method for multianalyte analysis can be used to construct amino acid analyzers employing the twenty aminoacyl tRNA synthetases and twenty specific tRNAs as recognition elements. Methods of simultaneous multianalyte testing include assays based on more than one label and assays based on spatially separated reaction zones. For example, researchers have used binders in the same assay zone labeled with different fluorescent molecules (Vuori et al. (1991) *Clin. Chem.* 7:2087–2092; Hemmila, I. (1987)

Clin. Chem. 33:2281–2283), different radioactive species (Wians et al. (1986) Clin. Chem. 32:887–890; Gutcho et al. (1977) Clin. Chem. 23:1609–1614; Gow et al. (1986) Clin. Chem. 32:2191–2194), different enzymes (Nanjee et al. (1996) Clin. Chem 42:915–926), metal ions (Hayes et al. (1994) Anal. Chem. 66:1860–1865), colored latex particles (Hadfield et al. (1987) J. Immunol. Methods 97:153–158) and particles of different sizes (Frengen et al. (1995) J. Immunol. Methods 178:141 –151). Various detection schemes employed in these multianalyte may be based on changes in one or more of the following signals: absorbance, steady-state fluorescence, fluorescence lifetime, chemiluminescence, radioactivity, electrochemical response, laser light scattering, and frequency of a piezo-electric quartz crystal, upon the binding event(s).

Methods for Labeling Nucleic Acids and Proteins and Amino Acids

The term "label" is used herein to refer to agents that are capable of providing a detectable signal, either directly or through interaction with additional members of a signal producing system. For example, labels that may be used in the subject invention include: radioactive isotopes such as $^{32}S$, $^{32}P$, $^{3}H$, etc., fluorescent labels where fluorescers of interest include, but are not limited to fluorescein (FITC, DTAF) (excitation maxima, 493 nm/emission maxima 516–525; BODIPY-FL (excitation maxima 503/emission maxima 512 nm); TRITC G (tetramethylrhodamine isothiocyanaate, isomer G (excitation maxima, 535–545 nm/emission maxima, 570–580 nm); RBITC (rhodamine-B isothiocyanate (excitation maxima, 545–560 nm/emission maxima, 585 nm); Texas Red (excitation maxima, 595 nm/emission maxima, 615–620 nm); Cy-5 (Cyanine) (excitation maxima, 649 nm/emission maxima,670 nm); Cy 3 (excitation maxima552 nm/emission maxima 565 nm; Cy-3.5 (excitation maxima 581 nm/emission maxima, 596 nm); XRITC (rhodamine X isothiocyanate (excitation maxima, 582 nm/emission maxima, 601 nm); ethidium bromide (excitation maxima, 366 nm/emission maxima, 600 nm); Thiazole orange (To-Pro) excitation maxima, 488 nm/emission maxima 530–580 nm) and others as reviewed, for example, in Haugland, R. P. (1992) Handbook of Fluorescent Probes and Research Chemicals, 5$^{th}$ ed., Molecular Porbes. Fluorescent labels are commercially available from a number of sources including Molecular Porbes, (Eugene, Oreg.) and Amersham Pharmacia Biotech (Piscataway, N.J.). Other labels can include chemiluminescent compounds, enzymes and substrates; chromogens, metals, nanoparticles, beads, microspheres, vesicles and liposomes. A vast number of labels are commercially available and can be purchased as ready-to-use reagents.

Labels may be conjugated directly to the biorecognition molecules, or to probes that bind these molecules, using conventional methods that are well known in the arts. For example, captured EF-Tu:GTP may be detected by labeling an antibody that recognizes EF-Tu:GTP and binding the EF-Tu:GTP to the antibody. In like manner, the captured AA-tRNAs may be detected using a labeled probe that binds these molecules. Such probes may be, for example, oligonucleotides or antibodies. Alternatively, the elongation factors or tRNAs may be biotinylated and avidin or streptavidin (which bind biotin) conjugated labels may be employed to detect the biotinylated molecules. These methods are commonly used in the art.

Multiple labeling schemes are known in the art and permit a plurality of binding assays to be performed simultaneously in the same reaction vesicle. Different labels may be radioactive, enzymatic, chemiluminescent, fluorescent, or others. Multiple distinguishable labels may be attached directly to biomolecules or they may be attached to surfaces onto which the biomolecules are immobilized. For example, beads or other particles may bear different labels, e.g., a combination of different fluorescent color dyes, that allow each bead to be independently identified. For example, Fulton et al, 1997, Clin. Chem. 43: 1749–1756, describe a standard set of 64 microspheres where each different type of microsphere is tagged with a unique combination of fluorescent dyes. Different biomolecules are immobilized to each microsphere type and reacted with their binders which are labeled with a different color fluorescent dye. The detector simultaneously identifies each bead type and the captured ligand based on the fluorescent profiles generated by the different colored fluorescent dyes.

Preferred detectable labels include enzymatic moieties capable of converting a substrate into a detectable product. Enzymes are amplifying labels (one label leads to many signals) and facilitate the development of ultrasensitive assays. For example, alkaline phosphatase and horseradish peroxidase are commonly used enzyme labels and attomole-zeptomole detection limits are routinely achieved in chemiluminescent assays with these enzymes. For alkaline phosphatase, the adamantly 1,2-dioxetane acrylphosphate substrates provide ultrasensitive assays (Bronstein et al. (1989) J. Biolumin. Chemilumin. 4:99–111). And for horseradish peroxidase, the 4-iodophenol-enhanced luminol reaction is among the most sensitive (Thorpe, et al, (1986) Methods Enzymol. 133:331–353). In such embodiments where an enzymatic label is used to convert a substrate into a detectable produce, the appropriate substrate is also added preferably after the binders have been captured on the surface.

Fluorescent labels are particularly useful in some embodiments of the current invention. By the use of optical techniques (e.g., confocal scanners, CCD cameras, flow cytometers), they permit the analysis of arrays of biorecognition elements distributed over a surface (e.g., as microdots where each microdot binds a different analyte) or differentially labeled (e.g., with beads having different combinations of fluorescent dyes).

The binding of molecules that specifically bind AA-tRNAs may be monitored in solution without immobilization by attaching a fluorescent label to the tRNA, the AA-tRNA binding molecule, or both. It is also possible to attach fluorescent probes to the synthetases and monitor the changes in fluoresence as synthetases bind the tRNAs and elongation complexes.

Methods for tagging or labeling proteins and nucleic acids with detectable labels are well known in the art. Radioactive and non-radioactive labels are commonly employed. For a review of enzymatic, photochemical, and chemical methods for labeling nucleic acids and proteins see Kessler (1994) J Biotechnol. 35: 165–189.

For example, reactive groups such as thiol, amine, or phosphorothioate can be introduced into nucleic acids for coupling chromophores. These methods can be applied either for the direct labeling of synthetases, elongation factors, tRNAs, ternary complexes, or for labeling of respective probes (DNA, RNA, oligonucleotides, aptamers, antibodies and the like). A label, e.g., a fluor, can be attached to the tRNAs, synthetases, elongation factors, ternary complexes or ternary probes of the subject invention provided that the ability to bind ligands is not substantially diminished.

Both tRNAs and EF-Tu:GTP have been fluorescently labeled and found to retain their binding specificities for one another (see, Johnson et al. (1982) *J. Mol. Biol.* 156:113–140; Watson et al. (1995) *Biochemistry* 34, 7904–7912).

Furthermore, biotinylated molecules e.g., synthetases, elongation factors, tRNAs, may also be labeled in a second step using avidin or streptavidin (which bind biotin) conjugated to a fluorophore or some other label. This labeling method is commonly used in the art.

There are a number of ways to label tRNAs. A label may be covalently or noncovalently attached. For example, Janiak et al. (1990) *Biochemistry* 29: 4268–4277) labeled tRNAs by attaching fluorescein covalently to the thiouridine (s4U) at position 8 which is a conserved residue (U or s4U) in all 20 tRNAs. Synthetic and enzymatic procedures allow site specific incorporation of thionucleotide(s) within RNA (reviewed in Favre et al. (1998) *J. Photochem. Photobiol. B* 42:109–124). The labeled tRNAs retained their ability to be aminoacylated by the synthetases and retained their specificity and affinities for the EF-Tu:GTP binary complexes.

In addition, tRNAs may be stained with dyes (e.g., ethidium bromide) or labeled by the hybridization of a labeled oligonucleotide probe (Buvoli et al. (2000) *RNA* 6: 912–918). tRNAs can be conveniently radiolabeled, for example, as taught in Farrel, R E, Jr. (1998), *RNA methodologies: a laboratory guide for isolation and characterization.* (Academic Press), San Diego.

Alternatively, or additionally, the elongation factor or other protein may be labeled with fluor(s). Many references can be found on modifications of various groups in proteins or peptides with fluors. These are summarized in reviews and monographs (for example, see Haugland, R. P. (1992) *Handbook of Fluorescent Probes and Research Chemicals,* 5$^{th}$ ed., Molecular Probes, (Eugene, Oreg.)). Although several groups can be used to couple a label, the thiol group is thought to be the best candidate in that many functional groups used to attach labels are thiol-specific or selective, and thus unique labeling is possible. For example, with site directed mutagenesis, a thiol group can be added to or deleted from a desired position (Cornish et al. (1994) *Proc. Natl. Acad. Sci. USA* 91: 2910–2914). Other groups on proteins surfaces commonly used for the conjugation of a label are amines (e.g., from surface lysines). Since the three-dimensional structure of the ternary complex of aminoacylated tRNA and EF-Tu:GTP has been solved (reviewed in Nissen et al. (1996) *Biochimie* 78: 921–933), the contact sites between the elongation factor:GTP and AA-tRNAs are known. From this structure, many amino acid residues on the protein's surface are identified that do not interact with the AA-tRNAs and hence are good candidates for site specific labeling.

Radiolabeled and fluorescently labeled nucleotide triphosphates are commonly used in biology and are commercially available from a number of sources.

Biomolecular recognition can also be used as a labeling method. The biomolecular recognition methods are similar to those used in biorecognition based immobilization as discussed below, except the ligand bears a label rather than being fixed to a support. For example, if a protein or nucleic acid is biotinylated, a label bearing avidin or streptavidin (or a modified form thereof) may be bound to the biotin and the biotin then is quantitated by the labeled avidin.

Alternatively, the elongation factor can be conveniently labeled with a fluorescent GTP analog. Elongation factor Tu has been labeled with fluorescent GTP analogs, and it has been found to retain its specificity and affinity for AA-tRNAs. For example, the ribose of the GTP was covalently modified with the dye rhodamine (Rh) to form GTP-Rh, and the GTP-Rh was used to label EF-Tu. The EF-Tu:GTP-Rh retained its specificity for AA-tRNAs (Watson et al. (1995) *Biochemistry* 34:7904–7912). EF-Tu:GTP-Rh may be prepared from EF-Tu;GDP by stripping the nucleotide from the protein, adding GTP-Rh to the nucleotide free EF-Tu and then purifying as described in Eccleston (1981) *Biochemistry* 20: 6265–6272. GTP has been labeled with other fluors and used to label EF-Tu (Giovane et al. (1995) Eur. *J. Biochem* 227:428–432; Eccleston et al. (1987) *Biochemistry* 26: 3902–3907). Fluorescent nucleotide analogs are commercially available (reviewed in Jameson, D. M., and Eccleston, J. F.(1997) *Methods Enzymol.* 278: 363–90).

Microflow Systems

The microsystem can be divided into two parts: the mechanical portion with the biochemistry and microfluidic pumps and the electronic portion which has the laser, detector, and the computer interface.

In one preferred embodiment, the computer interface can be approached by building a custom circuit which connects to about 20 light detectors and other input timing signals. The custom circuit would be a stand alone microprocessor which collects all of the timing and light intensity information and sends the resulting data out to a computer, for example, via a USB or serial port. The computer will be programmed for data analysis.

Because diffusion in liquids is random and slow over distances greater than a few micrometers, the incorporation of arrays into flow systems for automated processing facilitates high throughput analysis and permit sequential monitoring. Solid-phase ligand assays are currently performed in microtiter plates; however, this technique requires long incubation times to achieve equilibrium conditions and is difficult to miniaturize and automate. By contrast, flow systems are easily automated and miniaturized and allow fine control of reagent additions and rapid chemistries by reducing diffusion limitations. In addition, reproducibility is extremely high and calibrations are easy to perform (Scheller et al. (1997) *Frontiers in Biosensors.* 1. *Fundamental Aspects,* Birkhauser Verlan, Basel, Switzerland). When coupled with microdialysis and flow injection systems, biosensors have become available for on-line, real-time monitoring (Freaney et al. (1997) *Ann. Clin. Biochem.* 34:291–302; Cook, J. (1997) *Nat. Biotech.* 15:467–471; Steele and Lunte (1995) *J. Pharm. Biomed. Anal.* 13:149–154; Kaptein et al. (1997) *Biosens. Bioelectron.* 12:967–976; Nima et al. (1996) *Anal Chem.* 68:1865–1870). In one preferred embodiment, the present invention couples amino acid detecting arrays to microdialysis or miniaturized ultrafiltration systems to achieve real-time and ultrasensitive detection of amino acids as they are released into solution, for example, by carboxypeptidases or aminopeptidases.

The delivery of microliter to nanoliter volumes of samples to the arrays of the present invention can be achieved using recently developed micropipetting systems (Rose and Lammo (1997) *Automat. News* 2:12–19). Using these tools, carboxypeptidase or aminopeptidase digestions can be performed in nanowells and tiny samples (microliter or nanoliter volumes) aliquoted into amino acid analysis nanowells by, e.g., robots during the time course of the digestion. These automated systems are useful for end-group sequencing of many samples in parallel at sub picomole levels. Due to the nonlinear rate of hydrolysis by these enzymes, however, continuous assays are preferable, as explained below.

Note the microflow system may be constructed using multiple capillaries as well as multiple microchannels. In the present context, the word channel means channel or capillary. The microchannels or capillaries of the present invention can be from 1–1000 microns in diameter.

In some preferred aspects of the invention, the fluidic system allows automated calibration with known concentrations of amino acids, prewashing with equilibration buffer, incubation with the amino acids, synthetases, and elongation factors, postwashing to remove unbound material and regeneration of the sensor chip with an elution buffer all under computer control. For example, an equilibration buffer (e.g., 30 mM HEPES-KOH, pH 7.5, 10 mM $MgCl_2$, 50 mM KCl, 5 mM beta-mercaptoethanol, 1 mM ATP, 1 mM GTP is automatically perfused through the reaction channels to regenerate the binding sites. The elution buffer (e.g., 100 mM sodium borate, pH 7.5, 1 M NaCl, 10 mM $MgCl_2$, 5 mM beta-mercaptoethanol, 50 $\mu$M GTP) and washing buffers (e.g., 50 mM Tris, pH 7.5, 10 mM $MgCl_2$, 5 mM beta-mercaptoethanol, 50 $\mu$M GTP) and amino acids for calibration will be transported through the reaction channels from separate reservoirs by microfluidic pumping. Fluidic handling (volumes and flow rates of the respective solutions) and data acquisition or image acquisition (series of fluorescence images) will be synchronized by means of a computer.

Alternatively, the AA-tRNAs or other molecules that reversibly bind the elongation factors can be immobilized in the flow channels. Then the immobilized molecules are saturated with fluorescent-labeled EF-Tu:GTP. The tRNAs are immobilized in such a way that they react with EF-Tu:GTP. Since the conserved s4U residues at position 8 in tRNAs can be conjugated with fluorophores while retaining their abilities to be aminoacylated by the synthetases, and the newly formed AA-tRNAs retain their specificity to interact with EF-Tu:GTP (Johnson et al. (1982) *J. Mol. Biol.* 156:113–140; Yu, Y. T. (1999) *Methods* 18:13–21; Sontheimer, E. J. (1994) *Mol. Biol. Rep.* 20:35–44), the thiouridines (s4Us) at position 8 in the tRNAs can be used to conjugate the tRNAs to a surface using a spacer arm. Many useful nucleotide triphosphates are now available from commercial sources that can be site specifically incorporated into RNA to provide spacer arms having groups that react with heterobifunctional compounds suitable for immobilization (Hermansor, G. T. (1996) *Bioconjugate Techniques*, Academic Press, NY). These immobilized molecules retain the ability to interact with both the synthetases and elongation factors. An AA-tRNA (for example met-tRNA-met) is immobilized and saturated with fluorescently labeled EF-Tu:GTP. Newly formed AA-tRNAs created in the synthetase reaction displace a proportionate amount of an labeled elongation factor of a sufficient providing a sufficient dissociation rate for the corresponding AA-tRNA EF-TU:GTP complex. which then flows through an area illuminated by a laser beam and signal is continuously detected using a spatially specific detector, e.g., a CCD detector.

Alternatively, a ternary complex probe, a molecule that specifically binds the ternary complex, AA-tRNA-EF-Tu:GTP, is immobilized in the flow channel. Ternary complex probes include antibodies, oligonucleotides, ribosomes, ribosomal subunits, or other molecules that specifically and reversibly bind the ternary complex. For example, antibodies or nucleotide aptamers that specifically bind the ternary complex can be obtained using standard methods known in the art (Jayasena, S. D (1999) *Clin. Chem.* 45:1628–1650; Diamandis, E. P and Christopoulos, T. K (eds) (1996) *Immunoassays*, Academic Press, New York). Alternatively ribosomes or ribosomal subunits may be used. A properly programmed ribosome binds the ternary complex rapidly and tightly, and using a nonhydrolyzable GTP analog, the ternary complex dissociates from the ribosome with a dissociation rate constant of $2.7\times10^{-3}s^{-1}$ Hence, ribosomes or fragments thereof, can be used as capture probes to follow the formation of the ternary complex. Alternatively, a fluorescently labeled ternary complex having a nonhydrolyzable GTP analog can be adsorbed to the immobilized ribosome and displaced by the newly formed ternary complex. The displaced labeled ternary complex then flows past the detector. In this environment, the ternary complex probe is immobilized in the flow channel and saturated with fluorescently labeled ternary complex. Each flow channel contains a unique synthetase, its cognate tRNA and EF-Tu:GTP. These macromolecules can be continuously perfused through the amino acid specific channels, being transported from separate reservoirs using microfluidic pumping. Into each of the amino acid specific channels is pumped a different synthetase with its cognate tRNA and EF-Tu:GTP. Each reaction channel has an inlet and an outlet for amino acids to flow into and out of. As amino acids flow into the reaction channel array, the amino acids having a cognate synthetase and tRNA in each channel are converted into a proportionate amount of ternary complex which then displaces a proportionate amount of the fluorescently labeled immobilized ternary complex in the channels.

Detectors

Arrays useful in the present invention vary according to their transduction mechanisms and include surface acoustic wave sensors, microelectrodes, solid-state sensors, and fiber-optic sensors. However, optical, electrochemical and piezoelectric crystal arrays are preferred. These systems may be used to analyze amino acids in volumes of less than 1 microliter with a sensitivity many orders of magnitude greater than current analyzers.

As provided herein, a biosensor is a self-contained integrated device that is capable of providing quantitative or semi-quantitative analytical information using a biological recognition element which is in direct contact with a transduction element. For a review of real time, miniaturized sensors; see, e.g., Rogers and Mulchandani (1998) *Affinity Biosensors: Techniques and Protocols*, Humana Press, Totawa, N.J. Biosensors can be classified according to their transduction mechanisms and include microelectrodes, surface acoustic wave sensors, and fiber optic sensors. A commercially available biosensor system called BIAcore (Pharmacia Biosensor, Uppsala, Sweden) contains a sensor microchip, a laser light source emitting polarized light, an automated fluid handling system, and a diode-array position sensitive detector (Raghavan and Bjorkman (1995) *Structure* 3:331–333). This system uses a surface plasmon resonance assay, an optical technique that measures changes in the refractive index at the sensor chip surface. These systems can monitor biological interaction phenomena at surfaces in real-time under continuous flow conditions. Any of the usual energy transduction modes can be fabricated in an array format and used to construct amino acid analysis biosensor arrays. Each biorecognition element can be placed on transducers which monitor mass changes, the formation of electrochemical products, or the presence of fluorescence. Optical and electrochemical transducers, however, provide the most sensitive biosensors and are well suited for miniaturization and are thus advantageous in the practice of the present invention.

Detection systems for capillary arrays and microchannel arrays are known in the art (Huang et al. (1992) *Anal. Chem.* 64:967–72; Mathies et al. (1992) *Anal. Chem.* 64:2149–54; Kambara et al. (1993) *Nature* 361:565–566; Takahashi et al.

(1994) *Anal. Chem.* 66:1021–1026; Dovichi et al. (1994) In: *DOE Human Genome Workshop IV*, Santa Fe, N.Mex., November 13–17 Abstract #131; Wooley et al. (1994) *Proc. Natl. Acad. Sci. USA* 91:11348–52; Wooley et al. (1997) *Anal. Chem.* 69:2181–21866; Simpson et al. (1998) *Proc. Natl. Acad. Sci. USA* 95:2256–2261; Schmalzing et al. (1998) *Anal. Chem.*70:2303–10; Ueno, K. (1994) 66:1424–31; Lu et al. (1995) *Appl. Spectrosc.* 49:825–833).

In certain preferred embodiments, the microfluidic system can use side-entry laser irradiation and irradiate all the microflow channels simultaneously. Detection can be achieved with a highly sensitive camera system from a direction perpendicular to the incident laser beam. The fluorescence from the irradiated region produces a line image on the CCD detector, which may be a cooled CCD camera coupled with a cooled image intensifier and this detector is connected to a computer. The excitation light source may be a He—Ne laser. The excitation wavelength will depend on the assay type and fluorophore(s) used. The laser beam can be focused at the outlet of the parallel channels to excite the fluor(s) as they flow out of the channel array. A light emitting diode can also be used as a light source for exciting a fluorescent detectable tag. A photomultiplier tube can be used in the detection system or the excitation light source.

Any of the transducers used in biosensors can be engineered in an array format and used to monitoring the binding of AA-tRNAs to the elongation factor Tu:GTP for amino acid analysis in the subject invention. Recent developments in engineering have improved transducer piezoelectric technology, leading to a new generation of sensor devices based on planar microfabrication techniques. Piezoelectric biosensors (see, e.g., Ghidilis et al. (1998) *Biosens. Bioelectron.* 13:113–31; Suleiman et al. (1994) *Analyst* 119:2279–82; Karube et al. (1988) U.S. Pat. No. 4,786,804) are well suited to miniaturization and detect femtomole levels of analyte. In addition, labeling of the analyte is not necessary. Surface plasmon resonance biosensors are commercially available and can monitor biomolecular interactions in real time during continuous flow.

Piezoelectric biosensors and surface plasmon-based biosensors for amino acids are within the scope of detectors useful in the practice of the present invention. Piezoelectric crystals and surface plasmon resonance biosensor formats are envisaged for amino acid analysis in the subject invention. The elongation factors, synthetases, tRNAs, or ternary complex probes can be immobilized onto transducers using known methods. The biorecognition elements can be immobilized onto piezoelectric crystals for example, according to the methods of Storri et al. (1998) *Biosens. Bioelectron.* 13:347–57 and Lu H. C. et al. (2000) *Biotechnol. Prog.* 13: 347–57. Piezoelectric array biosensors have been described. (Wu, T. Z. (1999) *Biosens. Bioelectron.* 14:9–180).

In general, any object that acts as a waveguide can be engineered into an evanescent wave biosensor. Planar waveguide biosensor arrays have been described (Rowe-Taitt et al. (2000) *Anal. Biochem.* 231:123–133; Rowe et al. (1999) *Anal. Chem.* 71:3846–52; Rowe et al. (1999) *Anal Chem.* 71:433–9; Flora et al. (1999) *Analyst* 124:1455–62; Herron et al. (1999) U.S. Pat. No. 5,919,712).

Scintillation proximity assays are envisaged for amino acid analysis. In scintillation proximity assays, a radioisotope is used as an energy donor and a scintillant-coated surface (e.g., a bead) is used as an energy acceptor. Scintillation proximity assays (SPA) are described in U.S. Pat. No. 4,568,649 which is incorporated herein by reference. The elongation factor:GTP can be bound to SPA beads (commercially available from Amersham Corp., Amersham Place, Little Chalfont, England). For example, biotinylated elongation factor may be conjugated to avidin or streptavidin coated SPA beads. Biotin in the form of N-hydroxysuccinimide-biotin is available from Pierce Chemical Co., Rockford, Ill. This embodiment comprises an acceptor SPA beads and quantitation of radiolabeled AA-tRNA on a scintillation counter (for example, a microchip or microplate scintillation counter).

Microtiter plate formats using fluorescent labels and microplate fluorometers enable femtomole-attomole sensitivities. Many types of microplate fluorometers are commercially available. Molecular Device's FLIPR® microplate fluorometer or LJJ Biosystem's ACQUEST™ microplate fluorometer have the ability to handle 1536-well plates and have a high degree of automation. Bio-Tek Instruments' Model FL600 microplate fluorometer can detect less than 2 femtomoles of fluorescein with a read time of 28 sec. Molecular Device's SPECTRAMAX GEMINI® microplate fluorometer can detect 5.0 femtomoles of FITC in 96 well plates with a read time of less than 27 sec. Instruments are also available that combine time-resolved fluorescence with fluorescence resonance energy transfer pairing. This combination requires two fluorophores emitting at different wavelengths. The first emits right away, but the second is activated only when the two are in proximity, i.e., when two labeled molecules are bound. This allows simultaneous measurement of bound and unbound analytes and thus permits internal calibration. As mentioned above, it also means that the assay is homogeneous, and therefore, it is easy to automate and miniaturize.

Other detectors suitable for use in the current will depend on the label employed. The labels will be quantitatively detected in a manner appropriate to their nature, for example, by counting the radioactivity of a radioactive label or scanning a fluorescent label with a light beam. Detectors include, but are not limited to, scintillation counters, e.g., a microplate scintillation counter, gamma counters, phosphorimagers, luminometers, spectrofluorometers, spectrophotometers and others.

In addition to data acquisition with commercial microplate spectrophotometers, energy transfer assays of the subject invention can be incorporated into automated microfluidic assays for ultrasensitive and high throughput amino acid analysis (see, for example, Mere et al. (1999) *Drug Discov. Today* 4:363–369). FRET assays are also performed using commercial flow cytometers as described in Song et al. (2000) *Anal. Biochem.* 284:35–41; Burando et al. (1999) *Cytometry* 37: 21–31

Optical detection methods, especially those employing fluorescence detection, are preferred in some embodiments of the current invention. In general, a fluorescent probe is captured on the microarray, the unbound material is washed away and the fluorescence bound to each element in the microarray is visualized by fluorescence detection. Confocal scanners and CCD cameras are commonly employed for detection in microarrays and may be used in the subject invention.

Confocal scanners use laser excitation of a small region of the substrate and the entire image is obtained by moving the substrate or the confocal lens (or both) across the substrate in two dimensions. Light emitted from the fluorescent sample at each position in the microarray is separated from unwanted light by employing a series of mirrors, filters, and lenses. The light is then converted into an electronic signal with a light detector (e.g., a photomultiplier tube (PMT)).

Fluorescence imaging with a CCD camera is also employed for detection in microarrays. CCD-based imaging often employs illumination and detection of a large portion of the substrate (e.g., 1 cm$^2$) simultaneously. Filtering methods of emission spectra in CCD based systems minimize optical cross-talk between different channels. Detailed descriptions of confocal scanners and CCD imaging systems are provided in Schena (ed) (2000) *DNA Microarrays—A Practical Approach*, (Oxford University Press).

The fluorescent emission from the microarray is converted into a digital output by the detection system. The data are quantitated and interpreted. Quantitation may be accomplished by superimposing a grid over the microarray image and computing the average intensity value for each microarray element using automated software. The intensity values are then converted into amino acid concentrations by comparing the experimental and control elements.

Excitation light can be generated by a variety of sources such as lasers, arc or filament lamps, or LEDs. The excitation light is directed into the microarray sample. This can be accomplished in a number of ways. For example, a flood illumination manner, where a large area of the sample is excited at one time, may be used. Flood illumination is most often used with CCD camera type instruments. Alternatively, the excitation light may be focused to a small spot to illuminate a small portion of the sample. In some embodiments, excitation light may be transported to the microelements, which may be microchannels, using optical fibers or other waveguides.

Excitation wavelengths are chosen based on the dyes employed. For example, fluorescein isothiocyanate (FITC) is one example of a dye that may be used in the subject invention. The excitation maximum is about 493 nm and the emission maximum is about 516–525 nm. The excitation wavelength cannot be too close to the emission peak or it will pollute the fluorescence signal. For FITC, that suggests excitation wavelengths between 470–495, for example. Fluorescence measurements will use appropriate excitation/emission filter sets for each dye employed.

Biomolecules can exhibit conformation changes upon the binding of analyte which can easily be detected by a fluorescence change. Concerns about the stability of biosensors incorporating proteins can be addressed by using thermostable proteins which provide a longer life time. The development of new technologies such as polarization-based sensing and life-time based sensing which, for example, can be accomplished with light emitting diodes as a light source can provide a biosensor that are specific.

Light Collection

The fluorescent light is most often gathered or collected by an objective lens. This lens focuses on the sample and directs emitted light within some angular range into a detection path. Spatial addressing may be achieved by using a multi-element detector array, such as a CCD camera, placing light detectors in microflow channels, delivering light to microflow channels using a unique optical fiber for each channel, emission light may travel back through the same optical fiber to the detector. CCD cameras may be configured to stare at an area that has been flood illuminated. Alternatively, mechanical scanning may be employed. This can be done by scanning the light beam with mirrors, moving the sample or a combination of both.

Detectors include photomultiplier tubes, CCD cameras, and avalanche photodiodes, for example. Light detectors are also employed when using chemiluminescent labels, but an excitation source is not needed in this case.

Excitation/Emission Discrimination

In order to detect the fluorescence signal from the emission light some optical means is incorporated to separate the two types of light. Emission filters are typically placed in the emission beam before the detector. These are interference filters that pass a narrow band of wavelengths near the dye's emission peak and block all other light including the excitation light. Appropriate excitation and emission filter sets are use for each dye type.

Image analysis software to extract data from the images is essential in the microarrays of the current invention. This software preferably will identify array elements binding the fluorescent reporter, subtract background, decode multi-color images, flag or remove artifacts, verify that controls have performed properly, and normalize the signals. Database searches will be automatically performed in some cases when analyzing protein samples. Protein amino acid sequence databases will be searched to identify proteins or parts of proteins that correspond to the amino acid composition in the sample.

Fluorescence Polarization Assays

An example of a homogeneous binding assay for following the binding of AA-AMP to the aminoacyl-tRNA synthetases uses fluoresence polarization. In this assay type, a fluor-labeled ATP (or ATP analog) is employed. As the fluorescently labeled ATP is converted into AA-AMP: synthetase complexes the change in polarization is continuously monitored. The connection of the polarization with the AA-AMP;synthetase complex formation arises from the fact that Brownian motion, and consequently the magnitude of depolarization, occurring during the excitation lifetime, decreases as molecular size increases. Therefore, the conversion of a fluor-labeled ATP into the AA-AMP: Synthetase complex causes an increase in the polarization value because of the high molecular weight of the complex formed.

Fluorescence Resonance Energy Transfer (FRET) Assays

Fluorescence energy transfer is a process of energy transfer between two fluorophores, which can occur when the emission spectrum of the first fluorophore overlaps the absorption spectrum of the second fluorophore. Quenching of the emission from the first compound occurs, but the excitation energy is absorbed by the second compound, which then emits its own characteristic fluorescence. Fluorescence resonance energy transfer (FRET) assays in spatially resolved chambers (e.g., microwells or microchannels) or on differentially labeled particles are envisioned for ultrasensitive and ultra-high throughput amino acid analysis in the current invention. The assay uses two labels, one of which is fluorescent donor and the other is an energy-accepting or energy-quenching molecule (acceptor). FRET assays detect binding in real time without a washing or separation step and are easily automated and miniaturized.

There are numerous recent reviews on FRET assays and many instruments for these assays are commercially available. Measurement of energy transfer is desirably based on fluorescence detection as this can provide high sensitivity. These assays and instruments are taught in (Clegg (1995) *Curr. Opin. Biotechnology* 6:103–110; Clegg, (1996) Fluorescence Resonance Energy Transfer (FRET) In: *Fluorescence Spectroscopy and Microscopy*, Wang, X. F., Hermann, B. (eds) J. Wiley and Sons, New York; Fultron et al. (1997) *Clin. Chem.* 43:1749–1756; Selvin, (1995) *Methods Enzymol.* 246:300–334; McDade (1997) *Med. Dev. Dial. Indust.* 19:75–82; Moemer et al. (1999) *Science* 283:1670–1676; Chen et al. (1999) *Genet. Anal.* 14:157–163; Mere et al. (1999) *Drug Discov. Today* 4:363–369.

Miniaturized Fluorescence Resonance Energy Transfer Assays

Miniaturized fluorescence resonance energy transfer (FRET) assays in spatially resolved microfluidic reaction chambers and microwells are envisioned for ultrasensitive and ultra-high throughput amino acid analysis in the current invention. FRET assays detect binding in real time without a washing or separation step, are easily automated and miniaturized and ultrasensitive. Successful applications of FRET are highly promoted by the introduction of modern instruments in fluorescence detection systems. The advantages of fluorescent lifetime imaging results from the fact that fluorescence lifetimes are usually independent of the fluorophore concentration, photobleaching, and other artifacts that affect fluorescence intensity measurements (Scully et al. (1997) *Bioimaging* 5:9–18). There are many reviews available on FRET and many instruments for these assays are commercially available (Clegg, R. M. (1995) *Curr. Opin. Biotechnology* 6:103–110; Clegg, R. M. (1996) Fluorescence Resonance Energy Transfer(FRET) In: *Fluorescence Spectroscopy and Microscopy*, Wang X. F., Hermann, B. (eds) J. Wiley and Sons, New York; Fultron et al. (1997) *Clin. Chem.* 43:1749–1756; Selvin, P. R. (1995) *Methods Enzymol.* 246:300–334; McDade, R. L. (1997) *Med. Dev. Diag. Indust.* 19:75–82; Moemer et al. (1999) *Science* 283:1670–1676; Chen et al. (1999) *Genet. Anal.* 14:157–163; Mere et al. (1999) *Drug Discov. Today* 4:363–369; Nie, S. and Zare, R. (1997) *Annual Review of Biophysics and Biomolecular Structure* 26:567–96). Spatially resolved fluorescence energy transfer has the capacity to detect, quantitatively, molecular interactions in real time over distances of microns.

Measurement of energy transfer is desirably based on fluorescence detection, thus ensuring high sensitivity. In addition to data acquisition with commercial microplate spectrophotometers, energy transfer methods can be incorporated into automated microfluidic assays for ultrasensitive and ultra-high throughput analysis of biomolecular binding (Mere et al. (1999) *Drug Discov. Today* 4:363–369). The reactions catalyzed by the synthetases in the microwells can be monitored in all wells at the same time using a plate reader. Depending on the detectable tag used and the configuration, the plate reader can be a spectrophotometer, a fluorometer, a luminometer, a scintillation counter or a gamma counter.

Excitation is set at the wavelength of donor absorption, and the emission of donor is monitored. The emission wavelength of donor is selected such that no contribution from acceptor fluorescence is observed. For instance, if the tRNAs are labeled with fluorescein (fluor) and the elongation factors are labeled with rhodamine as described above, then fluorescein is the donor and rhodamine (Rh) is acceptor. Fluorescein excitation and emission wavelengths are around 490 nm and 520 nm, respectively. The labeled tRNAs are converted into AA-tRNA-Fluor by the synthetases. Both donor AA-tRNA and acceptor EF-Tu:GTP-Rh are excited by monochromic light and then fluoresce at different wavelengths. Fluorescence energy transfer between the AA-tRNA-Fluor and the EF-Tu:GTP-Rh is detected by measuring the photophysical properties of the donor fluorescence photons only. The acceptor photons may be barred from the detector by an optical filter; and therefore, the acceptor-labeled elongation factors that are not bound to the AA-tRNA-Fluor are not detected. Many donor/acceptor chromophores have been used in FRET assays and are suitable for use in the method of the present invention. For example, Wu et al. (1994) *Anal. Biochem.* 218, 1–13, lists 58 donor/acceptor pairs suitable for use in FRET assays.

A particular form of fluorescence resonance energy transfer known in the arts is homogeneous time-resolved fluorescence (HTRF) (Mathis, G. (1995) *Clin. Chem.* 41:1391–1397; Kolb et al. (1998) *Drug Discovery Today* 3:333–142). In the HTRF format, the tRNAs and elongation factors can be labeled with the europium cryptate to function as the fluorescence energy donor and the allophycocyanin acceptor, for example.

FRET assays have been extended to biosensors and microarrays (Buranda et al. (1999) *Cytometry* 37:21–31) and can be used in the microarrays and biosensors of the subject invention. FRET-based arrays are envisioned where the fluoresceinated tRNAs are converted into fluoresceinated AA-tRNA that bind rhodamine-labeled EF-Tu:GTP. Alternatively, the rhodamine, for example, TRITC, (or other acceptor) may be immobilized to a surface to which the elongation factor is bound, and the FRET may be monitored when the fluoresceinated AA-tRNA binds the surface-bound elongation factor. The surface may be a bead, microspot, or transducer. The binding of the labeled AA-tRNAs to the immobilized elongation factor brings the donor and acceptor into proximity, causing an energy transfer.

Fluorescein measurements are carried out with the excitation at or around 490 nm and emission at 520 nm. Some fluorescent labels suitable for use in the subject invention include, but are not limited to, fluorescein (FITC, DTAF) (fluorescein dichlorotriazine)) (excitation maxima, 492 nm/emission maxima 516–525 nm); carboxy fluorescein (excitation maxima, 492 nm/emission maxima, 514–518 nm; 2=-methoxy-CF (excitation maxima, 500 nm/emission maxima, 534 nm); (tetramethylrhodamine isothiocyanate, isomer G (excitation maxima, 535–545/emission maxima, 570–580); (rhodamine-B isothiocyanate (excitation maxima, 545–560/emission maxima, 585); sulforhodamine 101 sulfonyl chloride (excitation maxima, 595/emission maxima, 615–620); Cy-5™ (water-soluble cyanine dye) (excitation maxima, 649/emission maxima, 670); Cy-3.5™ (water-soluble cyanine dye) (excitation maxima 581 nm/emission maxima, 596 nm); (rhodamine X isothiocyanate (excitation maxima, 582 nm/emission maxima, 601 nm); ethidium bromide (excitation maxima, 366 nm/emission maxima 600 nm); thiazole orange (excitation maxima, 488 nm/emission maxima 530–580 nm).

The t-RNAs can be fluorescently labeled by site-specifically conjugating a fluorescent label using thiouracil as described in Johnson et al. (1982) *J. Mol.*

Biol. 156, 113–140. Fluorescently labeled nucleotide analogs can be used to site-specifically label the t-RNAs using known methods (Chu et al. (1997) *Nucl. Acids Res.* 25:3944–9). Alternatively, fluorescent dyes such as ethidium bromide can be used to label tRNAs; however, the sensitivity is relatively poor. The elongation factors may be site-specifically labeled by using a fluorescently labeled GTP analog as described above. Alternatively, the elongation factors or other proteins used in this invention can be site-specifically labeled. Molecular biology methods such as site-directed mutagenesis and unnatural amino acid mutagenesis (Anthony-Cahill et al. (1989) *Trends Biochem. Sci.* 14:400) can be used to introduce cysteine and ketone handles for specific dye labeling of proteins (Cornish et al. (1994) *Proc. Natl. Acad. Sci. USA* 91: 2910–2914).

Imaging or scanning detectors including confocal scanners, charged coupled device arrays, photodiode arrays and optical fiber arrays can be used in the subject invention as reviewed in Brignac et al. (1999) *IEEE Eng. Med. Biol. Mag.* 18:120–22; Eggers et al. (1994) *Biotechniques* 17:516–525; Pang et al. (1999) *J. Biochem. Biophys. Meth.* 41:121–132; Setford et al. (2000) *J. Chromatogr. A* 867: 93–104; Kheterpal, I. and Mathies, R. A. (1999) *Anal. Chem.* 71:31A–37A; Crabtree et al. (2000) *Electrophoresis*

21:1329–35; Heiger et al. (1994) *Electrophoresis* 15:1234–1247; and Budach et al. (1999) *Anal. Chem.* 71:3347–3355.

Methods for Immobilization of Proteins and Nucleic Acids

In some embodiments of the current invention, it will be necessary to immobilize proteins and nucleic acids. Conventional methods for protein and nucleic acid immobilization may be used in these embodiments. Proteins and nucleic acids have been immobilized in a vast number of ways over the last 30 years and many references can be found describing various immobilization techniques. Proteins and nucleic acids have been immobilized on biosensors, microarrays, microspheres, nanoparticles, and a multitude of other supports. Adsorption, entrapment, encapsulation, cross-linking and covalent attachment are among the techniques employed for immobilization of biomolecules. Proteins and nucleic acids may be encapsulated by enveloping the molecules in various forms of semipermeable membranes, entrapped in gel lattices, adsorbed onto or covalently attached to surfaces. For example, proteins and nucleic acids may be entrapped in gels along with fluorescent or other indicators (Flora and Brennan (1999) *Analyst* 124:1455–1462). These biomolecules may be encapsulated into sol-gel derived materials prepared either as monoliths or beads. A support-free type of immobilization is crosslinking. This method involves joining of proteins to each other to form three-dimensional complex structures. Chemical methods for crosslinking normally involve covalent bond formation between the proteins by means of a bi-or multi-functional reagent, such as glutaraldehyde. Strategies for reversible immobilization of proteins include reversible chemical interactions (Tyagi, et al. (1994) *Biotechnol. Appl. Biochem.* 20:93–99) in particular metal chelation (Gritsch et al. (1995) *Biosens. Bioelectron.* 10: 805–812) or disulfide cleavage (Batistaviera et al. (1991) *Appl. Biochem. Biotech.* 31: 175–195), protein-ligand interactions (Phelps et al. (1995) *Biotechnol. Bioeng. 46, 514–524*) and nucleic acid hybridization (Niemeyer et al. (1994) *Nucleic Acids Res.* 22: 5530–5539).

Methods for site-selective immobilization of biomolecules on surfaces have been developed. This will facilitate the fabrication of spatially defined ligand-receptor arrays for biosensors and parallel-ligand binding assays on microarrays. For example, immobilization of immunoglobulins was achieved by photolithography techniques (Rozsnyai, et al. (1992) *Angew Chem. Int. Ed. Engl* 31, 759).

Nucleic acid-directed immobilization of proteins provides a single site-selective process for the immobilization of proteins and other biomolecules under mild chemical conditions (Niemeyer et al. (1998) *Anal. Biochem.* 268, 54–63). Oligonucleotide arrays are widely used for DNA analysis (e.g., Kozal et al. (1996) *Nat. Med.* 2: 753–759) and such arrays are used as standard array templates for the constructing of arrays of any biomolecule that can be attached to a single stranded nucleic acid. The single stranded nucleic acid is then hybridized to its complimentary strand immobilized in a known location on a surface. This method of arraying proteins and nucleic acids may be employed in some embodiments of the subject invention.

Other methods for immobilizing functionally active proteins on microarrays are known. For example, Arenkov et al. (2000) *Anal. Biochem.* 278: 123 teach methods of arraying functionally active proteins using microfabricated polyacrylamide gel pads. And MacBeath et al. (2000) *Science* 289: 1760–1763 teach methods for spotting proteins onto chemically derivatized glass slides at high spatial densities. A high-precision robot was used to spot proteins onto chemically derivatized slides at high spatial densities. The proteins are attached covalently to the slide surface, yet retain their ability to interact specifically with other proteins or small molecules.

Protein or nucleic arrays of the subject invention may be created using any of the known microarray methods as reviewed in Schena et al. (ed) *DNA Microarrays A Practical Approach*, Oxford University Press;

Methods used for immobilizing proteins or nucleic acids are described in the following references, and others (Mosbach (1976) *Meth. Enzymol.* 44:2015–2030; Hermanson, G. T. (1996) *Bioconjugate Techniques*, Academic Press, NY; Bickerstaff, G. (ed) (1997) *Immobilization of Enzymes and Cells*, Humana Press, NJ; Cass and Ligler (eds.) (1998) *Immobilized Biomolecules in Analysis*, Oxford University Press; Watson et al. (1998) *Curr. Opin. Biotech.* 609:614; Ekins (1998) *Clin. Chem.* 44:2105–2030; Roda et al. (2000) *Biotechniques* 28: 492–496; Wong (1993) *Chemistry of Protein Conjugation and Cross-linking* CRC Boca Raton, Fla.; Taylor, (1991) *Protein Immobilization: fundamentals and applications* Marcel Dekker, Inc New York; Hutchens (ed) (1989) *Protein recognition of immobilized ligands*, Vol 83 Alan R Liss, Inc; Sleytr U. B. (ed) (1993) *Immobilized macromolecules, application potentials* Vol 51. Springer series in applied biology, SpringerVerlag, London; Wilchek and Bayer (eds) (1990) *Avidin-Biotin Technology*. Academic Press, San Diego; Ghosh et al. (1987) *Nucleic Acids Res.* 15: 5353–5372; Burgener et al. (2000) *Bioconjug. Chem.* 11: 749–754; Steel et al. (2000) *Biophys J* 79:975–981; Afanassiev et al. (2000) *Nucleic Acids Res.* 28: E66; Roda et al. (2000) *Biotechniques* 28: 492–496; Shena (ed.) (2000) *DNA Microarrays, a practical approach* (Oxford University Press); Schena (ed.) (2000) *Microarray Biochip Technology*. (Eaton Publishing Natick, Mass.); MacBeath et al. (2000) *Science* 289:1760–1763; Schena et al. (1998) *Trends in Biotechnol.* 16: 301–306; and Ramsey (1998) *Nat. Biotechnol.* 16: 40–44; all of which are incorporated by reference herein.

Proteins and nucleic acids have been immobilized onto solid supports in many ways. Methods used for immobilizing proteins and nucleic acids are described in the following references, and others (Mosbach (1976) *Meth. Enzymol.* 44:2015–2030; Weetall (1975) *Immobilized Enzymes, Antigens, Antibodies and Peptides*; Hermanson, G. T. (1996) *Bioconjugate Techniques* (Academic Press, NY); Bickerstaff, G. (ed.) (1997) *Immobilization of Enzymes and Cells* (Humana Press, NJ); Cass and Ligler (eds.) *Immobilized Biomolecules in Analysis*, (Oxford University Press); Watson et al. (1990) *Curr. Opin. Biotech.* 609:614; Ekins, R. P. (1998) *Clin. Chem.* 44:2105–2030; Roda et al. (2000) *Biotechniques* 28:492–496; Schena et al. (1998) *Trends in Biotechnol.* 16:301–306; Ramsay, G. (1998) *Nat. Biotechnol.* 16:40–44; Sabanayagam et al. (2000) *Nucl. Acids Res.* 28:E33; U.S. Pat. No. 5,700,637 (Southern, 1997); U.S. Pat. No. 5,736,330 (Fulton, 1998); U.S. Pat. No. 5,770,151 (Roach and Jonston, 1998); U.S. Pat. No. 5,474,796 (Brenman, 1995); U.S. Pat. No. 5,667,667 (Southern, 1997); all of which are incorporated by reference herein).

Many coupling agents are known in the art and can be used to immobilize biomolecules in the current invention. Over 300 cross-linkers are currently available. These reagents are commercially available (e.g., from Pierce Chemical Company (Rockford, Ill.). A cross-linker is a molecule which has two reactive groups with which to covalently attach a protein, nucleic acids or other molecules. In between the reactive groups is typically a spacer group. Steric interference with the activity of the biomolecule by the surface may be ameliorated by altering the spacer composition or length. There are two groups of cross-linkers, homobifunctional and heterobifunctioal. In the case of heterobifunctional crosslinkers, the reactive groups have dissimilar functionalities of different specificies. On the other hand, homobifunctional cross linkers' reactive groups are the same. A through review of cross-linking can be found in Wong, 1993, *Chemistry of Protein Conjugation and Cross-linking*, CRC Press, Boca Raton. Bifunctional cross-linking reagents may be classified on the basis of the following (Pierce Chemical Co. 1994): functional groups and chemical specificity, length of cross-bridge, whether the cross-linking functional groups are similar (homobifunctional) or different (heterobifunctional), whether the functional groups react chemically or photochemically, whether the reagent is cleavable, and whether the reagent can be radiolabeled or tagged with another label.

When macromolecular ligands are used, the biomolecules should be immobilized in such a way as to reduce steric hindrances generated by the support. A variety of methods for achieving this are known in the art. For example, the active site or other binding region of the biomolecule can be orientated away from the surface (Reviewed in Bickerstaff, (ed.) (1997) *Immobilization of Enzymes and Cells*, pp. 261–275).

When it is necessary to reduce steric problems of an immobilized biomolecule (e.g., aminoacyl-tRNA synthetase, elongation factor, tRNA, as in some of the preferred embodiments of the current invention, a suitable spacer arm may optionally be used to immobilize the biomolecule to a surface. Suitable spacer arms may include, but are not limited to, carbon spacers, poly ethylene glycol polymers, peptides, dextrans, proteins, and nucleic acids. For example, Maskos et al. (1992) teach methods of immobilizing oligonucleotides to chips.

Afinity biosensors are especially useful in practicing the present invention. (See, Rogers and Mulchandani (1998) *Affinity Biosensors* (Human Press, Totoaw, N.J.).

Other methods of protein immobilization suitable for immobilizing proteins in the subject invention involve immobilization via a fusion tail. Fusion proteins are commonly constructed having fusion tail systems to promote efficient recovery, purification, and immobilization of recombinant proteins (reviewed in Ford, et al. (1991) *Protein Expr. Purif.* 2: 95–107). A target protein is genetically engineered to contain a C- or N-terminal polypeptide tail, which may act as a spacer arm and provides the biochemical basis for specificity in purification and/or immobilization. Tails with a variety of characteristics have been used. Examples include entire proteins or protein domains with affinity for immobilized ligands, a biotin-binding domain for in vivo biotination promoting affinity of the fusion protein to avidin or streptavidin, peptide binding proteins with affinity to immunoglobulin G or albumin, carbohydrate-binding proteins or domains, antigenic epitopes with affinities for monoclonal antibodies, charged amino acids for use in charge-based recovery methods, poly(His) residues for recovery by immobilized metal affinity chromatography. For example, Ribeiro et al. (1995) *Anal. Biochem.* 228, 330–335, genetically engineered elongation factor Tu from *Thermus thermophilus* creating a protein having a spacer of nine amino acids followed by six histidine residues on its C-terminus. This protein was immobilized on Ni(2+)-nitriloacetic acid agarose and used to affinity purify aminoacyl-tRNA. Importantly, the immobilized protein retained its affinity and specificity for AA-tRNAs.

In some embodiments of the current invention, tRNAs are immobilized to surfaces (e.g., beads, microspheres, the bottoms of microwells, microchannels, optical fibers or other biosensor transducers). The tRNAs may be immobilized by covalent or noncovalent attachment. These molecules may be immobilized, for example, using chemical cross-linkers to covalently attach them to a surface, by adsorption, entrapment, encapsulation, or by binding to a protein, nucleic acid, or peptide nucleic acid. For example, the tRNAs may be immobilized by electrostatic binding to molecules such as poly-L-lysine. Furthermore, the tRNAs may optionally be cross-linked to a suitable spacer arm and attached to a solid support. Biotinylated tRNAs may be immobilized by binding to avidin or streptavidin. The chemical modification can encompass several strategies. The initial derivatization may be to add a spacer arm to a particular reactive group. The spacer may optionally contain a terminal functional group that can be used to couple to another molecule or to a surface. Chemical modification, cross-linking, and immobilization of nucleic acids are taught in a number of references. For example, see, Hermanson (ed) (1996) *Bioconjugation Techniques* pp 639–671. The spacer arm is preferably long enough to eliminate most steric hindrance caused by the solid surface to ensure the efficiency of the interaction with the cognate aminoacyl-tRNA synthetase and the interaction of EF-Tu:GTP with the AA-tRNA formed on the immobilized tRNA by the synthetase. Additionally, the spacer arm should permit no nonspecific binding of the labeled probe (e.g., labeled EF-Tu:GTP). For example, using nucleic acids as spacers, Shchepinov et al. (1997) *Nucleic Acids Research*. 25: 1155–1161, have demonstrated that an optimal spacer length is at least 40 atoms long and can increase the hybridization yields of nucleic acids by 150 fold.

For optical biosensors solid supports such as fused silica and quartz are appropriate substrates for immobilization. Adsorption, entrapment and covalent attachment are among the techniques employed for immobilization of biomolecules onto solid supports.

Electrochemical-based enzyme immobilization methods are convenient for enzymes on microelectrodes; however, this method is restricted to use with amperometric sensors. This method allows each enzyme or nucleic acid to be located at one electrode (the working electrode). There are several situations in which conventional crosslinking based immobilization is inadequate in the construction of microelectrodes, for example, when on-wafer deposition (i.e., immobilization on the whole wafer before it is cut into smaller segments for use in individual devices) is required, leading to many localized immobilizations or during fabrication of multianalyte sensors requiring several distinct membrane sensors. The three main types of immobilization developed to overcome these problems are based on photochemistry, electrochemistry and printing (see, e.g., Bickerstaff, G. F. (ed.) (1997) supra).

The proteins can be adsorbed, embedded or entrapped or covalently linked to surfaces. The proteins can be adsorbed or attached to nanoparticles, for example, and these nanoparticles can be position in microflow channels. The nanoparticles can be held in position using magnetic nanoparticles and magnetic force or by a filter, grid or other support. Alternatively, the proteins can be adsorbed or covalently attached to the surfaces within the microflow channels or wells.

The biomolecules can be immobilized on the surfaces within the microflow channels, wells or membranes, or the biomolecules can be immobilized onto the surfaces of beads, membranes or transducers or other surfaces placed in the flow channels, chambers or wells. Suitable beads for immobilization of proteins or nucleic acids (especially tRNAs) include chemically or physically crosslinked gels and porous or nonporous resins such as polymeric or silica based resins. Suitable media for adsorption include, without limitation, ions exchange resins, hydrophobic interaction compounds, sulfhydryls and inherently active surfaces and molecules such as plastics or activated plastics, aromatic dye compounds, antibodies, antibody fragments, aptamers, oligonucleotides, metals or peptides. Examples of some suitable commercially available, polymeric supports include, but are not limited to, polyvinyl, polyacrylic and polymethacrylate resins. Steric hindrance arising from these supports should be minimal. Free sulfliydryls are used in site-specific conjugation of proteins and nucleic acids to surfaces and labels.

Many coupling agents are known in the art and can be used to immobilize biomolecules in the methods and devices of the present invention. Coupling agents are exemplified by bifunctional crosslinking reagents, i.e., those which contain two reactive groups which may be separated or tethered by a spacer. These reactive ends can be of any of a number of functionalities including, without limitation, amino reactive ends such as N-hydroxysuccinamide, active esters, imidoesters, aldehydes, epoxides, sulfonyl halides, isocyanate, isothiocyanate, nitroaryl halides, and thiol reactive ends such as pyridyl disulfide, maleimides, thiophthalimides and active halogens.

Enzymes with quaternary structure include the aminoacyl tRNA synthetases used in the present invention. These enzymes can undergo inactivation by dissociation of subunits and stabilization of these enzymes can be achieved by crosslinking the subunits as taught, for example, in Torchilin et al. (1983) *J. Molec. Catalysis* 19:291–301.

Another method of immobilizing proteins uses proteins with N- or C-terminal spacers or tethers. The immobilized reagent or factor is a specific biomolecular recognition reagent, e.g., synthetase, tRNA, elongation factor or probe and is attached covalently or noncovalently on a surface. This can be used to form a capture site. In preferred embodiments, the immobilized reagent can be chosen to directly bind the analyte (e.g., the amino acid(s)) or indirectly bind the analyte by means of an ancillary specific binding member that is bound to the analyte. The immobilized reagent can be immobilized on the structure before or during the performance of the assay by means of a suitable attachment method.

When macromolecular ligands are used, the biomolecules preferably are immobilized in such a way as to reduce steric hindrances generated by the support. A variety of methods for achieving this are known in the art. For example, the active site or other binding region of the biomolecule can be orientated away from the surface (Reviewed in Bickerstaff, G F (ed.) *Immobilization of Enzymes and Cells*, pp 261–275).

When it is necessary to reduce steric problems or an immobilized biomolecule reacting with a macromolecule, as in some of the preferred embodiments of the current invention, a suitable spacer arm is used to immobilize the biomolecule to a surface. The spacer arm distances the biomolecule from the support surface. The spacer arm should be long enough to promote efficient separation of the biomolecule from the support; the spacer arm should be very flexible to provide high mobility to the immobilized biomolecule, thereby allowinh maximum interaction with the macromolecule ligand. Suitable spacer arms include, but are not limited to, dextrans, particularly those oxidized by periodate, polypeptides, protein, nucleic acids, and peptide nucleic acids.

Printing methods for making microarrays in the current art can be used to deliver nucleic acid or proteins to surfaces in predetermined locations. For example, aminophenyl-trimethoxysilane treated glass surfaces can bind 5' amino-modified oligonucleotides nucleic acids using a homo bifunctional crosslinker to attach the aminated oligonucleotide to the aminated glass as taught in Guo et al. (1994) *Nucleic Acids Research* 22:5456–5465. Another known method for arraying nucleic acids is to react the nucleic acid with succinic anhydride and attach the resulting carboxylate group via an ethyldimethylaminopropylcarbodiimide-mediated coupling reaction (Joos et al. (1997) *Anal. Biochem.* 247: 96–101). In another method 5' phosphate modified nucleic acids react with imidazole to produce a 5'-phosphoimidazolide that can bind to surface amino groups via a phosphoramidate linkage (Chu et al. (1983) *Nucleic Acids Research* 11:6513–6529). The linker is preferably long enough to eliminate much of the steric hindrance caused by the solid surface to ensure efficiency of the following binding reactions. For example, Shchepinov et al. (1997) *Nucleic Acids Research* 25:1155–1161, reported that an optimal spacer length is at least 40 atoms long will increase binding yields by 150-fold in nucleic acid hybridization experiments on microarrays.

Over the past two decades, the avidin-biotin system has been developed for the immobilization of proteins and nucleic acids. For a review, see, Wilchek, M, and Bauer E A (ed) *Avidin-Biotin Technology* (Academic Press, San Diego, Calif.). Proteins or nucleic acids can be immobilized using avidin-biotin technology where a biotin labeled molecule can be bound irreversibly to avidin, which is attached to the solid support. The extraordinary affinity of avidin (or its bacterial relative streptavidin) for biotin forms the basis of this system. Since avidin, streptavidin, their analogues, and their derivatives are very stable, their immobilization is usually advantageous compared to other proteins. Because one avidin molecule can bind four biotin molecules, it is possible to co-immobilize each synthetase and elongation factor Tu:GTP using avidin-biotin technology. In this embodiment of the invention, the synthetases and elongation factor are attached to long flexible biotinylated spacer arms. The spacer arm can be a commercially available polymer such as dextran, a polypeptide, a nucleic acid, or some other tether. The streptavidin (or avidin or a derivative thereof) bearing the co-immobilized synthetase and elongation factor can be immobilized as a microspot in a microarray. This can be accomplished, for example, by binding a biotinylated oligonucleotide or nucleic acid probe having a unique sequence to each of the 20 synthetase-elongation factor pairs co-immobilized using avidin molecules. A nucleic acid or oligonucleotide probe having a sequence complementary to each of the 20 synthetase-elongation factor-oligonucleotide conjugates can be arrayed onto a surface in known positions. In this way, each of the 20 synthetases is immobilized to the surface in known positions as the nucleic acid (or probe nucleic acid) conjugated to avidin molecules binds its complementary sequence by Watson-Crick base pairing.

In another embodiment, the synthetase-elongation factor-avidin molecule can be conjugated to a different biotinylated peptide or peptide bearing a strep-tag sequence. The strept-tag constitutes a nine amino acid-peptide that specifically binds to streptavidin occupying the same binding site where biotin normally binds. Streptavidin tag fusion proteins can be constructed and used to immobilize proteins to streptavidin. Any affinity tag sequences, such as hexahistidine for metal chelate immobilization and epitope sequence for specific binding by an immobilized antibody, can be used. In one embodiment of the subject microarray, 20 different epitope sequences and 20 different antibodies, one that specifically binds each epitope sequence is used to array the biorecognition molecules. These conjugates are thereby arrayed onto surfaces bearing 20 different antibodies, one specific for a unique epitope on each peptide on the 20 synthetase-elongation factor-avidin conjugates. The antibodies may be arrayed to the surface using any of the microarray technologies known in the art.

Recombinant DNA methodologies are commonly used to generate fusion proteins having N-terminal or C-terminal extensions that provide either a tether or spacer arm and binding sites for the immobilization of proteins. Such methods will be suitable for the immobilization of proteins and nucleic acids in the subject invention. Examples of these methods are given in the following references: Nilsson et al. (1997) *Protein Expr. Purif.* 11:1–16; Shpigel et al. (1999) *Biotechnol. Bioeng.* 65:17–23; Kroger et al. (1999) *Biosens. Bioelectron.* 14:155–161; Piervincenzi et al. (1998) *Biosens. Bioelectron.* 13:305–312; Airenne et al. (1999) *Biomol. Eng.* 16:87–92; Skerra, A. and Schmidt, T. G. (1999) *Biomol. Eng.* 16:151–156; and Jones et al. (1995) *J. Chromatogr.* A, 707, 3–22.

In methods for the immobilization of the synthetases, tRNAs, or elongation factor, a spacer arm or tether is preferred. Elongation factor Tu from *Thermus thermophilus* containing six histidine residues on its C-terminus has been immobilized on $Ni^{2+}$-nitriloacetic acid agarose and used to affinity purify aminoacyl-tRNA (Ribeiro et al. (1995) *Anal. Biochem.* 228:330–335). Importantly, the immobilized EF-Tu:GTP does not lose its affinity for AA-tRNAs.

For t-RNA arrays the 20 different t-RNAs can be immobilized by covalent or noncovalent attachment. The t-RNAs may be arrayed by electrostatic binding to basic molecules such as poly-L-lysine, poly-L-arginine, protamine or other basic proteins or polypeptides. Immobilization of nucleic acids on microarrays by electrostatic binding to immobilized poly-L-lysine has resulted in the detection of mRNA species present at a ratio of 1:100,000 (DeRisi et al. (1997) *Science* 278:680–686). Alternatively t-RNAs can be bound to complementary sequences of single stranded nucleic acids or to RNA binding proteins. Oligonucleotides can be synthesized directly on the surfaces of chips, or can be pre-synthesized and then deposited onto the chips. tRNAs can bind to these arrayed nucleotides by complementary base pairing. Controlled electric fields have been used to immobilize nucleic acids on microelectrodes (Sosnowski et al. (1997) *Proc. Natl. Acad. Sci. USA* 94:111–1123).

Other Differential Detection Methods

Amino acid analysis based on biomolecular recognition employing multiple labels for the analysis of multiple amino acids in a sample is a further aspect of the current invention. By using multiple distinguishable labels, multiple discrete binding assays are performed in a single vessel at the same time. Multiple labels may be different fluorescent dyes, different radioisotopes, different dye or isotope ratios, different size particles, etc. The labels may be attached directly to the molecular recognition elements. Alternatively, the labels may be attached to a surface to which the molecular recognition elements are immobilized. Labels may be attached to proteins, nucleic acids, or other polymers for example. In some preferred embodiments of the current invention, uniquely distinguishable particles (e.g., microspheres, nanoparticles, metals, liposomes, vesicles, beads, proteins and the like) serve as labels for the amino acid-specific agents (e.g., aminoacyl tRNA synthetases and/or tRNAs).

One known method for quantitative and simultaneous detection of multiple analytes in a sample is a flow microsphere binding assay (Reviewed in McHugh, 1994, *Methods in Cell Biology* 42: 575–595). This technique relies upon the ability of a flow cytometer to accurately detect different classes of microspheres based upon a physical characteristic such as size or color. The different microsphere classes are coated with different capture reagents and the fluorescence associated with each microsphere is quantitated with a flow cytometer.

For example, Luminex (Austin, Tex.) describe a method for encoding microspheres according to their fluorescence as taught in Fulton et al, 1997, *Clin. Chem.* 43:1749–1756 and U.S. Pat. No. 5,736,330 both of which are incorporated herein by reference. The methodology is based on the principle that fluorescent microspheres (beads) with unique fluorescent profiles can be immobilized to different analyte specific binders and used to create a fluorescence-based array of analyte specific beads where each bead type is specific for a unique analyte. This technology employs a combination of fluorescent dyes that allow each bead to be independently identified. The analyte specific microspheres are mixed together and contacted with a probe(s) that is labeled with a different fluorescent color. The probes bind to their ligands or receptors on the labeled microspheres and are used to determine the specific molecular interaction at the surface of each bead. The samples are read in a flow cytometer which allows each microsphere to be identified individually and the corresponding probe binding signal to be read. This technology has the potential to be faster, less expensive, and more sensitive than microarrays based on spatial separation.

The microspheres are available (Luminex, Austin, Tex.) in 64 distinct sets that are classified by virtue of the unique orange/red emission profile of each set. Different concentrations of each of two fluorochromes, orange-emitting and red-emitting, were used to prepare 64 microsphere sets with unique orange/red emission profiles. The microspheres can be covalently coupled to virtually any amine-containing molecule through surface carboxylate groups. Alternatively, avidin-coupled microspheres are available for immobilizing biotinylated molecules (Fulton et al, 1997, *Clin. Chem.* 43: 1749–1756).

The FLOWMETRIX™ flow microfluorimetry system (Luminex Corp.) performs analysis of up to 64 different assays by using a flow cytometer. The flow cytometer analyzes individual microspheres by size and fluorescence. In this system three fluorescent colors, orange (585 nm), red (>650 nm) and green (530 nm), are simultaneously distinguished by the flow cytometer. Microsphere classification is determined by the orange and red florescence, whereas green fluorescence is used for labeling the probes. As each microsphere is analyzed by the detector, the microsphere is classified into its distinct analyte specific set (from the orange and red fluorescence) while simultaneously the green fluorescence on each bead is recorded. From this data, the identity and quantity of the multiple analytes are automatically determined. This technology has the potential to be faster, cheaper, and more sensitive than other array formats. For example, 512 different assays can be analyzed in a single well in a few seconds (Chandler et al, 1998, *Cytometry* suppl 9:40).

Michael et al., (1998) *Anal. Chem.* 70:1242–1248 teach a method of multianalyte analysis where mixtures of different microspheres, each a different assay, are applied to an optical sensor array for detection. Single microspheres immobilized in wells etched from optical fiber bundles have the potential for array elements to be in the submicrometer size range. Each different microsphere is tagged with a unique combination of fluorescent dyes. This optical labeling technique is simply a combination of fluorescent dyes with different excitation and emission wavelengths and intensities that allow each bead to be independently identified. This type of labeling is similar to that used by Luminex in its multiplexed flow cytometer arrays. The optically labeled arrays can be decoded in a matter of seconds with conventional image processing software by collecting a series of fluorescent images at different excitation and emission intensities of each unique bead. Excitation light is launched into the fiber. Light emitted form the fluorescent dyes on the fiber's distal tip is carried back along the fiber and filtered before image capture on a CCD camera. Optical fiber arrays offer rapid, multiplexed, and sensitive detection(absolute detection limits of zeptomole, $10^{-21}$ moles of DNA. See, Walt (2000) *Science* 287: 451–452); and Walt et al U.S. Pat. No. 6,023, 540 which are each herein incorporated by reference.

Bead assays have recently become popular, for example, for gene expression analysis by massively paralleled signature sequencing on microbead arrays, see Brenner et al. (2000) *Nature Biotechnology* 18: 630–634; surface plasmon resonance binding assays, Lyon et al. (1998) *Anal. Chem.* 70: 5177; DNA colorimetric nanoparticle assay, Storhoff et al. (1998) *J. Am. Chem. Soc.* 120, 1959, and solution based DNA hybridization, Elghanian et al. (1997) *Science* 277: 1078.

Other detection schemes based on differential labeling for amino acid analysis are a further aspect of this invention. These assays can be incorporated into methods of the current art employing differential labeling and label specific detectors as discussed above. In these arrays, amino acid-specific agents such aminoacyl tRNA synthetases or tRNAs are attached to individual labels (e.g., microbeads) which may be distinguished by a detector. These labeled elements may be distributed randomly on a surface or maintained in the form of a suspension.

The microarrays, microsystems, or kits of the present invention can be readily incorporated into the technologies of the current art. The proteins and nucleic acids of the subject invention may be immobilized in any number of ways. The methods for array construction or biomolecule immobilization are not important in the subject invention, as a vast number of methods known in the art are suitable.

The development of these miniaturized array-based systems improves the throughput and sensitivity of amino acid analysis and protein end-group sequencing by orders of magnitude and allow proteins, like DNA and RNA, to be subjected to mass screening.

Antibody Techniques

Monoclonal or polyclonal antibodies, preferably monoclonal, specifically reacting with a particular protein or epitope of interest, such as an AA-tRNA-EF:Tu-GTP complex may be made by methods known in the art. See, e.g., Harlow and Lane (1988) *Antibodies: A Laboratory Manual*, Cold Spring Harbor Laboratories; Goding (1986) *Monoclonal Antibodies: Principles and Practice*, 2d ed., Academic Press, New York; and Ausubel et al. (1992) *Current Protocols in Molecular Biology*, Green Wiley Interscience, New York, N.Y.

DNA Technology

Standard techniques for cloning, DNA isolation, amplification and purification, for enzymatic reactions involving DNA ligase, DNA polymerase, restriction endonucleases and the like, and various separation techniques are those known and commonly employed by those skilled in the art.

A number of standard techniques are described in Sambrook et al. (1989) *Molecular Cloning*, Second Edition, Cold Spring Harbor Laboratory, Plainview, N.Y.; Maniatis et al. (1982) *Molecular Cloning*, Cold Spring Harbor Laboratory, Plainview, N.Y.; Wu (ed.) (1993) *Meth. Enzymol.* 218, Part In; Wu (ed.) (1979) *Meth. Enzymol.* 68; Wu et al. (eds.) (1983) *Meth. Enzymol.* 100 and 101; Grossman and Moldave (eds.) *Meth. Enzymol.* 65; Miller (ed.) (1972) *Experiments in Molecular Genetics*, Cold Spring Harbor Laboratory, Cold Spring Harbor, N.Y.; Old and Primrose (1981) *Principles of Gene Manipulation*, University of California Press, Berkeley; Schleif and Wensink (1982) *Practical Methods in Molecular Biology*; Glover (ed.) (1985) *DNA Cloning Vol.* In and II, IRL Press, Oxford, UK; Hames and Higgins (eds.) (1985) *Nucleic Acid Hybridization*, IRL Press, Oxford, UK; Setlow and Hollaender (1979) *Genetic Engineering: Principles and Methods*, Vols. 1–4, Plenum Press, New York; and Ausubel et al. (1992) *Current Protocols in Molecular Biology*, Greene/Wiley Interscience, New York, N.Y. Abbreviations and nomenclature, where employed, are deemed standard in the field and commonly used in professional journals such as those cited herein.

Protein Endgroup Sequencing

In a preferred embodiment, the invention couples an amino acid analysis device to enzyme reactions that release amino acids, one at a time, from the N-terminus (using aminopeptidases) or more importantly from the C terminus (carboxypeptidases) for protein and peptide end group sequencing.

The systems invented herein make possible continuous Microsystems for amino acid analysis. In one of its aspects, the invention provides integrated continuous amino acid analysis microarrays and Microsystems that can detect amino acids continuously in the order that they are released by these enzymes. These miniaturized amino acid detectors can be integrated with aminopeptidase and carboxypeptidase digestions creating ultrasensitive, on-line microfluidic systems capable of generating either N- or C-terminal sequence data using minute protein samples. As the amino acids are liberated by these enzymes, they flow from the site through amino acid analysis microfluidic arrays and are detected continuously in the order that they are released. The terminal sequence is then regenerated by a computer from the record of the amino acid detection.

An additional aspect of the present invention are methods of end-group analysis of proteins and polypeptides. Proteins that are N-terminally blocked present a challenge because they cannot be directly sequenced by Edman degradation. A blocked N-terminus is common (approximately 80–90% or eukaryotic proteins are N-terminally blocked), while C-terminal blocking is rare. One advantage of the present invention lies in rapid endgroup sequencing and analyses that may be accomplished by the methods described herein.

For example, aminopeptidases and carboxypeptidases are enzymes that release amino acids sequentially, one-at-a-time, from a protein's amino-terminus and carboxy-terminus, respectively. These enzymes are used in discontinuous kinetic assays for protein end-group sequencing. Due to the nonlinear rate of hydrolysis, those kinetic studies have been generally unsuccessful. Real-time amino acid analysis microarrays that can detect amino acids as they are released by these enzymes are thus a further aspect of this invention. These arrays are integrated with aminopeptidase or carboxypeptidase digestions, creating online microfluidic systems capable of generating either N-terminal or C-terminal sequence data. As amino acids are liberated by an exopeptidase, they flow from the digestion chamber through the amino acid analysis microarrays and are detected sequentially. Desirably, the digestion chamber is separated from the analysis arrays by a membrane which allows only small molecules to pass, thus protecting the channels or wells or microarrays from debris or whole proteins which could foul or plug the system. In addition, or alternatively, the protein of interest and/or the exopeptidase can be bound to the interior of the digestion chamber. The terminal sequence is generated by a computer upon analysis of the sequential amino acid detection data. If the sequence information is generated from an unidentified protein, for example, the protein can be identified by automated database searching, provided that it is one for which sequence information is available on accessible databases.

Carboxypeptidases and aminopeptidases have been used for sequencing proteins for many years (Light, A. (1967) *Meth. Enzymol.* 11:426–444; Breddam and Ottesen (1987) *Carlsberg Res. Comm.* 52:55–63; Royer, G. (1972) *J. Biol. Chem.* 218:1807–1812). Carboxypeptidases and aminopeptidases have been used for end group protein and peptide sequencing (Martin et al. (1971) *Carlsberg Res. Comm.* 44:99–102; Klarskow et al. (1989) *Anal. Biochem.* 180:28–37; Thiede et al. (1995) *FEBS Letts* 357:65–9; Bonetto et al. (1997) *Anal. Chem.* 69:1315–1319; Bonetto et al. (1997) *J. Protein Chem.* 16:371–374; Light, A. (1968) *Methods Enzymol.* 11:426–444). These enzymes are ideal for removing amino acids sequentially from the N-termini of proteins (aminopeptidases) or the C-termini of proteins (carboxypeptidases). During the course of a digestion, samples are taken and analyzed later using an amino acid analyzer. Inherent in the use of these discontinuous assays is the assumption that the amino acids are being released linearly with time over the period chosen, however, the rate of cleavage is sequence dependent and varies unpredictably. When an analyte varies unpredictably, a continuous (real-time) assay is needed. A continuous assay is not possible using existing methods of amino acid analysis. This problem is solved by the continuous amino acid sensor arrays of the present method which utilize the method of amino acid analysis described herein.

Carboxypeptidases and aminopeptidases for use in sequencing reactions described herein are commercially available from numerous suppliers (e.g., Pierce Chemical Co., Rockford, Ill.). Examples of carboxypeptidases suitable for use in the subject invention for end group sequencing and end group analysis include, but are not limited to, carboxypeptidase Y, carboxypeptidase P, carboxypeptidase A, and carboxypeptidase B. Aminopeptidases, including aminopeptidases L and M, which are commercially available, are used for amino terminal sequence analysis. The exopeptidases can be immobilized using spacer arms for use in end group sequencing. Immobilized aminopeptidases and carboxypeptidases suitable for protein end group sequencing are commercially available. Mixtures of different carboxypeptidases for C-terminal sequencing and different aminopeptidases for N terminal sequencing are often used to give suitable digestion rates.

The high-throughput amino acid analysis microchips described herein are useful in the developing field of proteomics. These microarrays allow for the amino acid analysis of all proteins separated by a 2D electrophoresis gel on a single chip or plate simultaneously. In proteomics, it is especially important to determine the N-terminal and C-terminal sequence of an intact protein. End-group sequencing can be used to identify the start and stop point of a protein or gene; provides sequence information necessary for PCR cloning of the intact gene; identifies limited proteolytic products, which are common to many important regulatory mechanism; and provides a powerful method to identify proteins separated by 2D gels. Microfabricated end-group sequenators such as those described can be constructed as massively paralleled, computer controlled and integrated systems, where both N-terminal and C-terminal sequencing of many proteins can be performed on a single chip platform simultaneously. The terminal sequence tags generated can be processed on-line and the proteins identified by database searching. Among the most outstanding deficiencies in the current set of methods in protein chemistry are the ones for C-terminal sequencing. Since no sensitive and reliable method for C-terminal sequencing is available, the C-terminus of proteins is a protein region that is often not analyzed. Hence, the C-terminal sequenators of the present invention are especially useful in proteome projects.

High throughput methods for protein end group amino acid analysis methods to identify the C-terminus of proteins are further aspects of this invention. The methods for C-terminus analysis prior to the present invention are inadequate for analysis of minute quantities of protein. These inadequate methods include hydrazinolysis (Steydon, D. J. (1988) *Anal. Biochem.* 174:677–686) and tritium incorporation using tritiated water after treatment of the protein with acetic anhydride to form the oxazolone (Matsuo et al. (1966) *Biochem. Biophys. Res. Commun.* 22:69–74). Both methods are relatively insensitive and prone to problems. Most researchers have been forced to identify the C-terminus of a protein by peptide mapping strategies. This method is not quantitative and may miss the correct C-terminal peptide or minor but important C-terminal peptides. The present invention couples carboxypeptidase digestion with high throughput microarrays and Microsystems for rapid C-terminal analysis. The method described herein is suitable for protein end group amino acid compositional analysis, which is used to identify proteins in conjunction with sequence database searching.

Another important consideration in proteome studies is sensitivity. Proteins, unlike genes, have no amplification methods, so sensitivity is even more important than for gene analysis. In order to analyze minor proteins separated from 2D gels it is often necessary to work at the femtomole level. Current amino acid analyzers and sequenators fall short of this level by three orders of magnitude. By converting the amino acids into macromolecules (AA-tRNAs) that are specifically bound by another macromolecule (e.g., EF-Tu:GTP) with a high affinity ultrasensitive ligand assays and automated microarrays for amino acid analysis the methods of the present invention are thus particularly useful. With laser induced fluorescence as a detection method, simple and sensitive amino acid analyzers and end-group sequenators thus form an aspect of the present invention.

The Digestion Chamber

An exemplary digestion chamber is traversed by a microdialysis or ultrafiltration probe having a molecular weight cutoff that allows free passage of amino acids but is impermeable to macromolecules. If the molecular weight cutoff is 6,000 Da, for example, then amino acids should pass freely across the membrane, but polypeptides longer than about 50 amino acids should not. Peptides to be analyzed may furthermore be conjugated to other molecules to prevent passage through the membrane. For example, peptides may be conjugated to dextran or other polymers or substances. Peptides to be used for C-terminal sequencing can be conjugated to molecules using amino-terminal coupling chemistries, and peptides to be used for N-terminal sequencing can be conjugated to polymers using carboxy-terminal coupling chemistries. If immobilized exopeptidases are to be used, the peptides to be sequenced are optionally coupled to small polymers (e.g., MW 50–100 kDA) rather than beads to prevent mass transport problems.

Preferably, the systems of the present invention are designed so that each liberated amino acid will diffuse (or be transported) to its immobilized cognate synthetase (or tRNA) and be detected before the next amino acid is released. Diffusion is rapid over distances of a few micrometers. Diffusion times increase with the size of the molecule and the square of the distance traveled. For amino acids in water at 37° C. diffusion times are approximately 1 msec for 1 micron, 0.1 sec for 10 microns and 17 min for 1 mm. For systems larger than a few micrometers, transport optionally takes place by convection for real-time sequential monitoring.

Figure 5A:
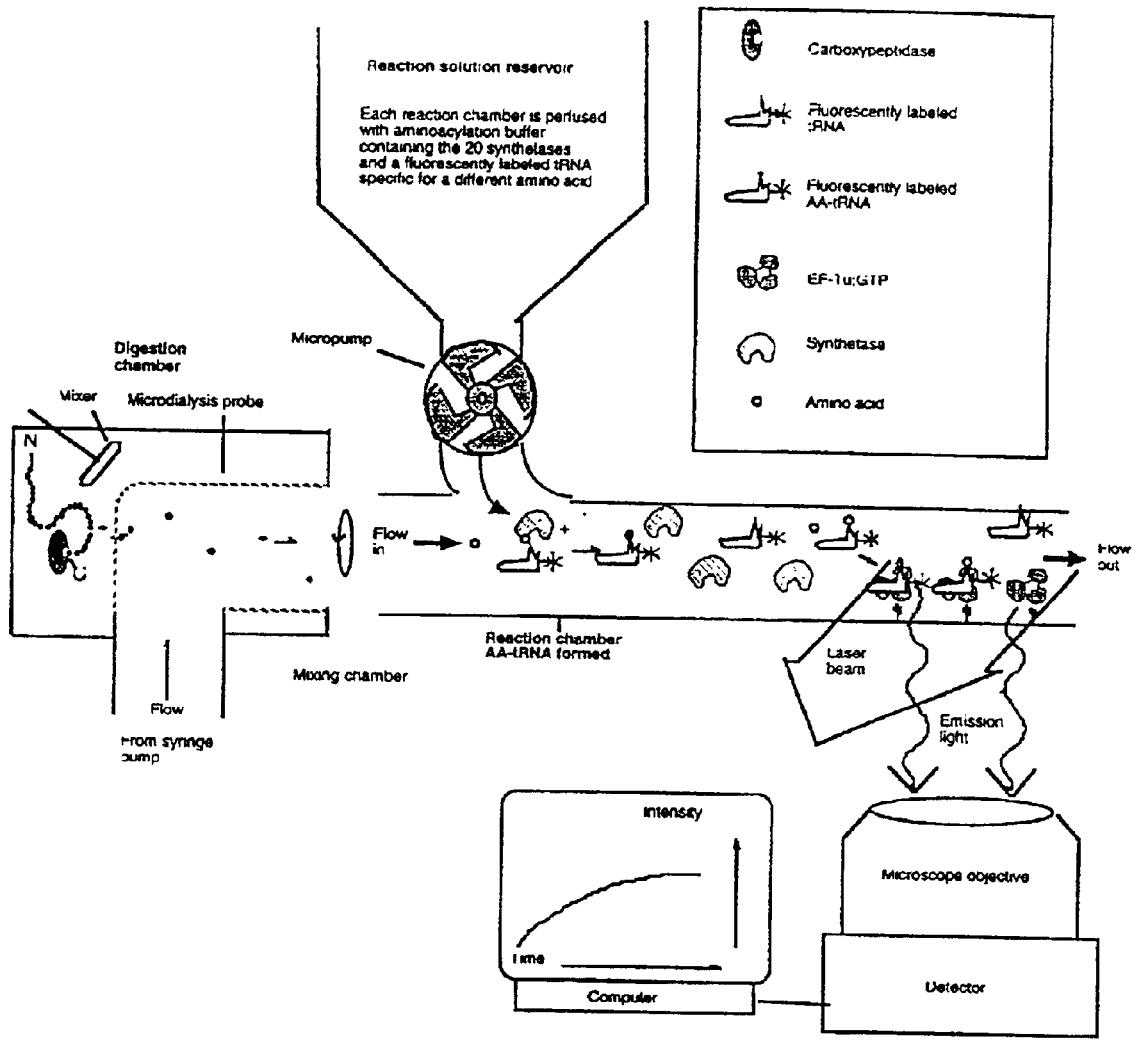
FIGS. 5A, 5B, and 5C generally illustrate a process of continuous-flow protein sequencing on a chip.

Chip enzymatic nanosequenators are a still further aspect of the present invention. Certain components of such systems such as continuous flow mixers, pumps, microreactors, microdialysis and miniaturized ultrafiltration systems are known (Kricka et al. (1998) *Clin. Chem.* 44:2008–2014). A C-terminal nanosequenator of the present invention is illustrated in FIG. 5A of Example 4 below. The carboxypeptidase digestion takes place in a tiny chamber traversed by a microdialysis probe or miniaturized ultrafiltration probe. The membrane has a molecular weight cutoff such that it allows free passage of amino acids but is impermeable to the protein substrate and carboxypeptidases. As the amino acids are liberated from the protein's termini, they cross the membrane and enter a flow stream which carries them to the biosensor or sensor array for continuous detection. The sequential record of the continuous detection of the 20 amino acids by the miniaturized sensor and/or biosensor array provides the terminal sequence of the protein.

EXAMPLES

The following examples are provided for illustrative purposes, and are not intended to limit the scope of the invention as claimed herein. Any variations in the exemplified articles and/or methods which occur to the skilled artisan are intended to fall within the scope of the present invention.

Example 1

Example 1 illustrates the use of an array to simultaneously and quantitatively detect each of the individual primary amino acids in a sample. As shown in FIG. 1A, the 20 aminoacyl-tRNA synthetases and/or a cognate tRNA specific for a different amino acid can be arranged in array format. By dispensing each synthetase into a different well at a known position, the amino acid-specific reactions catalyzed by these enzymes can be used to identify and quantitate their cognate amino acids. Each well thereby would signal only the amino acid cognate to the synthetase and/or tRNA present in that well. The single letter codes for the amino acids are used in this figure to represent the synthetase or tRNA cognate for the corresponding amino acid. In this embodiment, as shown in FIG. 1A, the reactions catalyzed by the synthetases are carried out in parallel and are monitored in all the wells simultaneously by use of a plate reader. The presence and amounts of the various individual amino acids may be determined by monitoring the formation of any of the reaction products of the aminoacyl t-RNA synthetase reaction.

The reaction conditions and buffers suitable for carrying out the amino acid synthetase reactions are well known to one of ordinary skill in the art. The aminoacyl-AMP:aminoacyl-tRNA synthetase complexes may be the measured reaction product. These products are most stable at slightly acidic pH (e.g., pH 6.0) and any nucleophiles preferably are excluded form the buffer and wash as they readily attack the acyl-phosphate bond. AA-AMP's often have half-lives of hundreds of minutes on the synthetases. They die by base-catalyzed hydrolysis so this can be extended by working at lower pH. The half life can be extended 10-fold by working at pH 6 rather than 7. The wash buffer in this case will be free of nucleophiles and may optionally be at a slightly acidic pH.

Example 2

Example 2 describes several different embodiments wherein an elongation factor is used in the detection of a ternary complex.

Immobilization of the EF-Tu:GTP with Labeling of the tRNA.

Figure 1B:
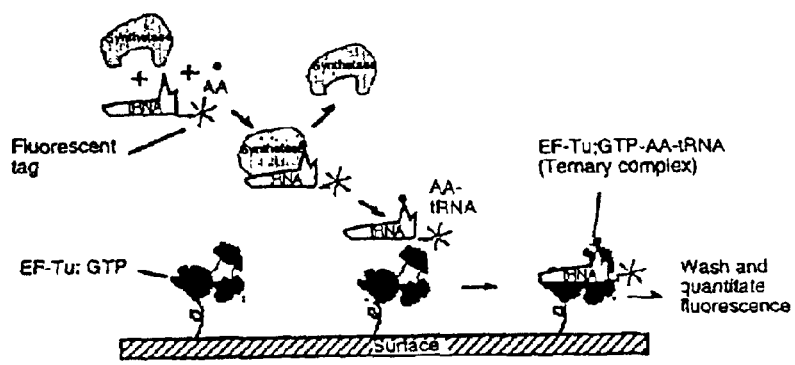

In a first embodiment as shown in FIG. 1B, EF-Tu:GTP is immobilized to the surface of a reaction site (e.g., the bottom of a microtiter wells). The shown site may be one of many sites providing aminoacyl tRNA synthetase reactions and having immobilized EF-Tu:GTP. In a preferred embodiment, there are such sites for each of the 20 primary amino acids containing a different one of the 20 synthetases in aminoacylation buffer and its labeled cognate tRNA. As shown in FIG. 1B, the tRNA is attached to a label, which in this case is a fluorescent label. After the amino acid mixture or sample is added to the reaction site, the aminoacyl tRNA synthetase catalyzes the formation of the correspondingly labeled aminoacyl tRNA. The labeled aminoacyl tRNA binds to the immobilized EF-Tu:GTP to form a labeled ternary complex. Thereupon, the reaction site is washed with a suitable buffer which does not interfere with the binding of the labeled aminoacyl tRNA to the immobilized EF-Tu:GTP. After a washing step to remove the unreacted fluorescently labeled tRNA, the bound fluorescence or other label is quantitated using a fluorometer (plate reader) or other detection system. Depending on the fluorescent labels and instrumentation, detection limits as low as femtomole-attomole sensitivities can be achieved.

Immobilization of the tRNA with Labeling of the EF-Tu:GTP.

Figure 2A:
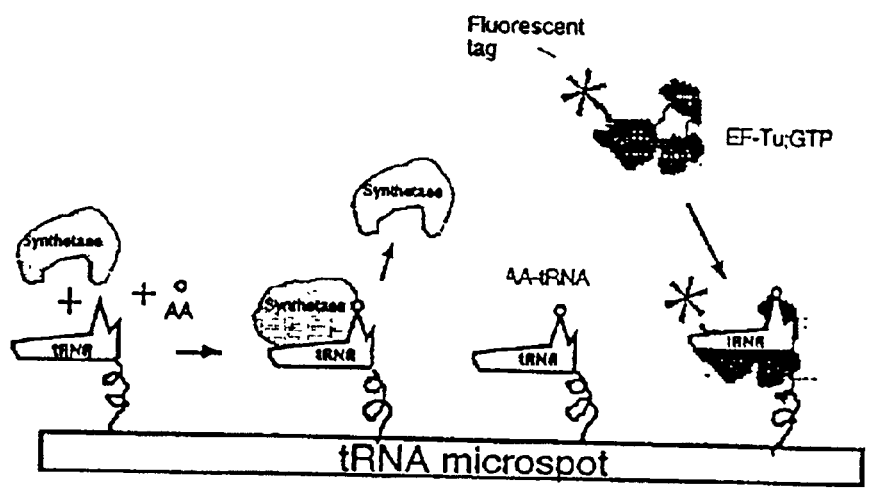

In another embodiment as shown in FIG. 2A, the tRNA is immobilized to the surface of a solid support at the reaction site and the EF-Tu:GTP is labeled. While FIG. 2A shows only one tRNA immobilization site, an array of such sites may be provided comprising a plurality of immobilized amino acid-specific tRNAs. In such an array from one to twenty tRNAs (one specific for each amino acid) may be immobilized in an array of microspots. In the case of such an array, each unique amino acid is detected according to the known location of the corresponding tRNA on the array. A mixture of amino acids or the sample is added along with the 20 synthetases and fluorescently labeled EF-Tu:GTP in the reaction buffer. AA-tRNAs are formed on each microspot in proportion to the concentration of amino acid-specific for each immobilized tRNA. Fluorescently labeled elongation factor binds the AA-tRNAs, and the labeled complex is detected by laser induced fluorescence using position-specific detectors.

Co-immobilization of the Aminoacyl tRNA Synthetase and the EF-Tu:GTP with Labeling of the tRNA.

Figure 2B:
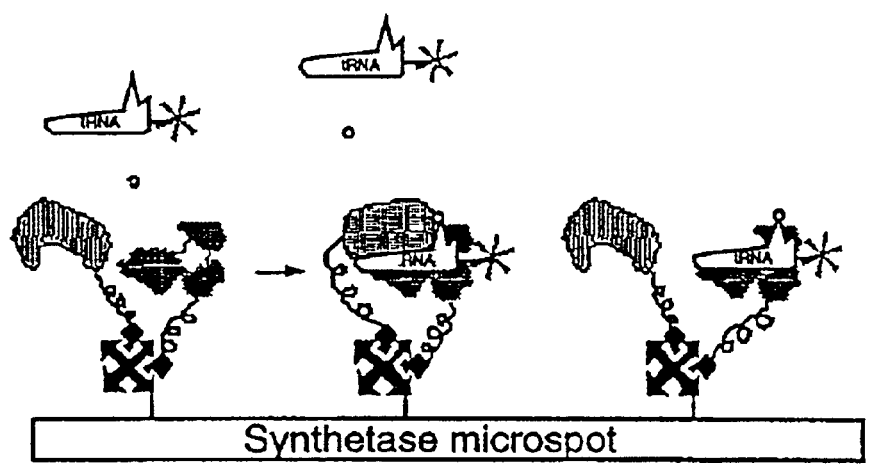

Another embodiment is illustrated in FIG. 2B. In this embodiment, the synthetase and EF-Tu:GTP are each immobilized to a surface at the reaction site. A plurality of sites providing a plurality of aminoacyl tRNA synthetases may be provided in the form of an array. In such an array, the primary protein aminoacyl tRNA synthetases are co-immobilized with EF-Tu:GTP in separate microspots each of known location. In this format, fluorescently labeled tRNAs are used in the reaction to allow detection of the resulting fluorescent aminoacyl tRNA product. In the presence of the tRNA specific for the amino acid in the sample to be analyzed, the amino acid is converted into the corresponding AA-tRNAs and 'captured' on the corresponding aminoacyl tRNA synthetase microspot by the immobilized EF-Tu:GTP. Amino acids are detected by laser induced fluorescence. The amount of AA-tRNA captured on each microspot, and hence the amount of amino acid in the sample, is determined by laser-induced fluorescence of the captured AA-tRNA.

Example 3

The reaction conditions and buffers suitable for binding of elongation factors to aminoacyl tRNAs are well known to one of ordinary skill in the art. Examples of suitable reaction buffers for monitoring the binding of EF-Tu:GTP to the AA-tRNAs include but are not limited to:

1. 50 mM Tris-HCl, pH 7.5, 50 mM $NH_4Cl$, 50 mM KCl, 10 mM $MgCl_2$, 1 mM GTP, 5 mM beta-mercaptoethanol, 1 mM ATP, 23° deg C.
2. 50 mM Tris-HCl, pH 7.5, 25 mM KCl, 15 mM MgCl, 2 mM beta-mercaptoethanol, 10 mM ATP, 10 mM phosphoenolpyruvate, 120 ug/ml pyruvate kinase, 1 mM GTP The binding of the AA-tRNAs to the EF-Tu:GTP may be performed at room temperature when using the elongation factor from *T. thermophilus*, for example, taking advantage of the thermal stability of this protein. In brief, the AA-tRNAs are reacted with the EF-Tu:GTP in reaction buffer. The EF-Tu:GTP is optionally bound to a surface.

In cases where one molecule is immobilized and used to "capture" another molecule a wash step may be desired to remove unbound or weakly bound reagents. For example, in cases where the EF-Tu:GTP is immobilized and used to capture AA-tRNAs a wash step may be employed to remove the unbound substances. Other examples include cases where tRNAs are immobilized and the AA-tRNAs formed on these immobilized tRNAs by the synthetases are reacted with tagged EF-Tu:GTP; synthetases are immobilized and tagged ATP forms AA-AMP;synthetase complexes; or a probe (e.g., an antibody that recognizes the ternary complex (EF-Tu:GTP-AA-tRNA) is immobilized and used to capture ternary complexes. The conditions of the wash buffer will be such that unbound species are removed but the bound complex is not disturbed.

Examples of suitable wash buffers for ternary complexes (EF-Tu:GTP-AA-tRNA) include but are not limited to the following:

3. 50 mM Tris-HCl, pH 7.5, 50 mM $NH_4Cl$, 50 mM KCl, 10 mM $MgCl_2$, 1 mM GTP, 5 mM beta-mercaptoethanol
4. 50 mM HEPES, pH 7.5, 150 mM NaCl, 50 mM beta-mercaptoethanol, 50 uM GTP.

In some embodiments of the subject invention it is desirable to elute the AA-tRNAs bound to the EF-Tu:GTP binary complex. For example, in cases where the EF-Tu:GTP complex is immobilized and used to "capture" the AA-tRNAs, the bound AA-tRNAs may be eluted and the immobilized elongation factor may be re-used.

For example, suitable elution buffers include but are not limited to the following:

1. 100 mM sodium borate, pH 7.5, 1M NaCl, 10 mM, $MgCl_2$, 5 mM beta-mercaptoethanol, 50 uM GTP
2. 50 mM Hepes, pH 7.5, 150 mM NaCl, 50 mM $NH_4Cl$, 10 mM $MgCl_2$, 5 mM beta-mercaptoethanol, 1 mM GDP For aminoacyl-tRNA;EF-Tu:GTP ternary complex formation, EF-Tu;GDP may be converted to EF-Tu:GTP by incubation of 30 uM EF-Tu;GDP with 5 mM phosphoenolpyruvate, 1 mM GTP, 50 mM Tris/HCl, pH 7.5, 50 mM KCl, 50 mM $NH_4Cl$, 10 mM $MgCl_2$, 10 mM beta-mercaptoethanol, and 100 ug/ml pyruvate kinase, for example.

Example 4

Figure 3:
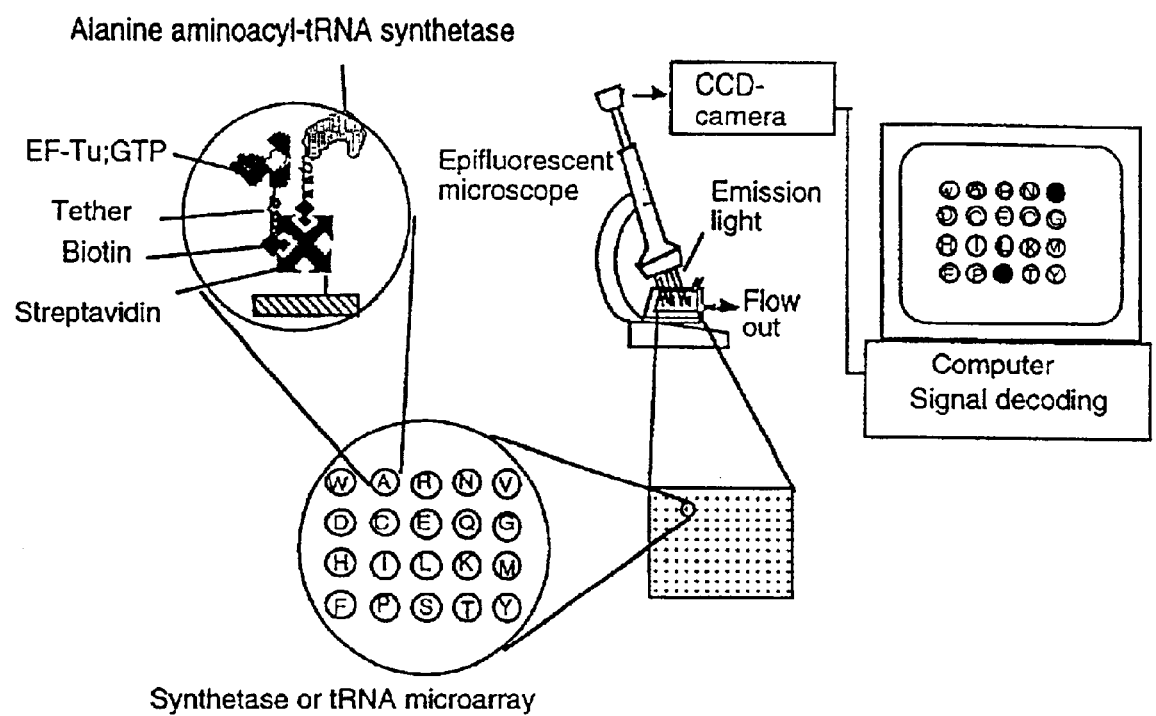
FIG. 3 is a schematic diagram of an optical fiber amino acid analyzer.

FIG. 3 further describes the use of co-immobilized aminoacyl tRNA synthetase and EF-Tu:GTP on microspots in an array format. As shown in FIG. 3, each synthetase is co-immobilized with EF-Tu:GTP on a different reaction site of the array.

FIG. 3 generally illustrates a spatially resolved detection system for amino acid analysis microarrays of the present invention. Patterned arrays of biorecognition elements (synthetases, or tRNAs) are immobilized on a surface at known spatially resolved locations. Single letter codes for amino acids represent the synthetases or tRNAs specific for each amino acid. Each patterned microdot signals its cognate amino acid after it is captured into the EF-Tu:GTP-AA-tRNA complex as described above. In cases where the tRNAs are immobilized as microdots, the elongation factors can be fluorescently labeled. And where synthetases and elongation factors are immobilized as microdots, the tRNAs are fluorescently labeled. Upon excitation of the fluorescent labels, a spatially specific detector linked to a computer allows analysis of the pattern and intensity of fluorescently labeled molecules on the surface. As shown, the fluorescence is imaged through the microscope, and the detector is a high-sensitivity CCD camera. Fluorescence intensity on the arrays is correlated with the amount of amino acids in the sample, and the position of the fluorescent label on the surface identifies the amino acid. Thousands of samples can be analyzed on a single microarray.

Example 5

Example 5 illustrates the use of an optical fiber amino acid analyzer array as applied to the determination of an end terminal protein sequence.

Fiber optics can be used as thin flexible pipes to transport light to and from tiny volumes of immobilized chemistry at the probe end. Optical fibers offer several advantages for the construction of amino acid analysis sensor arrays and/or biosensor arrays of the present invention. For example, optical fiber bundles for combining sensing and imaging and creating optical sensing arrays may be utilized (See, e.g., Healy et al. (1995) *Science* 269:1178–1180). Optical fibers provide a highly miniaturizable transduction format and thus allow monitoring in real-time (Healey and Walt (1997) *Anal. Chem.* 69:2213–2215). The tips of optical fibers can be of submicron dimensions. Optical fiber sensors can use the evanescent field to excite and collect the fluorescence of molecules bound to the surface. The evanescent wave excites only fluorophores that are bound to the surface. This allows real-time detection of the captured probe on microarrays even in the presence of high concentrations of fluorophores in the bulk solution without washing.

Specific synthetases or tRNAs cognate for a different amino acid can thus be immobilized to a separate fiber. Each fiber tip signals the amino acid cognate to the immobilized synthetase or tRNA. For example, each synthetase can be co-immobilized with EF-Tu:GTP to a different fiber, and the formation of the ternary complex on each fiber can be monitored using fluorescently labeled tRNAs. When coupled to aminopeptidase or carboxypeptidase digestions these ultrasmall sensors may allow real-time protein end-group sequencing in tiny volumes (<1 microliter).

Figure 4:
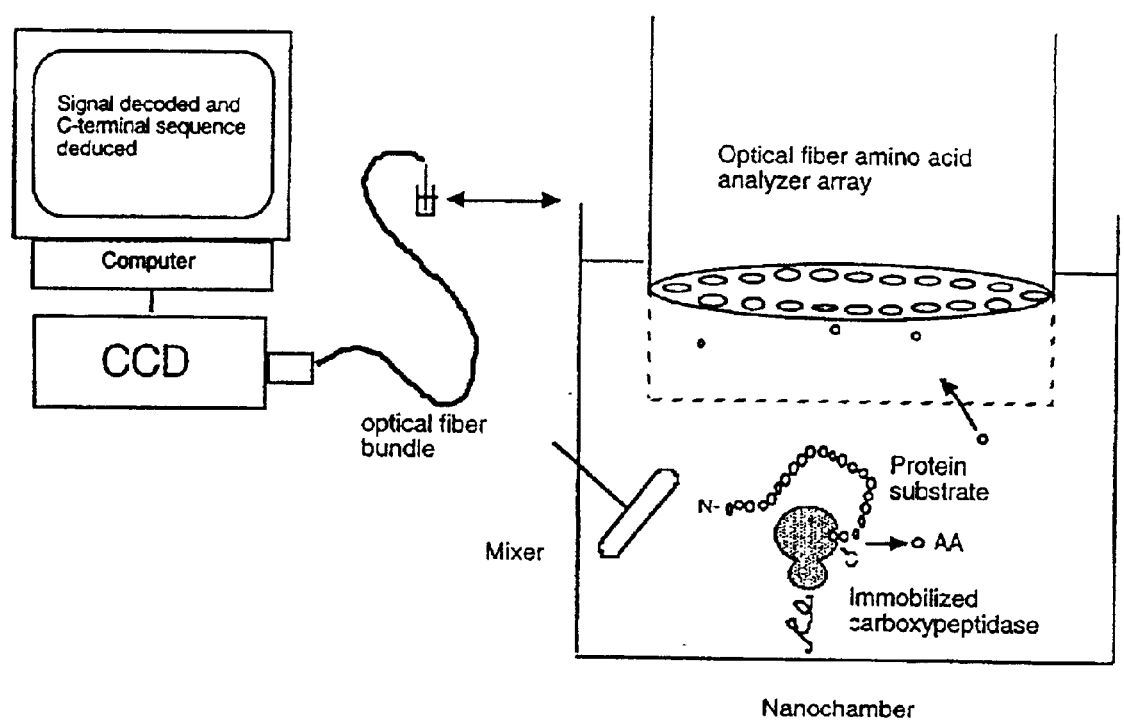
FIG. 4. is a schematic diagram of an evanescent wave optical fiber C-terminal nanosequenator.

While the example illustrates the use of an optical fiber arrangement for such sequencing, one of ordinary skill in the art would readily recognize the other applications of the optical fiber arrangement is itself suitable for use with other samples. As depicted in FIG. 4, each aminoacyl tRNA synthetase can be co-immobilized with EF-Tu:GTP on a different optical fiber. The tRNAs reaction substrates may be labeled with fluorescent tags. The formation of the ternary complex (AA-tRNA-EF-Tu:GTP) on the sensor surface may be then monitored continuously by fluorescence detection of the fluorescent tag incorporated into the aminoacyl tRNA product. The biorecognition elements (synthetases, tRNAs, and elongation factors) are optionally enclosed by a semi-permeable membrane having a molecular weight cutoff that allows free passage of amino acids but is impermeable to macromolecules. Amino acids are detected according to the known fiber location of the corresponding synthetase.

In a preferred embodiment, as shown, these miniaturized optical fiber amino acid biosensor arrays are used in combination with aminopeptidases or carboxypeptidases for protein end group amino acid sequencing and amino acid analysis. In this embodiment, fluorescently labeled AA-tRNAs are captured on the sensor surface in response to amino acids cognate to the synthetase becoming immobilized at each of the amino acid specific fiber ends. Excitation and emission light travels through each fiber. Emission light is imaged through a microscope objective onto a CCD detector for continuous detection. The temporal pattern of the fluorescence detected on each fiber end generates the terminal sequence of the protein being sequenced.

The optical fibers are typically composed of glass or plastic. They comprise two fiber ends designated as the sensor and transmission ends and are able to convey electromagnetic radiation introduced at either end. Optical fibers are commonly used in biosensors and other sensors and are commonly known in the art.

In the current invention, groups of fibers may each be labeled with a different synthetase or tRNA specific for one amino acid. This will provide a source of redundancy in the assay. Since each fiber in the sensor will be small (may be less than 1 micrometer,) the sensor end will be sufficient to insert into an organism or microchannel or capillary. The sensor end may optionally be encapsulated by a dialysis membrane to create a microdialysis probe.

The placement of sensor ends may be highly ordered with the sensor end of each fiber occupying a specific predetermined location in the sensor end. Hence, a different synthetase or tRNA may be attached to the sensor end in a known location so that binding of fluorescently labeled molecule to each synthetase or tRNA is spatially addressable. This comprises the localizing of optical fibers on bundles of optical fibers at fixed locations relative to other fibers in the bundle comprising the optical fiber sensor array.

Detection of signal may be achieved by the use of one or more detectors. A lens may be attached to the transmission end of the optical fiber. The optical signal may be detected visually or with a detector. Typical detectors are phototubes or charge coupled devices.

The detection system is linked to a computerized data acquisition system and analytical program.

The amino acid biosensor may be used to detect a single amino acid in a test sample. It may be used in vivo, in culture, or in vitro. In the case of the synthetase or tRNA specific for unique amino acids or any combination of the amino acids to be analyzed, it or they are immobilized to the sensor as described.

The sensor may measure the presence of absence of an amino acid in the sample.

The optical signal may typically be generated by fluorescent, luminescent, or colorimetic label present at the sensor end of the optical fiber. Typically, the concentration of the label at the sensor end of the optical fiber is a function of the concentration of the analyte that specifically binds to the biological binding partner.

Methods of providing a label whose concentration is a function of the amount of analyte specifically associated with the binding partners are know to those of ordinary skill in the art. For example, the analyte may be labeled; or the labeled analyte may be pre-bound to the biosensor and a displacement of the labeled analyte by the unlabeled analyte in the sample produces a reduction in signal.

The excitation light (not shown) may be provided by a separate light source. Methods of excitation using optical fibers are well know to those of ordinary skill in the art (see for example, U.S. Pat. Nos. 4,447,546 and 4,909,990). Suitable light sources include but are not limited to lasers, LEDs and lamps. Appropriate filters for excitation light and fluorescent emissions may be added at any point along the light paths. Light source will be appropriate to the dyes employed. For example, a set up introducing excitation light and detecting emission light using optical fiber sensors is disclosed in Bronk K. S. et al. (1995) *Anal. Chem.* 67: 2750–2757). Immobilization of biomolecules may b, for example, by biotinylation of RNAs or protein bound to avidin-treated fibers (see Abel A. P. et al. (1966) *Anal Chem.* 68: 2905–12).

Example 6

Example 6 further describes various methodologies for amino acid detection as exemplified in sequencing a protein of interest.

In a first embodiment, as shown in FIG. 5A, the protein of interest is first digested at one end by a aminopeptidase or, more preferably as shown, a carboxypeptidase. The carboxypeptidase digestion takes place in a tiny chamber, and the released free amino acids are collected by a microdialysis or ultrafiltration probe. As the amino acids are released by the carboxypeptidase, they cross the membrane and enter the flow stream. This flow stream enters a continuous flow mixer and then distributed to an array of 20 reaction chambers or channels. For simplicity, only one reaction chamber is shown. In each of the amino acid specific reaction channels or chambers, the flow stream is joined by a second flow stream carrying a fluorescently labeled tRNA that is specific for a different amino acid and the cognate synthetase. EF-Tu:GTP is immobilized downstream in each reaction channel. Amino acids cognate for the labeled tRNA in each channel or chamber are converted into a proportionate amount of AA-tRNA, which is captured by the immobilized EF-Tu:GTP. A laser beam focused on the immobilized EF-Tu:GTP allows detection of the fluorescently labeled AA-tRNAs as they bind the elongation factor. The emitted light is imaged to a CCD detector, and analysis of the record of the binding of AA-tRNAs to EF-Tu:GTP in the 20 chambers yields the C-terminal sequence of the protein.

Figure 5B:
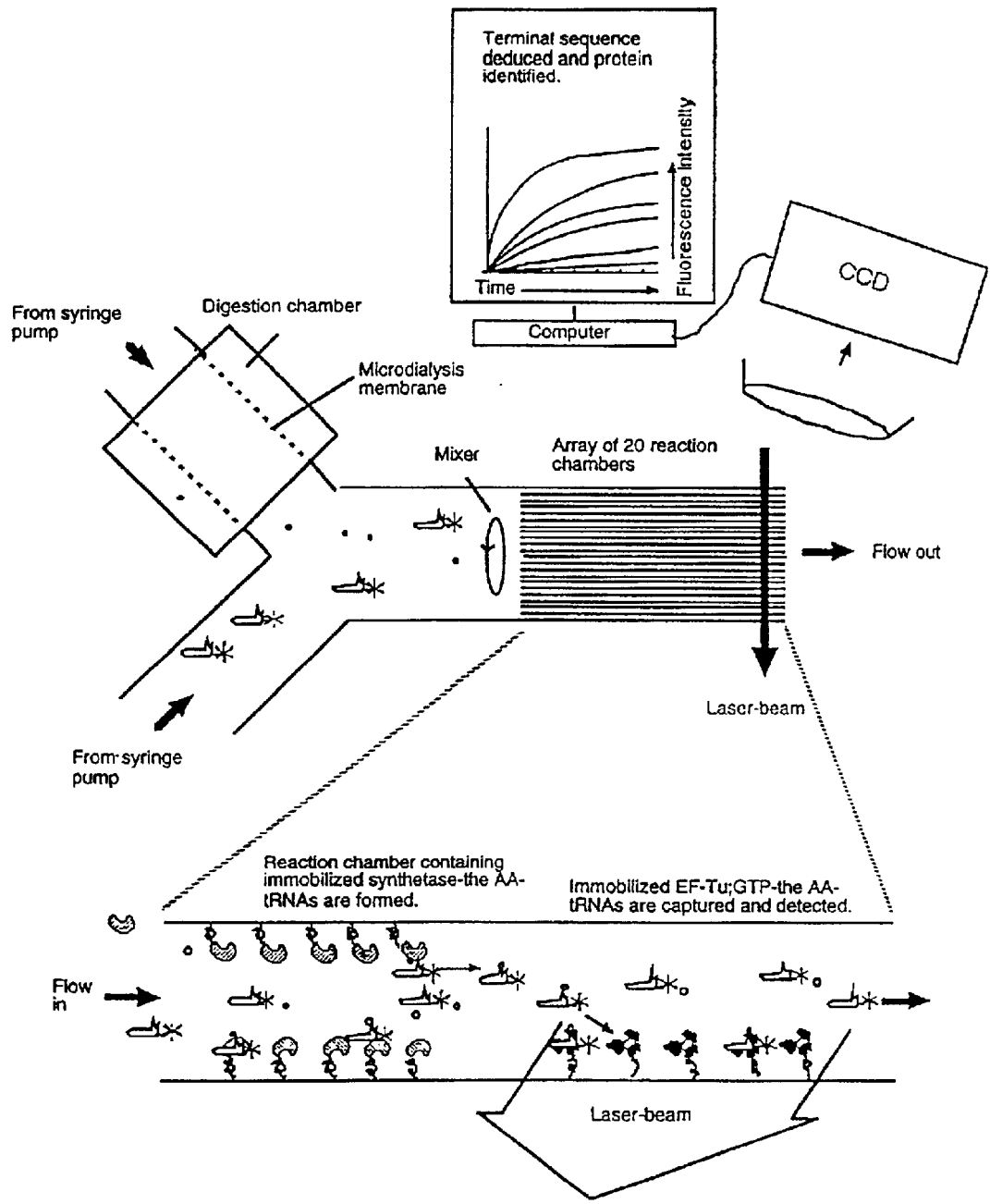

FIG. 5B presents another arrangement by which a protein may be end terminal sequenced using the inventive methods. In this embodiment, each of the 20 synthetases is immobilized in a separate reaction channel. Amino acids sequentially liberated from the protein's end traverse the microdialysis probe and enter the flow stream which is joined by a second flow stream carrying fluorescently labeled tRNAs (one cognate for each of the 20 primary amino acids) in reaction buffer. The two flows are mixed on the chip and enter the reaction channel array. In each reaction channel, amino acids having a cognate synthetase immobilized are converted into a proportionate amount of AA-tRNA. The newly formed AA-tRNAs bind to EF-Tu:GTP immobilized downstream and are continuously detected as described above.

Figure 5C:
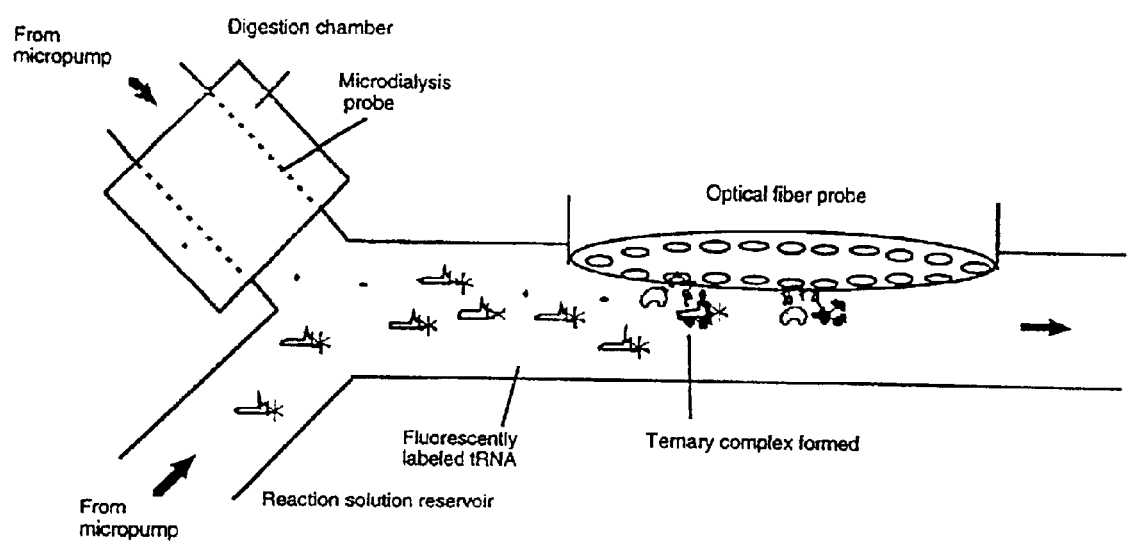

FIG. 5C presents another arrangement by which the terminal sequence of a protein may be determined. In this embodiment, two flow streams are combined and mixed on the chip. One stream contains the amino acids released during end terminal digestion of the protein. This stream flows through a microdialysis probe that traverses a tiny digestion chamber. Liberated amino acids cross the microdialysis membrane of the probe and enter the flow stream. The second flow stream contains a mixture of fluorescently labeled tRNAs (one specific for each amino acid) in reaction buffer. The two flows are combined and mixed. This stream containing the mixture of amino acids and fluorescently labeled tRNAs flows through the biosensor array upon which both synthetases and elongation factors have been immobilized in an array providing 20 aminoacyl tRNA synthetases corresponding to the 20 primary protein amino acids. Amino acids are attached to their cognate tRNAs by the immobilized corresponding synthetase and the resulting aminoacyl tRNA is bound by the co-immobilized elongation factors. The bound AA-tRNAs are then quantitated by fluorescence detection.

One of ordinary skill in the art would find it obvious to adapt the above approaches to the analysis of not just protein digests, but of any sample containing an amino acid to be detected or analyzed.

Example 7

This example illustrates several embodiments of binding assays using dual labels to detect a reaction product: Ekins et al. (1991) *Clin. Chem.* 37: 1955–1967; U.S. Pat. No 5,171,695 describes a binding assay using dual labels in which the fractional occupancy of an immobilized receptor is an accurate and reliable measure of the concentration of its ligand in the sample. This assay depends on ligand concentration to which the immobilized receptor has been exposed. That is, it is independent or particularly insensitive to the immobilized receptor concentration. This binding assay will find use in some of the preferred embodiments of the subject invention.

Microdot Synthetase-EF-Tu:GTP Arrays for Amino Acid Analysis using Dual Labels

In this embodiment, the aminoacyl-tRNA synthetases are to be co-immobilized with EF-Tu:GTP on a surface (e.g., in the bottom of a well) as spatially separated zones (microdots). The EF-Tu:GTP is preferably labeled with Texas Red. A mixture of fluorescein isothiocyanate labeled tRNAs containing tRNAs specific for each amino acid to be analyzed, is added along with the amino acid sample and reaction buffer. The AA-tRNAs form and are captured on the immobilized EF-Tu:GTP-Synthetase spots. After an incubation period, the unbound material is removed with a wash step. The fractional occupancy of the Texas Red-EF-Tu:GTP-Synthetase spots by the fluorescein labeled tRNAs is determined by excitation of the fluorescent dyes and reading the excitation light. For example, a scanning confocal microscope may be used. Dual excitation may be employed, for example, using an argon laser with excitation at about 488 nm and 514 nm. The fractional occupancy for each microdot is obtained from the ratio of the emission light from the two labels.

Microdot tRNA Arrays for Amino Acid Analysis Using Dual Labels

In this example tRNA specific for each amino acid are labeled with fluorescein isothiocyanate and immobilized to a surface (e.g., the bottom of microwells) as microspots. A mixture of the aminoacyl-tRNA synthetases are added in reaction buffer along with the amino acid sample. The amino acids are attached to the immobilized tRNAs by the synthetases. Texas Red labeled EF-Tu:GTP is added to the wells and allowed to bind to the AA-tRNAs. After an incubation period, a wash step is used to remove the unbound material. The fractional occupancy of the tRNA spots by the Texas Red labeled EF-Tu:GTP is determined by excitation of the dual labels and detecting the excitation light. Dual excitation may be achieved using an argon laser, for example, with excitation at around 488 nm and 514 nm. The fractional occupancy of each microdot in the array is obtained from the ratio of the emission light from the two labels.

Microdot Aminoacyl-tRNA Synthetase Arrays Using Dual Labels

In this example the Texas Red labeled aminoacyl-tRNA synthetases are arrayed onto a surface in spatially separated zones on the bottom of microwells. An amino acid sample is added to the wells along with fluorescein isothiocyanate labeled ATP in reaction buffer. The fluorescently labeled ATP along with amino acids is converted into Texis Red-synthetase-AA-AMP-fluorescein complexes. After an incubation period, a wash step is employed to remove unbound material. The fractional occupancy of the Texas Red labeled synthetase spots with AA-AMP-fluorescein is determined by excitation of the dual labels and detection of the emission light from the two color dyes. Excitation may be at around 488 nm and 512 nm. A confocal fluorescent scanner may be used as a detector.

Example 8

Example 8 describes various approaches for co-immobilizing tethering of the aminoacyl tRNA synthetases and elongation factor using EF-Tu:GTP as the exemplary elongation factor.

Use of a Single Tether

Figure 6A:
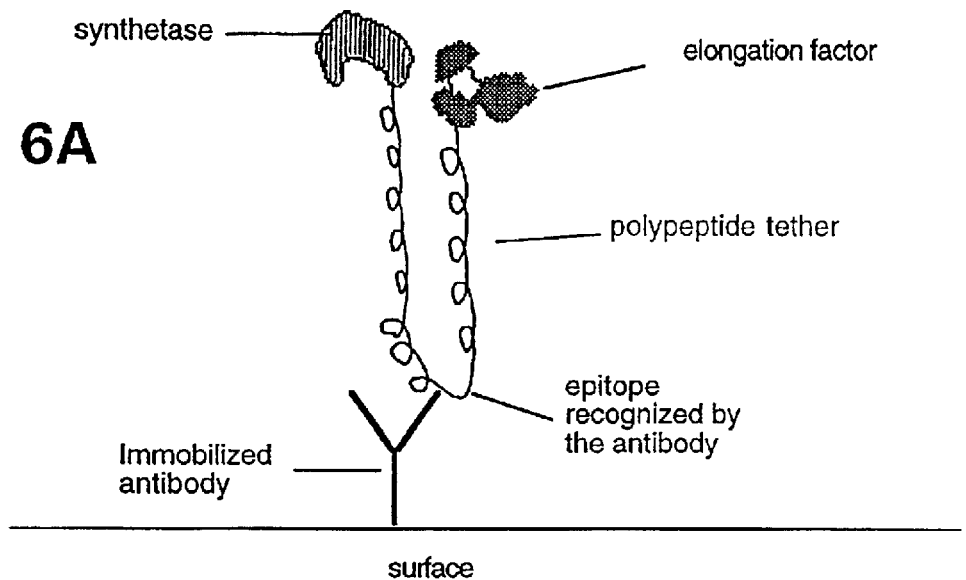
FIGS. 6A–6C illustrate three ways for the immobilization of amino acid analysis biorecognition elements onto surfaces as arrays, e.g., microwells, microchannels or microspots.

As shown in FIG. 6A, the synthetase and elongation factor can be co-immobilized to the surface using a single polypeptide tether which contains a defined epitope in the approximately central region. The epitope is bound by an antibody affixed to the surface of the assay locus at a known location. The antibodies may be arrayed onto surfaces using known methods (see, for example, Patel et al. (2000) *J. Biomater. Sci. Polym.* Ed. 11, 319–331; Morozov et al. (1999) *Anal. Chem.* 71,3110–3117; Lueking et al. (1999) *Anal. Biochem.* 270, 103–111).

Each of the 20 synthetases may be co-immobilized with elongation factors in this way having a different epitope tag recognized by a unique antibody for each of 20 synthetases. The 20 antibodies may then be arrayed at known positions at high spatial resolution. Hence, each of the 20 synthetase-elongation factor pairs will be immobilized at a known position by binding to its specific antibody. Functional groups for the covalent attachment of the peptide to the synthetase and elongation factor may occupy the N- and C-terminal positions of the peptide tethers. Amino and thiol groups are especially useful for the covalent attachment of proteins to surfaces including peptides. A suitable tether may therefore have amino groups (e.g., lysines) or thiol groups (e.g., cysteines) at the N-termini and C-termini. Suitable peptide tethers can be optionally be composed of polar amino acids and be flexible. For example, tethers composed of glycine and serine would be uncharged, polar and flexible. Commercially available crosslinking reagents will be useful in the conjugation the synthetases and elongation factors to tethers in some preferred embodiments.

Alternatively, using genetic engineering techniques well known to the art, one of ordinary skill can express the elongation factor and synthetases as fusion proteins which comprise a polypeptide tether. (for review see Nilsson, J et al. (1997) *Protein Expr. Purif.* 11, 1–16)

Preferably, the tether is composed of polar amino acids. For example, tethers composed of serine and glycine are flexible as well as polar. The polypeptide tether desirably contains binding motifs, domains or epitope tags recognized by antibodies for the immobilization of the fusion protein. Alternatively, the synthetases and elongation factors can be joined using bifunctional crosslinking reagents, including those with long polar spacer arms.

In one embodiment of the invention, the synthetase and the elongation factor are joined to a flexible polypeptide tether, in the central portion of which is an epitope recognized by an antibody. The synthetase and the elongation factor can be immobilized to the epitope's cognate antibody which itself is affixed to the surface of a well, array locus or microchannel used in the present invention. Alternatively, the epitope within the polypeptide tether chain can be unique for each particular synthetase, where there are twenty epitopic specificities and twenty antibodies specific thereto. Desirably, antibodies used for immobilization (or capture) are monoclonal antibodies. This embodiment is exemplified in FIG. 6A.

Use of Dual Tethers

Figure 6B:
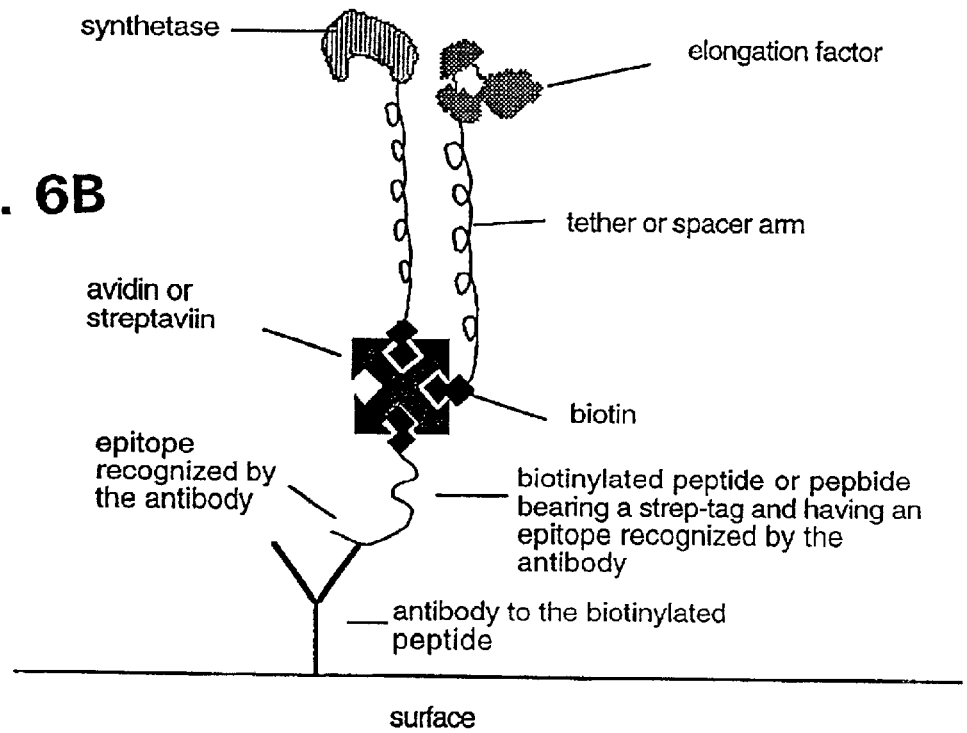

As shown in FIG. 6B the synthetase and elongation factor can each be joined to one end of a separate tether; the other end of which tether is bound to a biotin molecule. The biotin-avidin or biotin-streptavidin system thereby co-immobilizes the synthetases and elongation factor. Since each streptavidin has four binding sites for biotin, the streptavidin may be used to co-immobilize the elongation factor and synthetases in close proximity. This will facilitate the rapid capture of the AA-tRNAs formed by the synthetases by the co-immobilized elongation factor. In a preferred embodiment, flexible tethers or spacer arms will prevent steric problems and allow the immobilized proteins to interact with their macromolecular substrate.

In this alternative embodiment, each synthetase and the elongation factor are linked to one end of a tether or spacer arm, and there is a ligand at the other end of the tether or spacer arm. In a particular embodiment, the ligand at the end of the tether or spacer arm is biotin. The synthetase and elongation factor then bind via the ligand to the ligand binding partner (avidin or streptavidin in the case where the ligand is biotin). The ligand binding partner can be bound to an array locus, the interior of a microchannel or the bottom of a microwell. Alternatively, there can be an antibody affixed to the array locus, microchannel or microwell and to the antibody is bound a ligand-bearing polypeptide which also bears an epitope recognized by the antibody bound to the surface of the assay device. The ligand can again be biotin if the ligand binding partner is avidin or streptavidin or other biotin-binding molecule. See FIG. 6B for a diagrammatic representation of this particular embodiment. Avidin or streptavidin are desirable because each molecule therof can bind more than one molecule of biotin.

The biotin-streptavidin co-immobilized synthetase-elongation factor pair may be immobilized onto a surface including biosensor transducers. This may be achieved, for example, by binding to an immobilized biotin molecule. Alternatively, as shown schematically in FIG. 6B, a peptide bearing unique epitope may be conjugated to the streptavidin and used to immobilize the each of the 20 synthetase-elongation factor pairs on an array of 20 antibodies as described above. In an alternative approach, the avidin or streptavidin may be attached to the elongation factor or synthetases by making elongation factor-avidin or synthetase-avidin fusion proteins. The avidin fusion proteins may be constructed as taught in Airenne et al. (1999) *Biomol. Eng.* 16, 87–92.

Figure 6C:
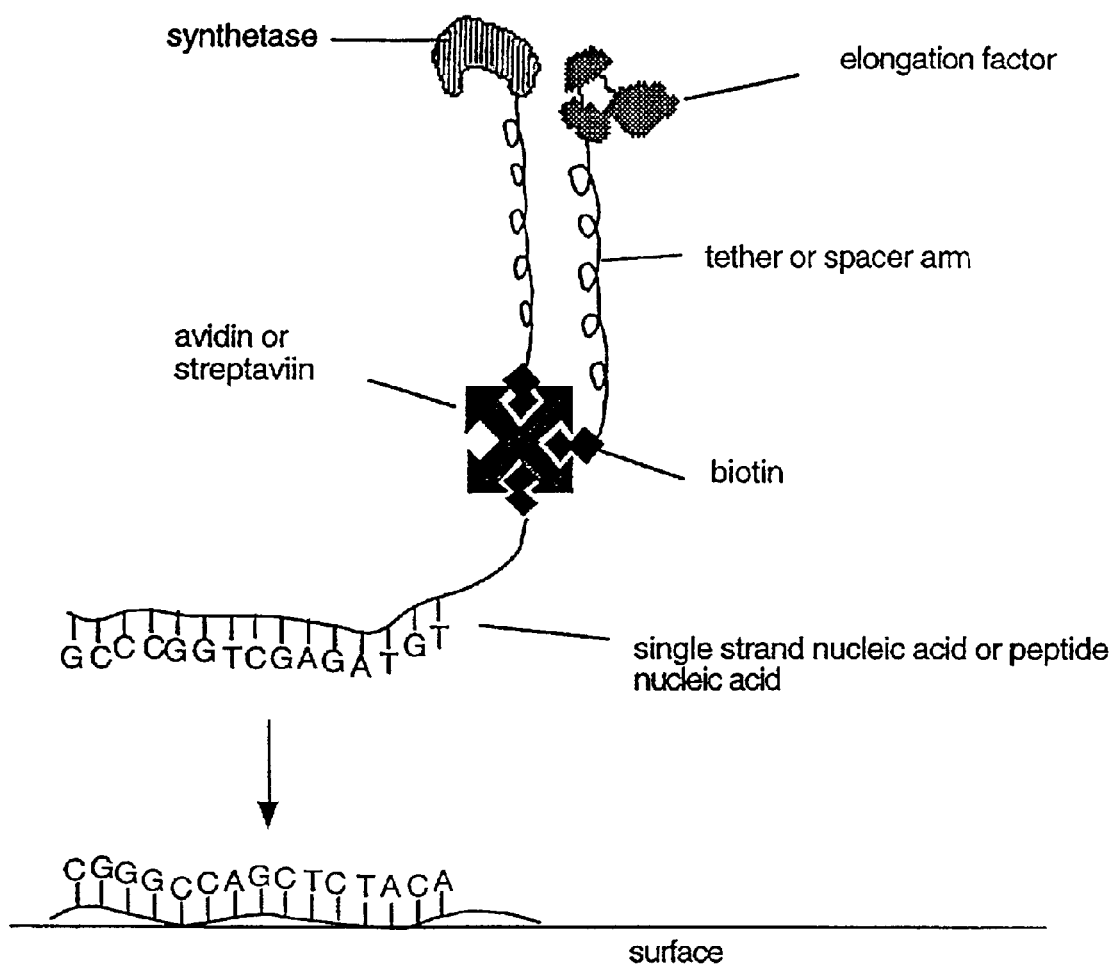

In another embodiment of the invention, each synthetase and the elongation factor are separately bound to one end of a tether or spacer arm, which is bound to a ligand at the end opposite the protein. The surface of the array locus, the microchannel or microwell contains a bound oligonucleotide. Binding of the synthetase and elongation factors to the array locus, microchannel or microwell is mediated by an oligonucleotide complementary to the surface bound oligonucleotide to which is bound a ligand. A ligand binding partner which can bind the ligands attached to the synthetase, elongation factor and oligonucleotide completes the attachment system. In a specific embodiment the ligand is biotin and the ligand binding partner is avidin or streptavidin. This system is shown in FIG. 6C.

The immobilization of the synthetase and/or the elongation factor to the supporting surface is by means of oligonucleotide hybridization. In this embodiment as shown, for instance, in FIG. 6C, a different oligonucleotide having a unique sequence is conjugated to the synthetase-elongation factor pairs. The conjugates are then arrayed at known positions by the hybridization of the conjugated oligonucleotides to their complimentary oligonucleotides which are immobilized onto surfaces in known positions. Methods for arraying oligonucleotides are well known to one of ordinary skill in the art.

Example 9

Example 9 describes both the use of continuous microflow assay formats with multiple detection methods for detecting the reaction product. These detection methods include the use of ELISA and fluorescent labeling detection methods with displacement of a labeled ligand by the reaction product. While both the continuous microflow assay format and the displacement methods are taught together in some of the embodiments, they also may be used separately.

FIGS. 7A–7B show two modes for ultrasensitive amino acid analysis in continuous microflow displacement systems. An array of 20 channels, each perfused with a separate reaction mixture containing a different synthetase, its cognate tRNA and EFTu:GTP, permits the continuous, simultaneous analysis of the 20 primary protein amino acids on a microscale. For simplicity, only one channel is shown. A ternary complex probe, a molecule or substance that specifically and reversibly binds the ternary complex, is immobilized in each reaction channel. A known density of labeled ternary complex is bound to the ternary complex probe. The ternary complex may be further stabilized by using a non-hydrolyzable GTP analog. Ternary complex probes can include, without limitation, antibodies, antibody fragments, oligonucleotides, peptide nucleic acids, proteins, peptides, carbohydrates ribosomes, ribosome fragments or any other substance binding the ternary complex and permitting a displacement assay. The reaction channels have an inlet for sample containing amino acids, an outlet, and the channels are in fluid connection with at least one reservoir. A reaction solution containing a synthetase, its cognate tRNA and EF-Tu:GTP is pumped continuously through each reaction channel by microfluidic pumping. A different synthetase and cognate tRNA along with EF-Tu:GTP is therefore pumped through each of the 20 reaction channels. The amino acid sample is pumped through the 20 reaction channel from a main channel or capillary in fluid connection with all 20 inlets. As the mixture of amino acids flows into the reaction channel array, amino acids having a cognate synthetase and tRNA in each reaction channel are converted into AA-tRNAs which then bind the EFTu:GTP to form a stable ternary complex (EF-Tu:GTP-AA-tRNA). The newly formed ternary complex then displaces a proportionate amount of labeled ternary complex that is reversibly immobilized in each microchannel. The displaced labeled ternary complex then flows past an integrated and computer controlled spatially specific detector and is continuously detected.

The amino acid containing sample (e.g., in one embodiment a protein of interest is sequentially degraded using an aminopeptidase or a carboxypeptidase in a reaction chamber separated from the flow channel by a selectively permeable membrane or filter as described above wherein amino acids pass, but polypeptides greater than 6 kDa do not) joins a flow stream which contains at least one aminoacyl tRNA synthetase and a cognate tRNA. EF-Tu:GTP is added to the reaction channel from the same reservoir as the synthetase or tRNA or from a different reservoir in fluid connection with the reaction flowchannel. The amino acids entering the flowchannel through the amino acid inlet are contacted with the aminoacyl tRNA synthetases. Amino acids specific for the cogante synthetase and tRNA n each channel are converted into a proportionate amount of AA-tRNA.

In certain preferred aspects, labeled AA-tRNAs are reversibly bound in the microflow channel by a molecule that binds AA-trNAs (e.g., AA-tRNA specific antiboides, or AA=-specific elongation factors, or oligonucleotide aptamers) and permits a displacement assay. The newly formed AA-tRNAs will displace a proportionate amount of labeled tRNAs from the channel. The displaced labeled AA-tRNAs will flow past the detector. The detector will depend on the nature of the label. For fluorescent labels, a laser and fluorescence detection will be used.

In another continuous displacement format the newly formed AA-tRNAs are contacted with EF-Tu:GTP which may be introduced into the channel in appropriate buffer strength through a separate flow inlet downstream, from a separate reservoir and flowed by fluidic pumping. The AA-tRNAs bind to the EF-Tu:GTP the microflow passage forming a ternary complex (EF-TU:GTP in the microflow pasage foraig teF-Tu:GTP-AA—tRNA). The newly formed ternary complex displaces a proportionate amount of reversibly absorbed labeled ternary compex that is bound in the microflow passage.

In FIG. 7A a continuous microflow ELISA for amino acid analysis is described. These systems may be configured to measure a single amino acid and in multiple amino acids by having an array of channels and an array of detectors. In this embodiment, the ternary complex is labeled with an enzyme that can catalyze an amplification reaction (e.g., one enzyme molecule yields many detectable product molecules). Enzymes may be used that convert a nonfluorescent substrate into a fluorescent product. Alternatively, enzymes that produce luminescent or electrogenic products may be employed. Enzymes that may be used to label the ternary complex (or ternary complex probes) include, but are not limited to, alkaline phosphatase and horseradish peroxidase. Examples of fluorogenic substrates for alkaline phosphatase include Attophos and 5-fluorosalicyl phosphate. A fluorogenic substrate for horseradish peroxidase is 3-p-hydroxyphenyl-propionic acid. Alkaline phosphatase and horseradish peroxidase may also be used as enzyme labels for electrogenic and chemiluminescent substrates. For alkaline phosphatase and horseradish peroxidase 1,2-dioxetane arylphosphate, and 4-iodophenol-enhanced luminol are excellent chemiluminescent substrates and achieve attomole-zeptomole detection limits. As shown, the enzyme labeled ternary complex is reversibly immobilized in the reaction channel by binding to the immobilized ternary complex probe. A reaction mixture containing a specific synthetase, its cognate tRNA, and EF-Tu:GTP is continuously pumped through each reaction channel by microfluidic pumps. As the amino acid sample enters the reaction channel array, as described above, the amino acid having a cognate synthetase and tRNA in each channel will be converted into a proportionate amount or ternary complex that will displace a proportionate amount of enzyme labeled ternary complex.

The displaced labeled ternary complex flows down stream where the flow is joined by a second flow stream. This second flow contains the substrate for the enzyme label in reaction buffer and is transported from a separate reservoir in fluid connection with the reaction by microfluidic pumping as shown. The reaction products of the enzyme label are continuously detected down stream by an integrated spatially specific detector(s). The type of detector will depend on the enzyme substrate used. For example, if a fluorogenic substrate is employed laser induced fluorescence detection may be achieved using a confocal scanner or CCD detector. With spatially specific detectors, the amino acids will be identified by the position of the channel sending the signal to the detector. The 20 amino acids will thereby be identified and quantitated.

FIG. 7B shows an ultrasensitive amino acid analyzer using a continuous microflow displacement format and laser induced fluorescence detection. Multiple labels may be used to increase the sensitivity of the assay. Labeled ternary complex is reversibly immobilized in each reaction channel and each reaction channel has an amino acid inlet, an outlet, and is in fluid connection to a unique reservoir containing a specific synthetase, cognate tRNA, and EF-Tu:GTP as described above. As the amino acid sample flows through the reaction channel(s) each amino acid reacts with its synthetase and cognate tRNA forming AA-tRNAs that bind the elongation factor forming a ternary complex. The newly formed ternary complex will displace a proportionate amount of fluorescently labeled ternary complex, which will flow down stream and pass through a laser beam. The emission light will pass through optical filters and be continuously detected using a spatially specific detector (e.g., high-sensitivity CCD camera) linked to a computer. The amount of amino acid cognate to the synthetase and tRNA in each channel will be proportional to the amount of fluorescent label flowing past the detector. Since each microchannel is perfused with a different one of the 20 synthetase and its cognate tRNA, each reaction channel will signal a different amino acid, the one cognate for the synthetase and tRNA present. The location of each channel in the array will allow the identification of the 20 amino acids. A spatially specific detector such as a high-sensitivity CCD camera or a confocal scanner will permit spatially resolved detection of the 20 amino acids simultaneously and continuously with a sensitivity orders of magnitude greater that current amino acid analyzers. Indeed, fluorescently labeled molecules have been detected quantitatively in continuous flow at the single molecule level.

Example 10

Example 10 describes the systems and methods of a general microarray assay as exemplified with the use of epifluorescent labeling and a CCD camera. The systems include the microarray, the CCD camera, and a computer for processing the camera signal according to the array position of the light source.

In a microarray embodiment of the invention, each of the twenty aminoacyl tRNA synthetases or the twenty tRNAs are spotted at a known position on a microchip or other surface as part of a high density array. EF-Tu:GTP, tethered biotin and streptavidin are bound with the synthetases on the chip. Then, sample containing amino acid from one stage of exoprotease digestion, together with the tRNA or synthetase, is applied to the chip and the free amino acid is converted to the aminoacyl tRNA and then to the AA-tRNA-EF-Tu:GTP complex on the surface of the chip at the spot on the array wherein the cognate tRNA is located. The array is observed using a CCD-camera mounted on an epifluorescence microscope. Signals from the CCD-camera are decoded by a computer to which the readout is coupled. The carboxypeptidases can be arrayed to the wells as separate microspots. Alternatively, the protein substrates that are coimmobilized to the exopeptidase on particles can be placed into the microwells.

Figure 8A:
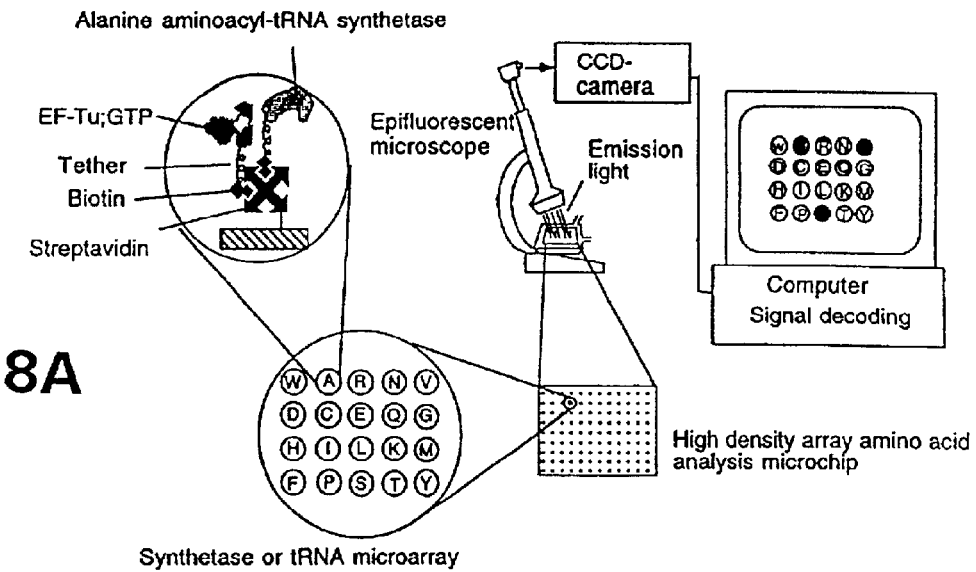
FIGS. 8A–8D illustrate an application of microarray technology to amino acid analytical methods of the present invention.

FIG. 8A shows one such embodiment in which an epifluorescent microscope and a CCD camera detect the light emitted in the assay by individual spots of defined location on a high density array amino acid analysis microchip. A linked computer decodes the signals to provide the amino acid quantitative data/or sequence analysis data when the arrays of the invention are used to analyze samples containing at least one of the primary amino acids. Arrays may optionally be covered with a membrane (e.g., a microdialysis membrane) having a molecular weight cutoff that allows free passage to amino acids but is impermeable to macromolecules. Alternatively, peptides or small proteins to be sequenced are conjugated to a surface (e.g., a polymer such as dextran) to prevent their passage through the membrane.

Figure 8B:
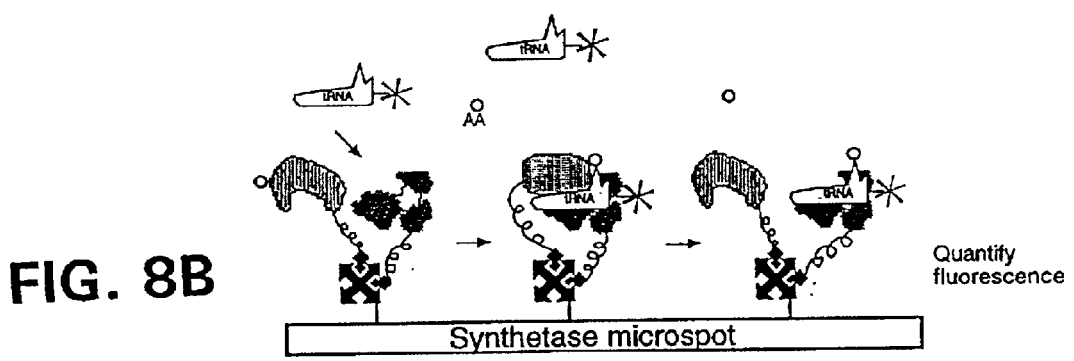
Figure 8C:
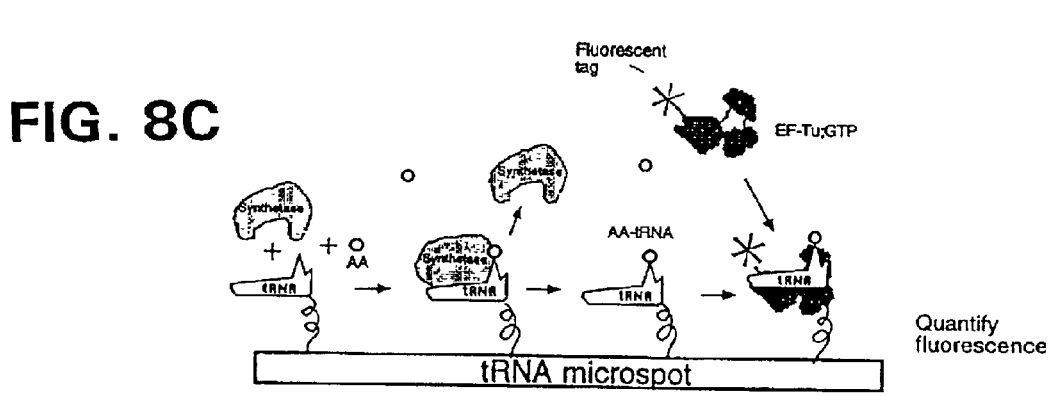

As shown in FIG. 8B, fluorescently labeled tRNAs may be captured in the synthetase arrays or, as shown in FIG. 8C, fluorescently labeled elongation factors may be captured in tRNA microarrays. FIG. 8B shows an embodiment where each synthetase and the elongation factor are indirectly immobilized as microspots via a ligand-ligand binding system. FIG. 8C shows an embodiment in which 20 tRNAs, one specific for each of the protein amino acids, are arrayed as microspots. Amino acids in the sample are attached to the tRNAs by their cognate synthetases, and fluorescently labeled EF-Tu:GTP binds the arrayed AA-tRNAs.

The arrays can be patterned on the surfaces of optical waveguides, and evanescent wave excitation can be employed for excitation of captured fluorescent probes.

The formation of the EF-Tu:GTP-AA-tRNA ternary complexes may be followed continuously by following the position-dependent increase in fluorescence on the waveguide surface using a CCD detector. Alternatively, the excitation and emitted light can be transported to/from each microspot through optical fibers. The emission light passes through optical filters and can be imaged through a microscope objective to a CCD detector for continuous detection.

A sample may also comprise an exopeptidase digestion buffer containing the protein to be sequenced and the exopeptidase (e.g., carboxypeptidase(s) for C-terminal sequencing) are placed on the membrane over each array.

Figure 8D:
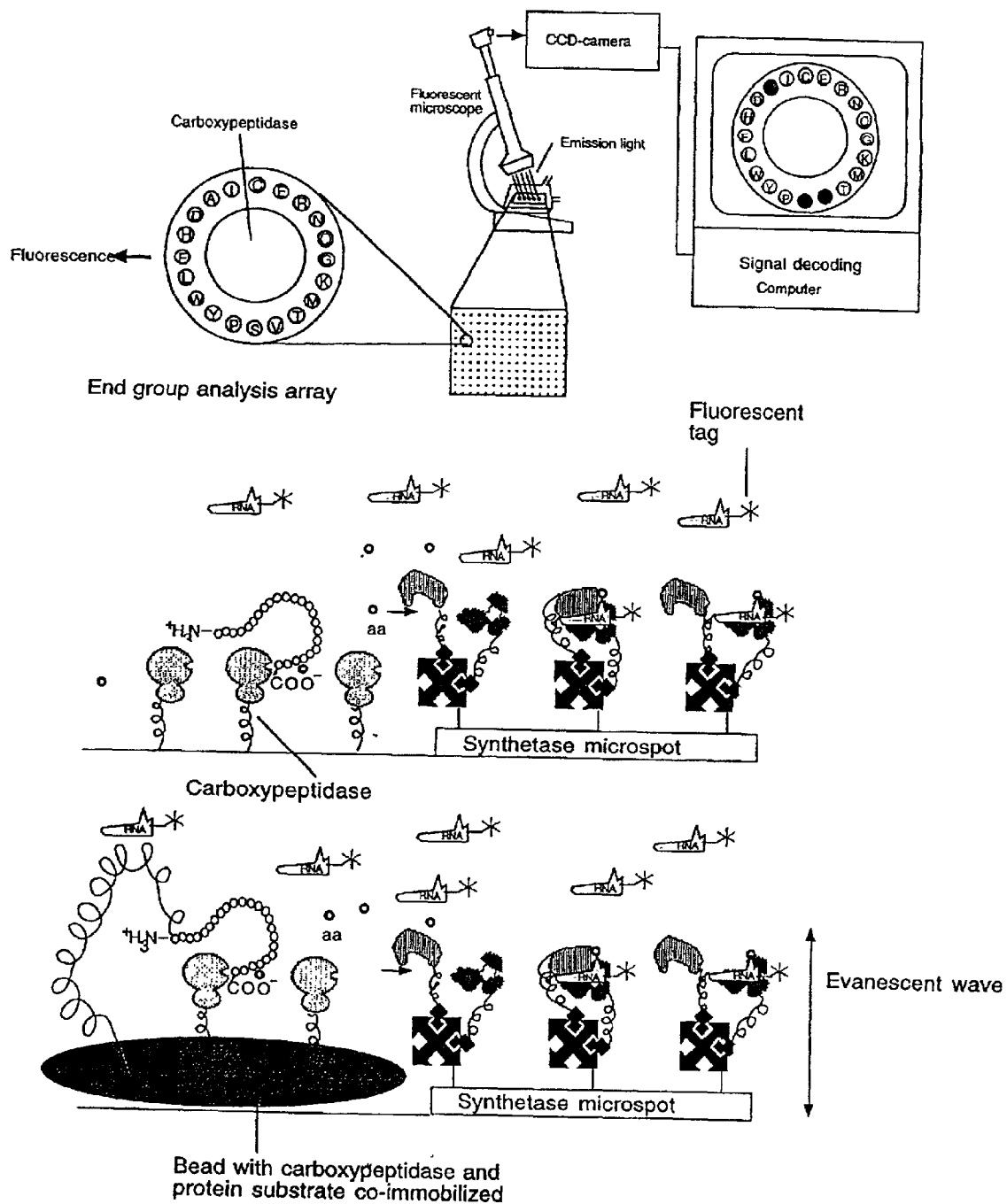

FIG. 8D illustrates another embodiment of a high density C-terminal end group analysis microarray. The 20 aminoacyl-tRNA synthetases are coimmobilized with the elongation factor to a different microspot. The carboxypeptidases are immobilized to a different zone on the same surface, and the protein substrate is added to each well by a nanopipetting robot. Liberated amino acids are converted to AA-tRNAs and captured on the surface of each microspot and the amount of AA-tRNA on each spot is quantified by fluorescence detection. Alternatively, the carboxypeptidases and protein substrate are immobilized to a bead that is placed in the synthetase array as also shown schematically in FIG. 8D. Evanescent wave excitation can be employed so that the formation of the ternary complex on the microspots is monitored continuously without a wash step.

Example 11

Example 11 describes the use of a labeled-compound displacement assay format to measure a product of the aminoacyl tRNAsynthetase reaction.

The reaction channels have an inlet for sample containing amino acids, an outlet, and the channels are in fluid connection with at least one reservoir. A reaction solution containing a synthetase, its cognate tRNA and EF-Tu:GTP is pumped continuously through each reaction channel by microfluidic pumping. A different synthetase and cognate tRNA along with EF-Tu:GTP is therefore pumped through each of the 20 amino acid specific reaction channels. The amino acid sample is pumped through the 20 reaction channel from a main channel or capillary in fluid connection with all 20 inlets. As the mixture of amino acids flows into the reaction channel array, amino acids having a cognate synthetase and tRNA in each reaction channel are converted into AA-tRNAs which then bind the EF-Tu:GTP to form a stable ternary complex (EF-Tu:GTP-AA-tRNA).

The newly formed ternary complex then displaces a proportionate amount of labeled ternary complex that is reversibly immobilized in each microchannel. The displaced labeled ternary complex then flows past an integrated and computer controlled spatially specific detector and is continuously detected.

This system permits the continuous, simultaneous analysis of the 20 amino acids on a microscale. A ternary complex probe, a molecule or substance that specifically and reversibly binds the ternary complex, is immobilized in each reaction channel. A known density of labeled ternary complex is bound to the ternary complex probe. The ternary complex may be further stabilized by using a nonhydrolyzable GTP analog. Ternary complex probes can include, without limitation, antibodies, antibody fragments, oligonucleotides, peptide nucleic acids, proteins, peptides, carbohydrates, ribosomes, ribosome fragments or any other substance binding the ternary complex and permitting a displacement assay.

Figure 9:
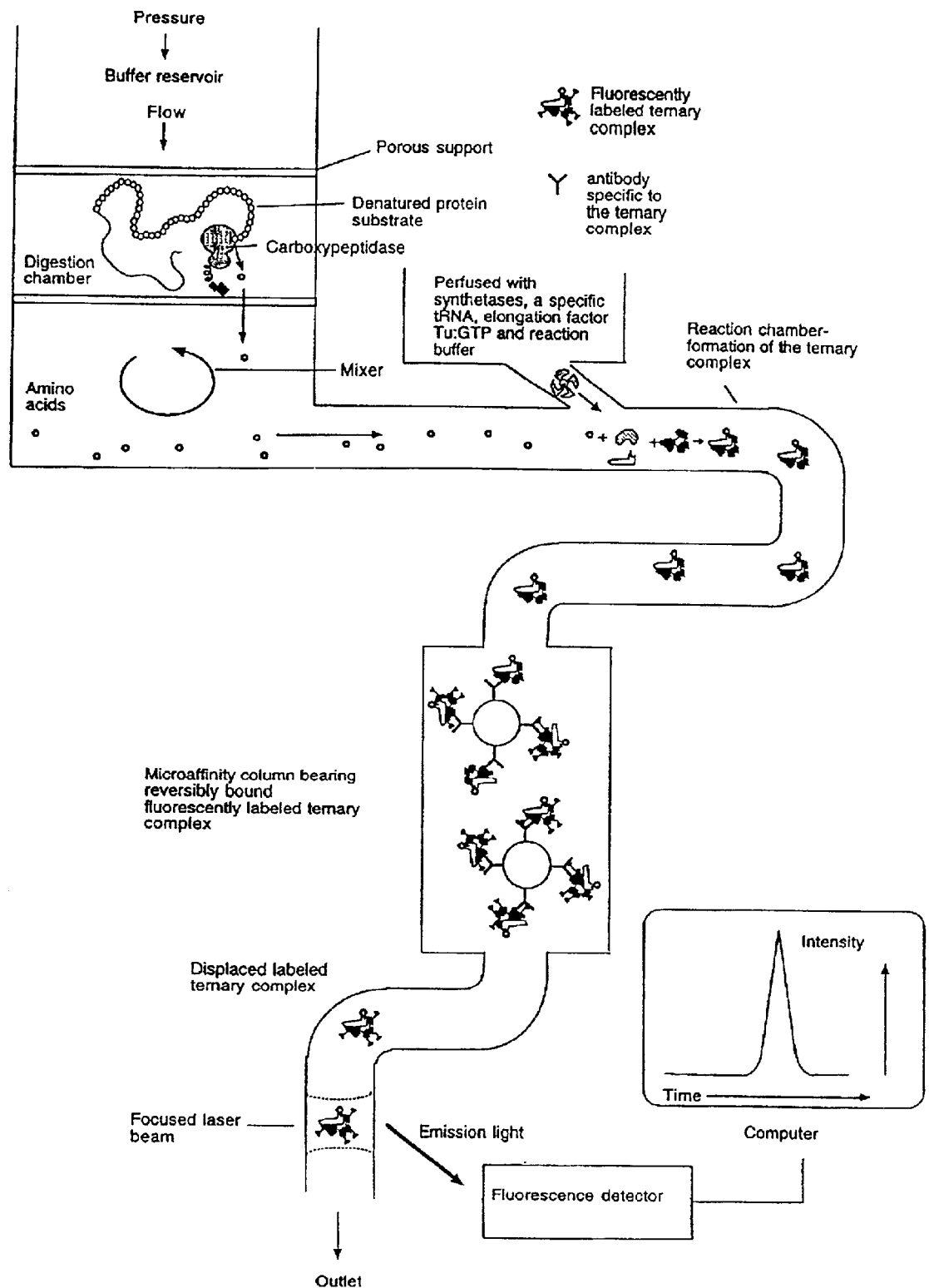
FIG. 9 schematically illustrates an integrated microsystem for end group protein sequencing using a continuous flow displacement scheme for amino acid analysis.

The method is exemplified, as shown in FIG. 9, in the analysis of an amino acid sample provided by the digestion of a protein by an aminopeptidase or, as in this example, a carboxypeptidase. FIG. 9 schematically illustrates an integrated microsystem for end group protein sequencing using a continuous flow displacement scheme for amino acid analysis. An array of 20 amino acid specific microfluidic reaction channels is employed to detect and quantitate the 20 protein amino acids. For the sake of simplicity, only one reaction channel is shown in the figure. In each reaction channel a known density of ternary complex probe (e.g. an antibody that specifically recognizes the ternary complex) is immobilized and saturated with fluorescently labeled ternary complex. Alternatively, the ternary complex is immobilized and saturated with a fluorescently labeled ternary complex antibody. Each reaction microchannel is perfused with a reaction solution containing a different one of the 20 synthetases, its cognate tRNA and the elongation factor complexed with GTP (or a nonhydrolyzable GTP analog). Each of the 20 reaction solutions is transported from a separate reservoir that is in fluid connection with a reaction channel by microfluidic pumping.

Each of the amino acid specific reaction channels has an inlet in fluid connection to a main channel or chamber. As shown, carboxypeptidase digest of the protein substrate is carried out in an enclosed ultrafiltration membrane placed in a flow stream. The membrane is impermeable to macromolecules but allows free passage of amino acids. As amino acids enter the reaction channels, those amino acids having a cognate synthetase and tRNA in each channel are converted into a proportionate amount of AA-tRNA which then binds the elongation factors, forming the ternary complex (AA-tRNA-EF-Tu:GTP). This newly formed ternary complex displaces a proportionate amount of the reversibly bound fluorescently labeled ternary complex, the displaced complex then flows through a laser beam to excite the fluors, and the fluorescence is continuously detected.

A spatially specific detector (e.g. a high-sensitivity CCD detector) integrated with a computer continuously records the emission light intensities in all channels. The record of the displaced fluorescently labeled ternary complexes going through the focused laser beam in each of the channels is recorded, and the computer in communication with the detector transforms this data to compute the amino acid sequence of the protein.

Each detection flow chamber is perfused with aminoacylation buffer containing the twenty aminoacyl tRNA synthetases, EF-Tu:GTP and a tRNA specific for one particular amino acid. Amino acids enter the chamber under pressure from a mixed chamber. An amino acid having a cognate tRNA in the chamber is converted to a proportionate amount of the ternary complex which then flows to the microaffinity column and causes displacement of a proportionate amount of labeled ternary complex from the solid support within the column. The displaced, labeled ternary complexes are carried by flowing buffer and detected downstream by a fluorescence detector, or other detector as appropriate to the label used. Depending on the instrumentation, for example, by using multiple fluorescent tags and multiple rounds of laser-induced fluorescence, it is possible to detect a single molecule.

The record of the labeled ternary complexes using known concentrations of unlabeled antigen is established so that unknown concentrations of newly formed ternary complex can be quantitated. Displacement efficiencies are established and optimized by using known concentrations of the ternary complex.

Bioaffinity molecules that bind that ternary complex with high specificity and have a high dissociation rate constant can be selected to create rapid, ultrasensitive biosensors. Highly sensitive, continuous flow immunosensors can detect analytes concentrations in the picomole range in less than one minute (Kusterbeck et al. (1990) *J. Immunol. Meth.* 135:191–197).

Example 12

Example 12 describes an apparatus for amino acid analysis and end group protein sequencing in an integrated microfluidic system where a CCD detector serves as an active support to quantitatively detect and image the distribution of labeled target molecules near the spatially addressable pixels. Binding of fluorescently or radiolabeled AA-tRNAs to elongation factors will be continuously detected with integrated data acquisition and computation to generate a sequence. This arrangement will provide an ultrasensitive, spatially specific detection with integrated data acquisition and computation. The microchip detector will detect luminescent and radioisotope reporter groups with high sensitivity in a spatially resolved manner.

Figure 10:
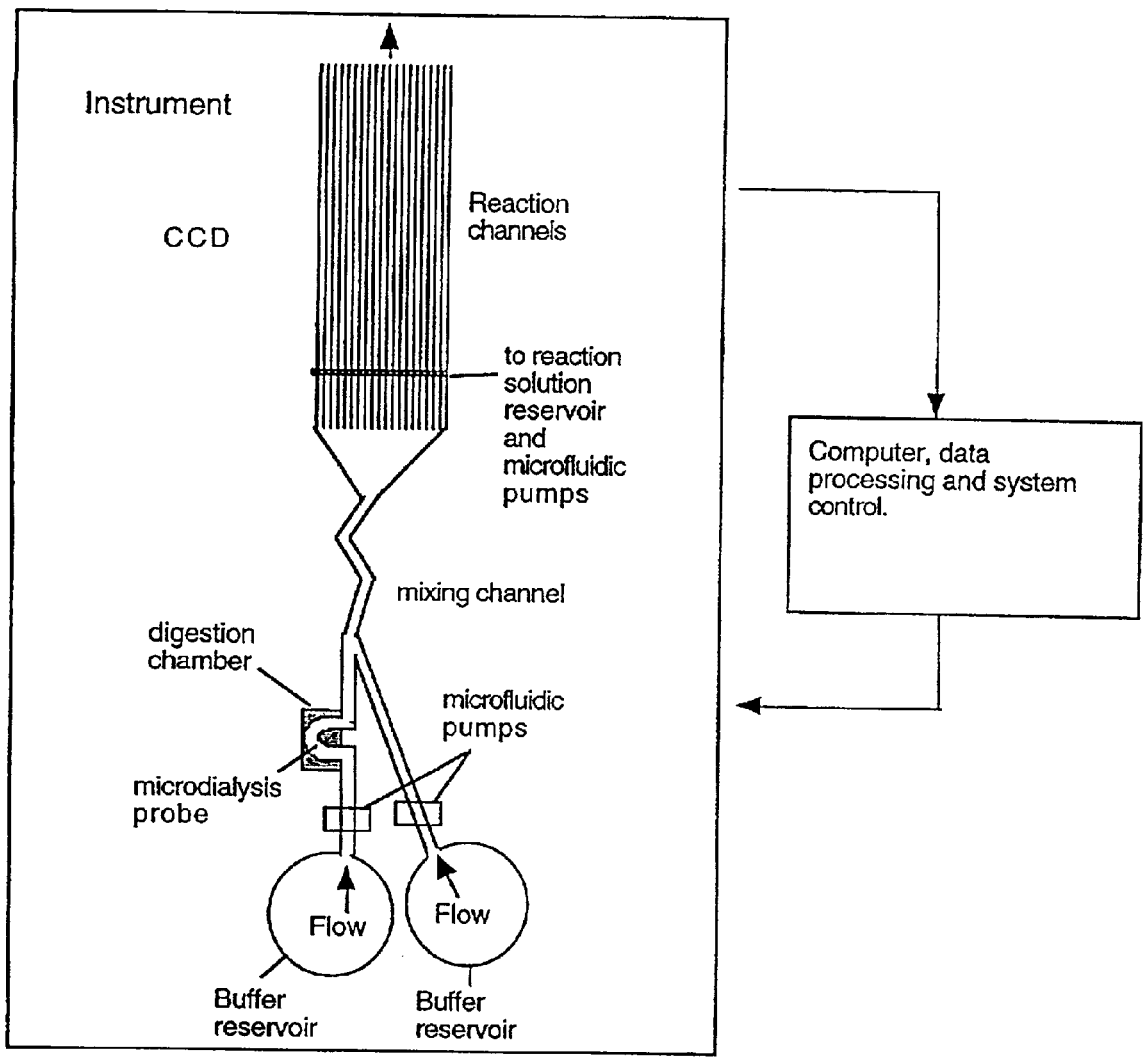
FIG. 10 is a diagram of an apparatus for amino acid analysis and end group protein sequencing in an integrated microfluidic system where a CCD detector serves as an active support to quantitatively detect and image the distribution of labeled target molecules near the spatially addressable pixels.

FIG. 10 is a diagram of one such computer-controlled and system for amino acid analysis and end-group sequencing using a CCD detector as an active solid support. Each locus in the array contains bound molecules necessary for the immobilization and detection of a particular AA-tRNA-EF-Tu:GTP ternary complex at a particular spot. The address within the array conveys the identity of the particular amino acid.

As set forth in FIG. 10, the system provides two buffer reservoirs. The first reservoir holds the digestion buffer solution. This solution is pumped via microfluidic pump through the digestion chamber. In the chamber, the protein of interest is contacted with an aminopeptidase or carboxypeptidase under reaction conditions leading to the cleavage of the respective end terminal amino acids. These amino acids then pass through the molecular sieve of the digestate probe and enter the buffer flowing from reservoir where it flows to the mixing channel. This flow represents a sampling of the protein digestion chamber contents.

The second buffer reservoir is a source of solution providing fluorescently labeled tRNAs, ATP, and other reagents to support the aminoacyl tRNA synthetase formation of aminoacyl tRNAs. This solution is pumped via the microfluidic pumps to the mixing channel where it mixes with the flow coming from the digestion chamber. The mixture then is distributed to the reaction channels.

There are separate reaction channels. Each reaction channel contains one aminoacyl tRNA synthetase immobilized to the channel surface and in contact with the reaction mixture. Each immobilized aminoacyl tRNA synthetase is located in a known channel. The reactants flowing therein contact the particular aminoacyl tRNA synthetase and the amino acid corresponding to the synthetase immobilized in the channel is converted to the corresponding aminoacyl tRNA.

Elongation factor is immobilized on the interior surface of the microchannel. When a labeled AA-tRNA flows by and is captured on the surface by the immobilized elongation factor, there is continuous signal generation, and a CCD detects the signal and the data are fed to a computer. The computer identifies the amino acid according to the known location of the corresponding synthetase. The strength of the signal indicates the amount of the aminoacyl tRNA formed and the relative amount thereby of the primary protein amino acid released during the digestion of the protein.

While the above example exemplifies the use of an array of immobilized synthetases, one of ordinary skill in the art would appreciate the possibility of an array based upon immobilizing the primary protein amino acid tRNAs rather than the corresponding synthetases. In such a format, the elongation factor can be fluorescently labeled to detect the aminoacyl tRNA product. The florescence intensity associated with each channel can be continuously monitored and decoded so as to provide quantitative amino acid composition or amino acid sequence information. Proteins and RNAs can be engineered to give appropriate dissociation constants using known methods.

Figure 11:
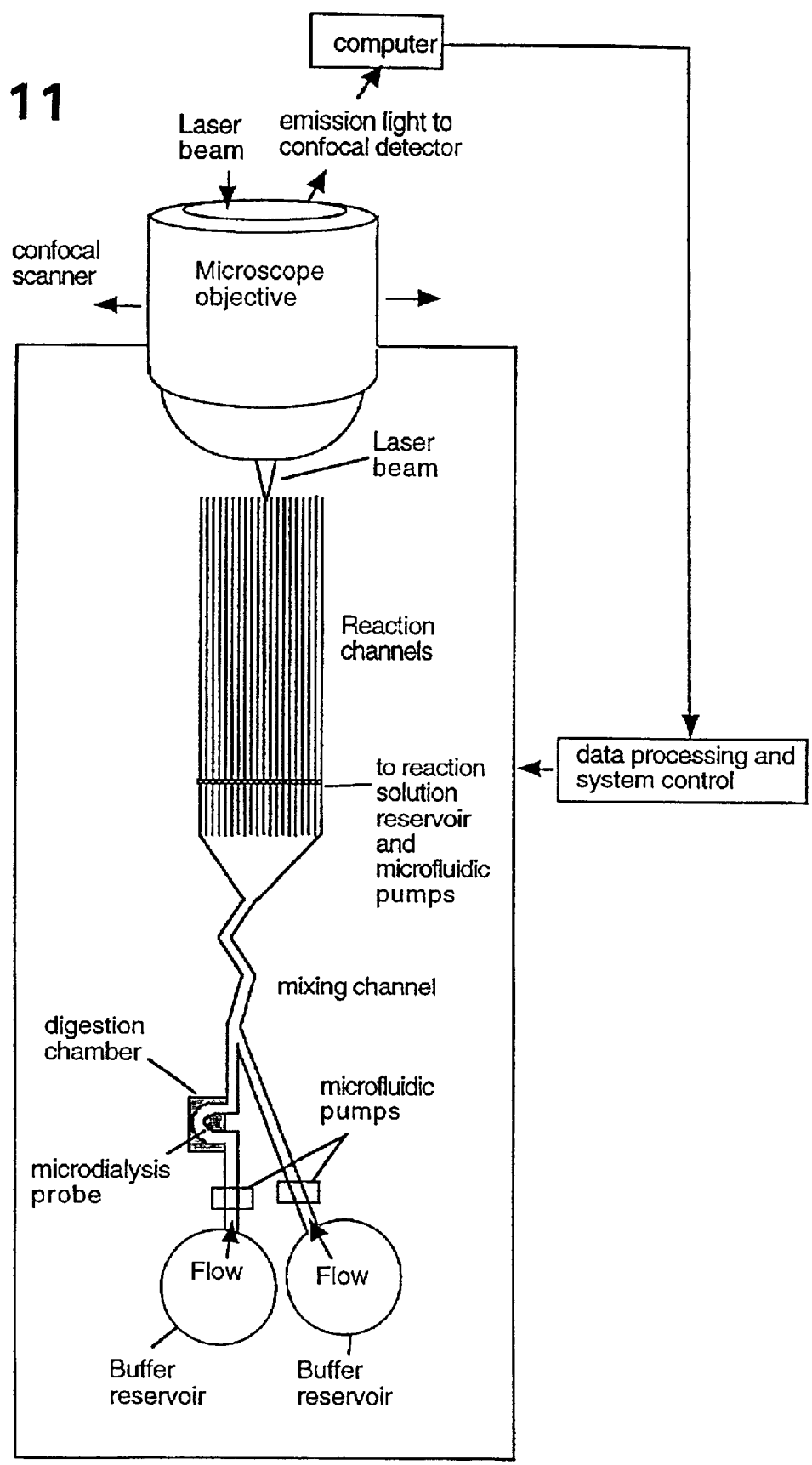
FIG. 11 is a diagram of an apparatus for amino acid analysis in which a confocal scanner is used to detect signal information in the microchannels.

FIG. 11 provides a similar arrangement wherein the detection is by a microscope objective attached to a confocal scanner. In this embodiment for protein end group and amino acid sequence analysis a confocal scanner serves as the detector for the signal associated with the AA-tRNA-EF-Tu:GTP ternary complex. The change in fluorescence is monitored in each of the twenty microflow channels, after laser beam excitation, in the case of a fluorescent label, to follow the reactions catalyzed by the synthetases in a spatially resolved manner.

Example 13

Figure 12A:
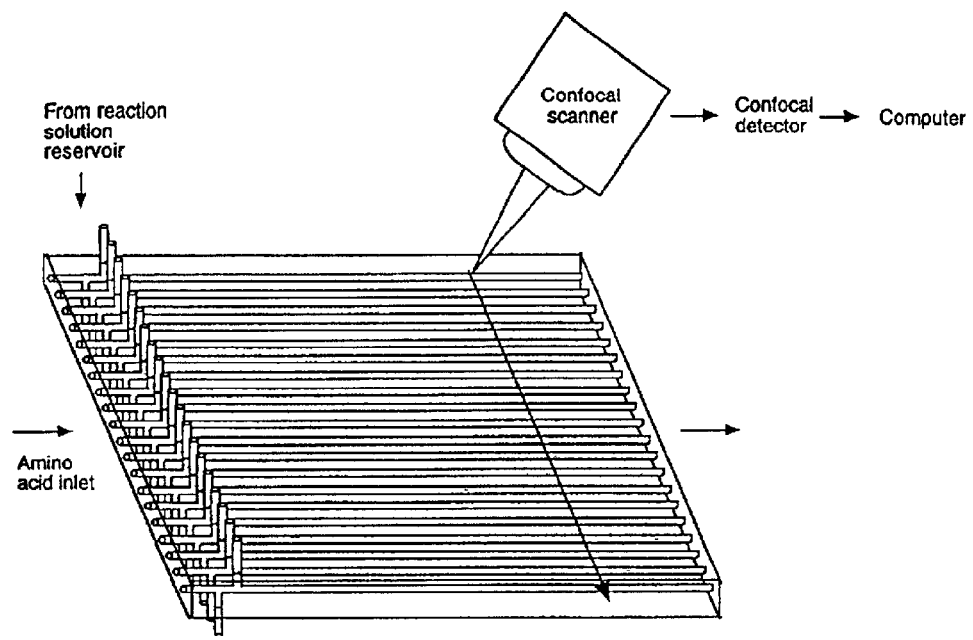
FIGS. 12A and 12B are schematic drawings of a microflow system for amino acid analysis using an integrated computer controlled wash step and a laser scanner and fluorescent detector.
Figure 12B:
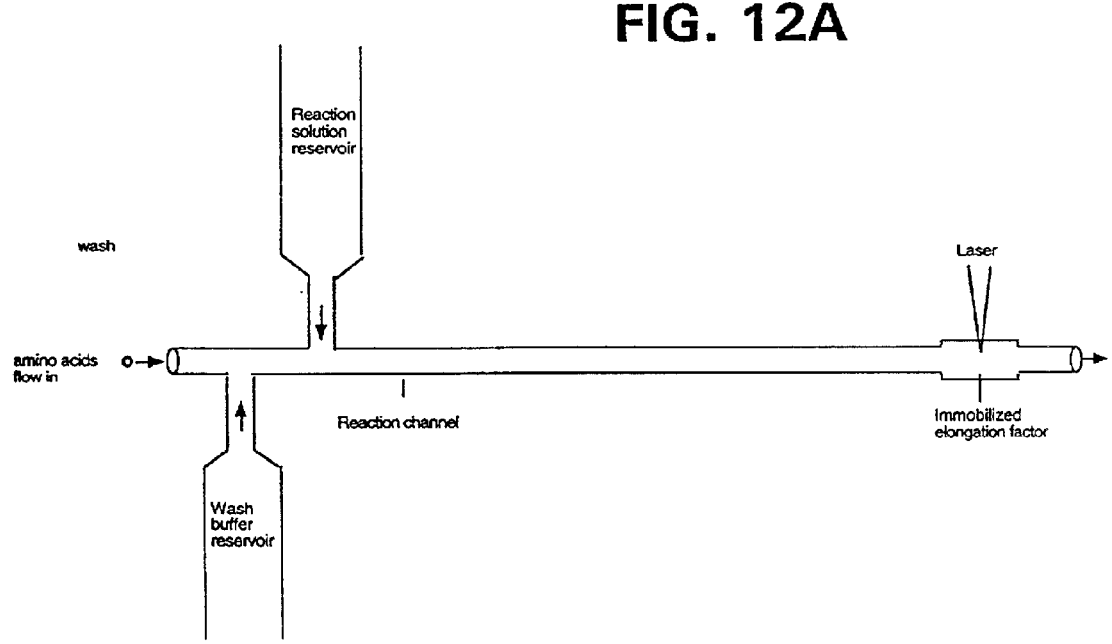

Example 13 describes a microflow system of microcapillaries for amino acid analysis using an integrated computer controlled wash step and a laser scanner and a fluorescent detector. FIGS. 12A and 12B are schematic drawings of such a system.

FIG. 12A provides a schematic of the confocal scanner system, and 12B illustrates the connections of a single microchannel within the twenty microchannel array, together with the inlets for the samples containing the amino acids, the wash buffer and the reaction solution. Computer controlled microfluidic pumps and valves are employed to periodically switch from reaction buffer to wash buffer before the immobilized capture reagent is excited by the laser to generate and read the fluorescent signals form the captured fluorescently labeled molecule over time.

As illustrated in FIGS. 12A and 12B, the biosensor array consists of 20 reaction microcapillaries or microchannels. Each reaction microcapillary has an inlet for amino acids to flow into and an outlet and is connected to a different reservoir by a microcapillary. Each reservoir contains the 20 synthetases and a fluorescently labeled tRNA specific for a different amino acid. (Alternatively, each reservoir can contain one synthetase and a fluorescently labeled cognate tRNA). The reaction solutions are continuously transported through the reaction capillaries (e.g., by continuous-flow micropumps). EFTu:GTP is immobilized downstream in each reaction channel and used to capture and detect the fluorescently labeled AA-tRNAs. A laser beam is focused on the immobilized EF-Tu:GTP. For example, EF-Tu:GTP can be immobilized to optical fibers placed in each reaction channel. It is possible to selectively excite and detect fluorescence from the immobilized AA-tRNA-EF-Tu:GTP complexes even in the presence of high concentrations of fluorescently labeled tRNAs in the bulk solution (e.g., using evanescent wave excitation). As amino acids cognate for the fluorescently labeled tRNA in each channel flow through, a proportionate amount of fluorescently labeled AA-tRNA is formed. The newly formed AA-tRNAs are captured downstream by the immobilized elongation factor. When AA-tRNAs bind to the immobilized elongation factor, laser light in the evanescent wave excites the fluorophore, generating a signal.

GTP bound elongation factor binds AA-tRNAs but the GDP bound elongation factor does not. Accordingly, the AA-tRNAs may be eluted with a buffer containing GDP in order to reactivate the immobilized elongation factor-based sensor with a regeneration buffer containing GTP. This elution method has been used to affinity purify AA-tRNAs on immobilized EF-Tu:GTP (Chinali, G. (1997) *J. Biochem. Biophys. Meth.* 34:1–10). Other suitable elution systems contain high salt, e.g., 1 M NaCl.

Figure 12C:
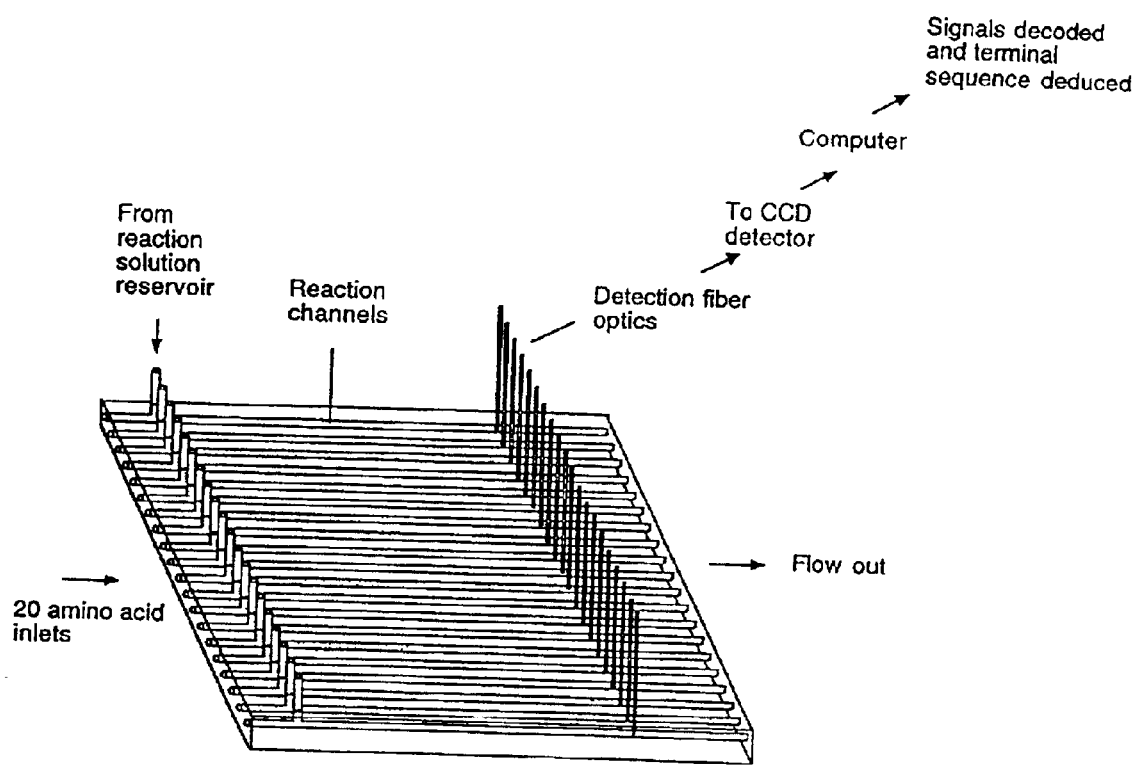
FIG. 12C provides a schematic summary of amino acid analysis using microchannels and detection of fluorescent light using optical fibers to deliver the evanescent wave excitation and carry the emission light to the detector.

FIG. 12C provides a schematic summary of amino acid analysis using microchannels and detection of fluorescent light using optical fibers to deliver the evanescent wave excitation and carry the emission light to the detector. The elongation factor:GTP is immobilized to the tips of 20 optical fibers, and each fiber is inserted into a different reaction channel, each of which is specific for a particular one of the 20 primary amino acids. Each channel is in fluid connection with a different reservoir from which a reaction mixture containing a different synthetase, and fluorescently labeled tRNA as described above. As the sample containing amino acids flows into the reaction channel array, the amino acid having a cognate synthetase and tRNA in the channel is converted into fluorescently labeled AA-tRNA which then binds the elongation factor immobilized on the optical fibers. Upon excitation with a light of the appropriate wavelength, for example, laser light, the signal generated are quantitatively analyzed continuously by fluorescent detection. The signals from the optical fibers may be imaged through a microscope objective onto a CCD detector integrated with a computer where the signal information is decoded and amino acid quantities and/or sequence is generated.

Additional microflow formats are also within the scope of the present invention. For example, a synthetase (see FIG. 5B) or tRNA (one specific for a different amino acid) can be immobilized in the amino acid specific reaction channels. Alternatively, an amino acid biosensor array (e.g., optical fiber or microelectrode) can be placed in a flow stream and detect amino acids as they flow through the array (see FIG. 5C).

Other methods for following the reaction of each amino acid with its cognate synthetase in spatially resolved microflow or microwell formats are suggested. Fluorescent tags may be attached to the synthetases and the change in fluorescence as the synthetase binds its cognate amino acid is monitored.

In other embodiments, the molecule that specifically binds AA-tRNAs (e.g., EF-Tu:GTP) is fluorescently labeled and the change in fluorescence caused by the binding to the AA-tRNA is monitored to follow the reaction. The elongation factor may be conveniently fluorescently labeled, for example, by using a fluorescently labeled GTP analog.

Example 14

Scintillation proximity assays are envisaged for amino acid analysis. In scintillation proximity assays a radioisotope is used as an energy donor and a scintillant-coated surface (e.g., a bead) is used as an energy acceptor. Scintillation proximity assays (SPA) are described in U.S. Pat. No. 4,568,649 which is incorporated herein by reference. These assays are reviewed in Alouani (2000) *Methods Mol Biol* 138: 135–41. The EF-Tu:GTP can be bound to SPA beads (commercially available from Amersham Corp., Amersham Place, Little Chalfont, England). For example, biotinylated elongation factors may be conjugated to avidin or streptavidin coated SPA beads which are commercially available.

Biotin in the form of N-hydroxysuccinimide-biotin is available from Pierce Chemical Co., Rockford, Ill. This embodiment comprises an acceptor SPA beads and quantitation of AA-tRNAs on a scintillation counter (for example a microplate scintillation counter). Microtiter plate assays for amino acid analysis may comprise embedded scintillant or a coating of scintillant.

Figure 13A:
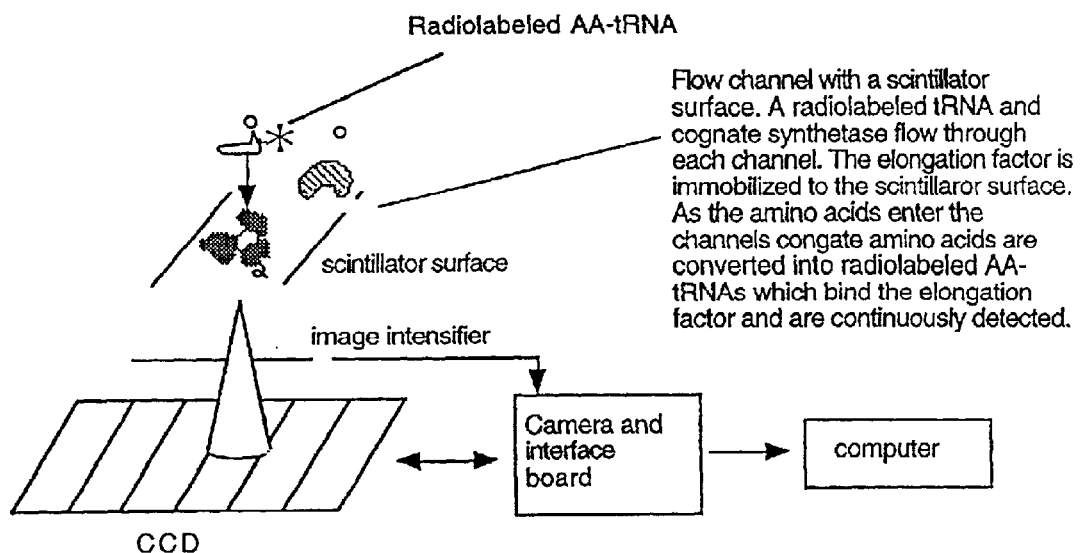
FIGS. 13A–13B illustrate an embodiment of the present amino acid analysis in which the flow channel has a scintillator surface and the label in the system is a radioactive compound.
Figure 13B:
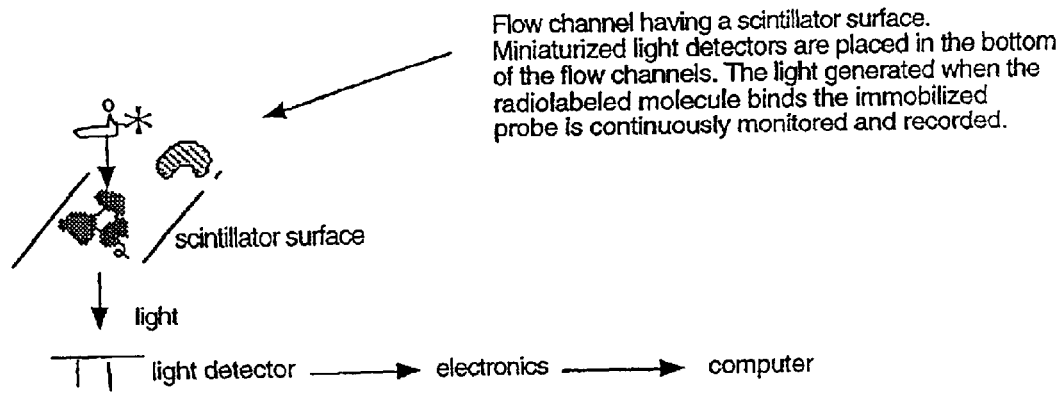

FIGS. 13A and 13B illustrate scintillator surface detection of radiolabeled AA-tRNA-EF-TU:GTP complexes. Embodiments of spatially resolved scintillation proximity assays are illustrated in FIGS. 13A–13B. Each flow channel is surfaced with a scintillator. A particular radiolabeled tRNA and its cognate synthetase flow through each channel. EF-Tu:GTP is immobilized on the scintillator surface within the channel. As the amino acids enter the channel, the amino acid cognate to the tRNA is coupled to the tRNA to produce the corresponding AA-tRNA, which binds the immobilized elongation factor of the channel surface.

There can be continuous detection due to the interaction of the radioactive decay with the scintillator also bound to the channel surface. When a beta particle crosses the scintillator surface, part of its energy is converted to light. The light spot is intensified. The real time signal produced by the light produced is detected after amplification of the light is detected by a CCD camera where it has generated a cluster of charges. The spot of electrons is serially processed, localized, stored and displayed by the electronic system.

The electronic detection system may be composed of a camera, an interface board and a computer. During the data acquisition time the successive binding events are accumulated in real time and displaced on a computer monitor if desired. The summation of the events constitutes the final digital image, which can be stored in a computer-readable form and/or transferred to a processor for generation of amino acid sequence or quantity data.

FIG. 13B shows a microchannel with a scintillator surface. Miniaturized light detectors are placed in the bottom of the flow channels. The light generated when the radiolabeled molecule binds to the immobilized ligand is continuously monitored and recorded, and optionally processed.

In a preferred embodiment, quantitative and/or amino acid sequence information where the amino acid detection is integrated with exopeptidases as described above.

Example 15

Figure 14:
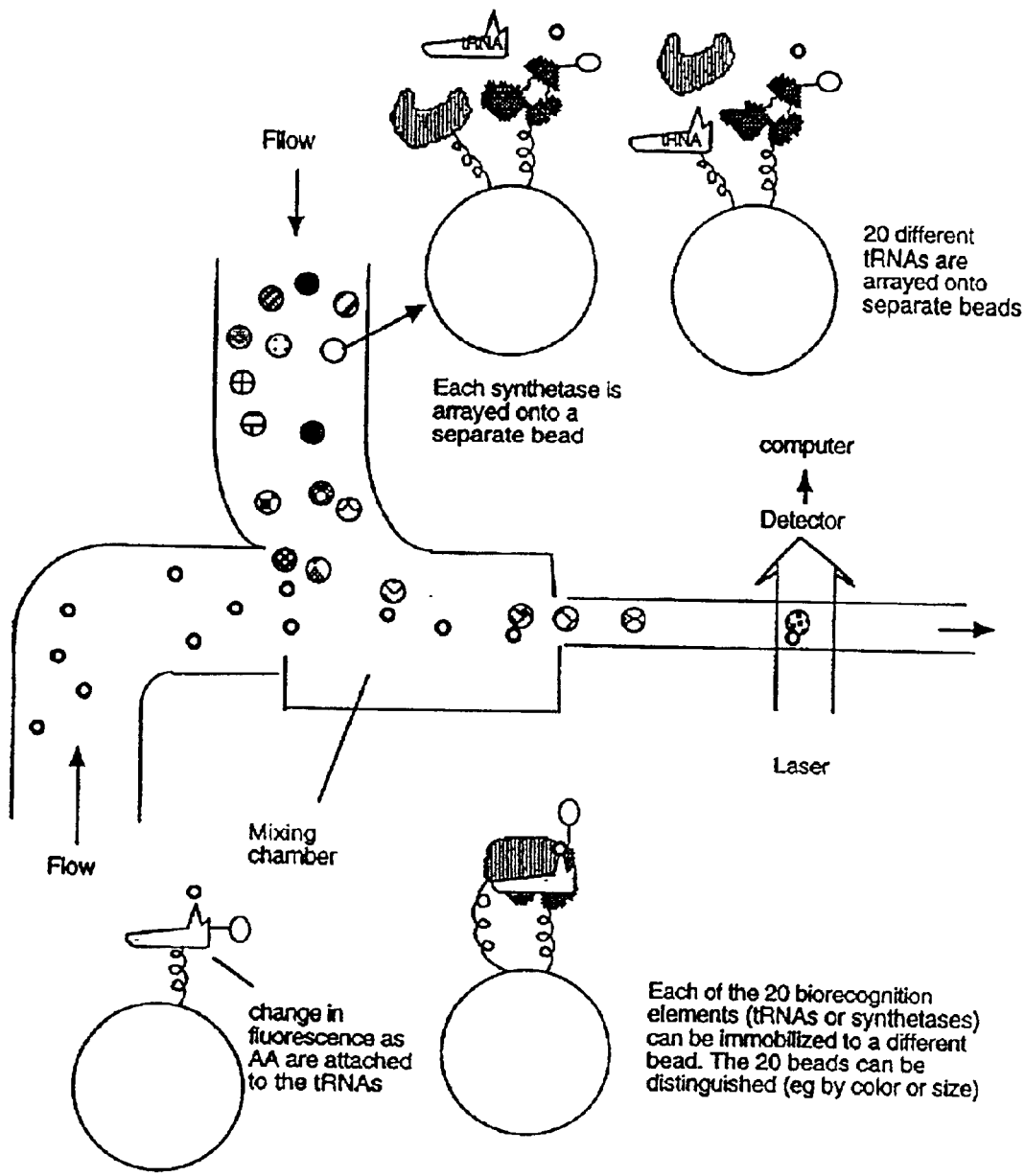
FIG. 14 provides a schematic illustration of an embodiment wherein the assays are carried out on the surfaces of nanoparticles (beads) which are of twenty distinguishable types, each having a distinctive signal generated when the ternary complex of an AA-tRNA and elongation factor are formed.

Example 15 illustrates the use of microbeads in a microarray format of the present invention. See FIG. 14 which shows a amino acid sequence analytical tool in which the twenty labeled tRNAs or the twenty amino acid specific tRNA synthetases are each arrayed onto separate beads or nanoparticles which can be distinguishes as described in Example 30. These beads are introduced into a mixing chamber together with a sample flowstream which contains the amino acids. The components react and bind generally as described above and the reacted components flow past a laser emitting light at the excitation wavelength and a detector. The signal is transferred to a computer for recording and data analysis.

In a preferred embodiment, tRNAs can be labeled with a donor fluor and the elongation factors can be labeled with an acceptor fluor, and a fluorescence energy transfer type of assay can be used to monitor formation of the ternary complex.

Example 16

Figure 15:
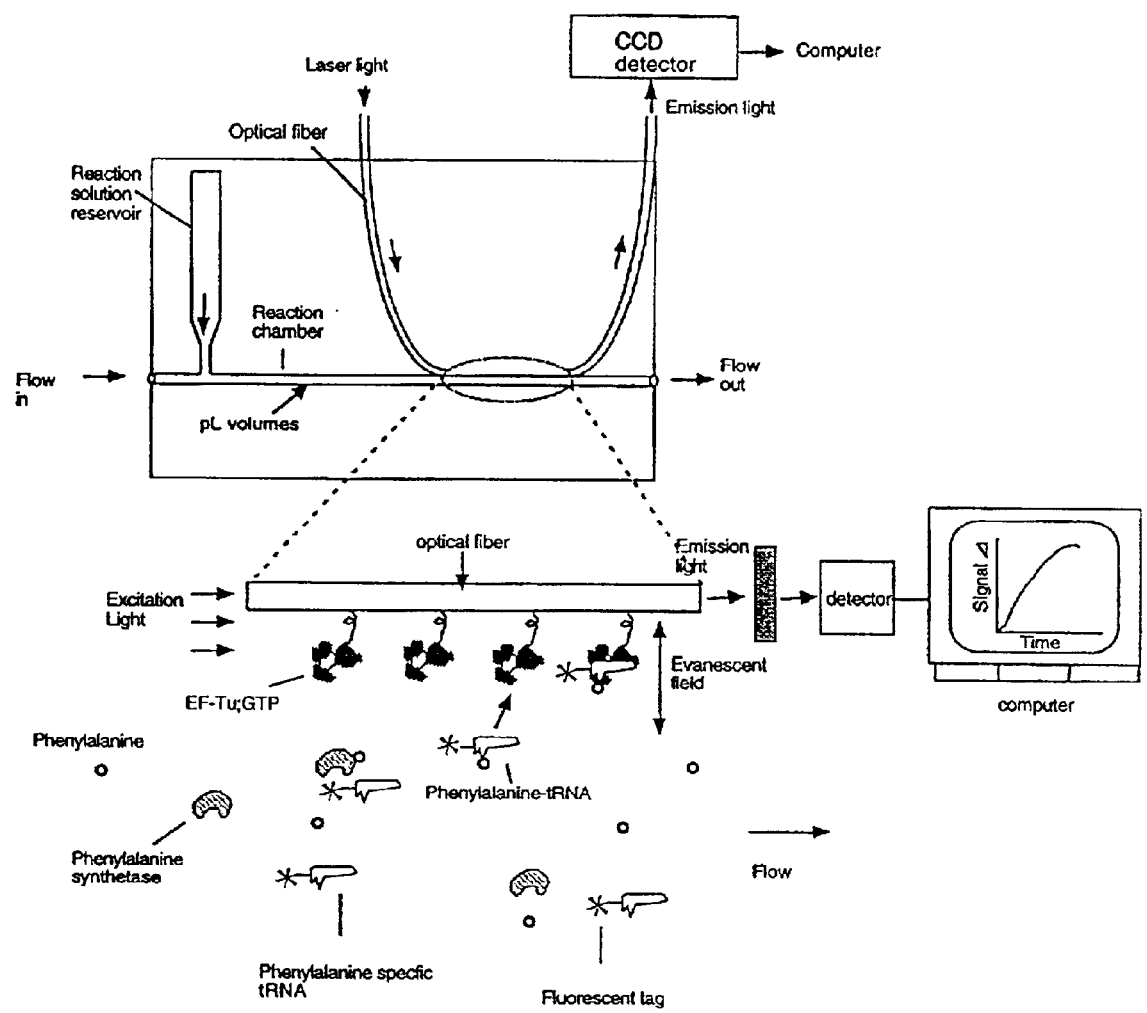
FIG. 15 is a schematic illustration of an amino acid optical fiber biosensor.

Example 16 describes, with reference to FIG. 15, an amino acid analytic device with an optical fiber biosensor. In FIG. 15, only one of the amino acid specific parallel microchannels is illustrated. This amino acid optical fiber biosensor uses immobilized EF-Tu:GTP to bind and detect the fluorescently labeled AA-tRNAs. The elongation factor is immobilized on an optical fiber placed in a microchannel. When complexed with GTP the elongation factor selectively binds all AA-tRNAs with high affinity. The amino acids are converted to the cognate AA-tRNAs by the synthetases in amounts proportional to their concentration in the sample flow, and hence the concentration of an AA-tRNA is directly related to the amino acid concentration in the sample stream. The sample containing the amino acids flows into a reaction microchannel as shown. The reaction channel is joined by a microchannel delivering a continuous flow of reaction solution containing a synthetase and fluoreseently labeled tRNA specific for a particular amino acid. The amino acid in the sample is converted to a proportionate amount of the corresponding AA-tRNA (the system is illustrated for only the amino acid phenylalanine for the sake of simplicity, but an array format accomodating a plurality of amino acids is also contemplated. The plurality of amino acids may be treated and assayed in parallel on an array.) As is well known to one of ordinary skill in the art, optical fibers can be used to both excite and detect fluorescence in the evanescent field so that only the surface-bound fluorescent molecules are detected. This allows the continuous and real time monitoring without a wash step. The elongation factor substantially binds the AA-tRNAs only when also bound to GTP but not GDP. Hence, the bound AA-tRNAs can be eluted using a buffer containing GDP. The immobilized elongation factor can be then reactivated by washing with a regeneration buffer containing GTP and the fiber can then be reused. The binding of the fluorescently labeled AA-tRNAs can be monitored in arrays of microchannels run simultaneously. In this way up to all twenty amino acids can be analyzed simultaneously, continuously and using very small sample volumes (picoliters).

Example 17

Example 17 describes an ultrasensitive solid phase immunoassay for amino acid analysis. A specific ternary complex probe (e.g., an antibody or aptamer that specifically binds the ternary complex, EF-Tu:GTP-AA-tRNA) is coupled to a solid support (e.g., the bottom of a microtiter plate well or a microflow channel). The surface is contacted with a EF-Tu:GTP-AA-tRNA formed by amino acyt tRNA synthetase from the corresponding substrates.

In this system, a first antibody is attached to the surface. This first antibody binds the ternary complex and retains the complex during the wash. Then, a second antibody is used to label the ternary complex to facilitate its detection. This second antibody or detection probe also binds the ternary complex. The detection probe is labeled with a high specific activity label such as a fluor or radioisotope, or it can be labeled with an enzyme that catalyzes an amplification reaction to create an ultrasensitive enzyme-linked ligand assay for amino acid analysis. Examples of labeled probes for detection include antibodies that recognize the captured ternary complex or oligonucleotides or peptide nucleic acid probes that hybridize to the single stranded regions of the captured AA-tRNAs. Enzyme labels where one enzyme produces many labels typically achieve attomole-zeptomole detection limits. Competitive, noncompetitive, displacement, and homogeneous ternary complex immunoassays are particularly useful in the amino acid analytical methods and devices of the present invention.

Figure 16:
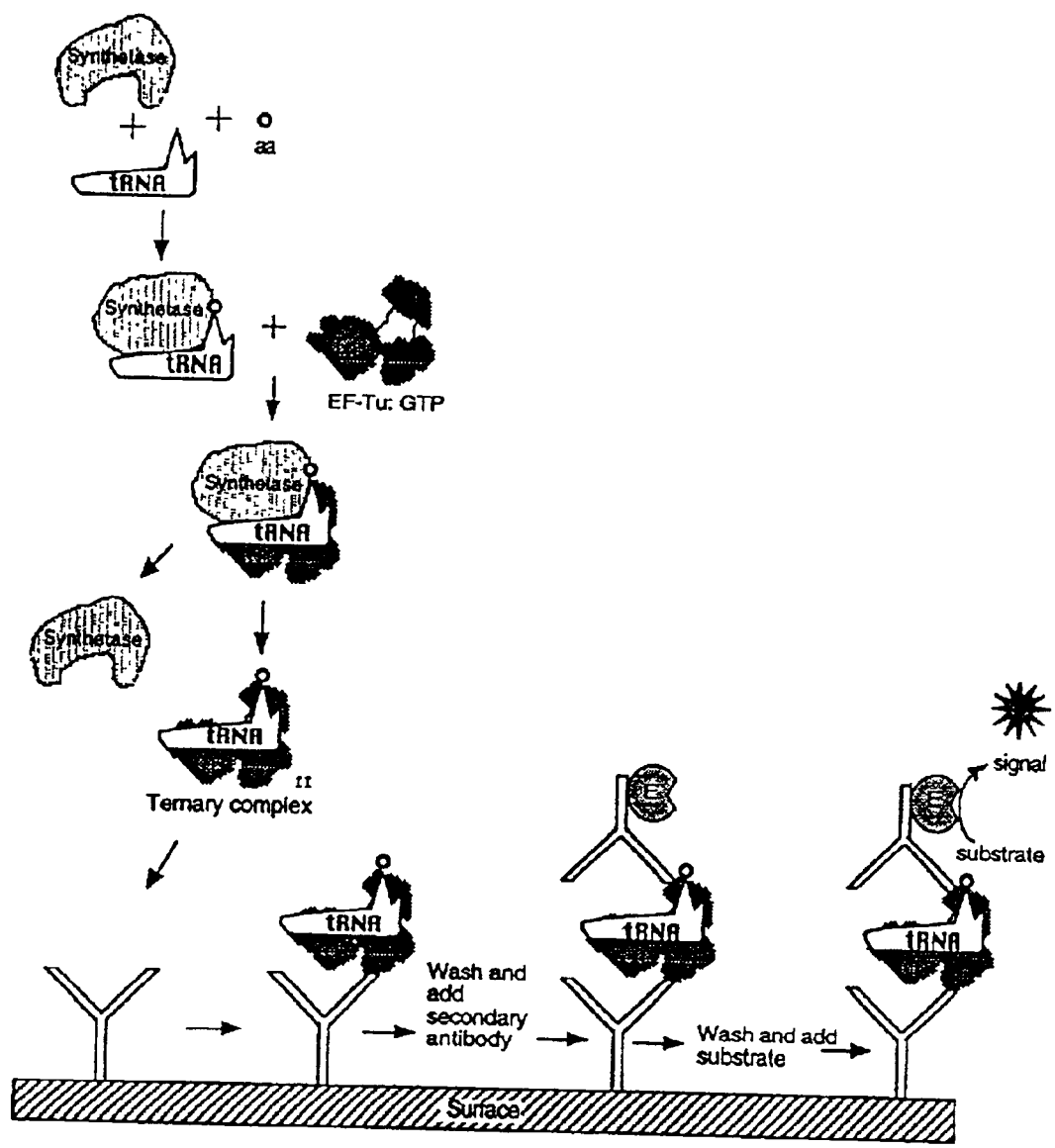
FIG. 16 illustrates an ultrasensitive solid phase immunoassay method for amino acid analysis.

FIG. 16 illustrates the method in an ELISA format. The figure illustrates only one of the up to twenty amino acid specific parallel microchannels or microwells. In this system, a first antibody is attached to the surface. This first antibody binds the ternary complex and retains the complex during the wash. Then, a second antibody is used to label the ternary complex to facilitate its detection. This second antibody also binds the ternary complex. The secondary antibody bears an enzyme label. Thereupon, the enzyme activity of the bound label is measured according to its activity which provides a measure of the amount of ternary complex formed, and hence the amount of the corresponding amino acid in the sample. In this system, a first antibody is attached to the surface. This first antibody binds the ternary complex and retains the complex during the wash. Then, a second antibody is used to label the ternary complex to facilitate its detection. This second antibody also binds the ternary complex. The secondary antibody bears a label. Thereupon, the bound label is detected according to its activity which provides a measure of the amount of ternary complex formed, and hence the amount of the corresponding amino acid in the sample.

In a preferred embodiment, a microflow channel contains amino acids released by the sequential proteolytic digestion of the protein of interest and the channel is at that point perfused with cognate synthetase and tRNA and the complex detectedas described above.

Example 18

Figure 17:
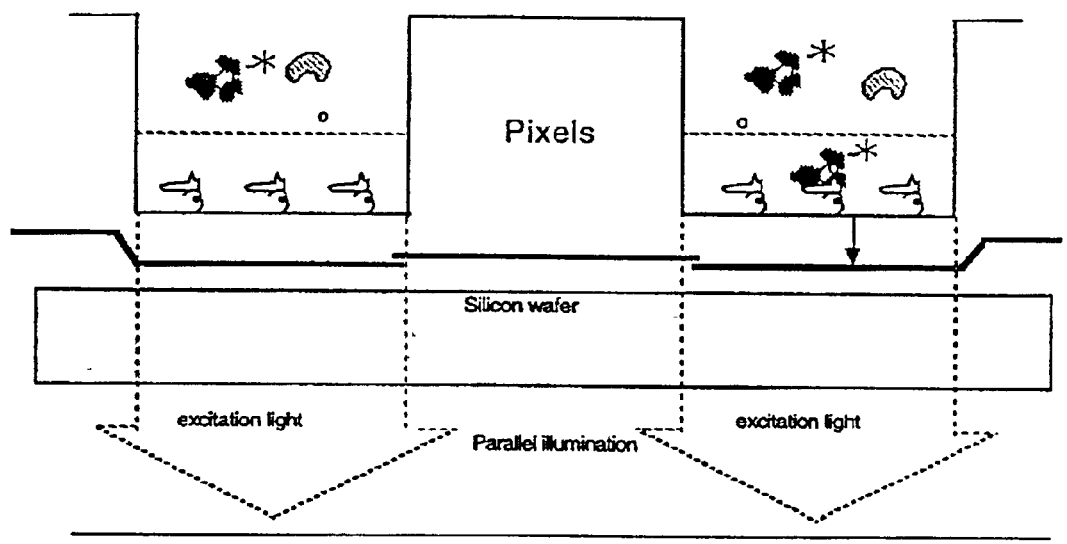
FIG. 17 illustrates a microsystem for amino acid analysis with direct spatially resolved CCD detection of the formation of the ternary complex on a microchip detector.
Figure 17:
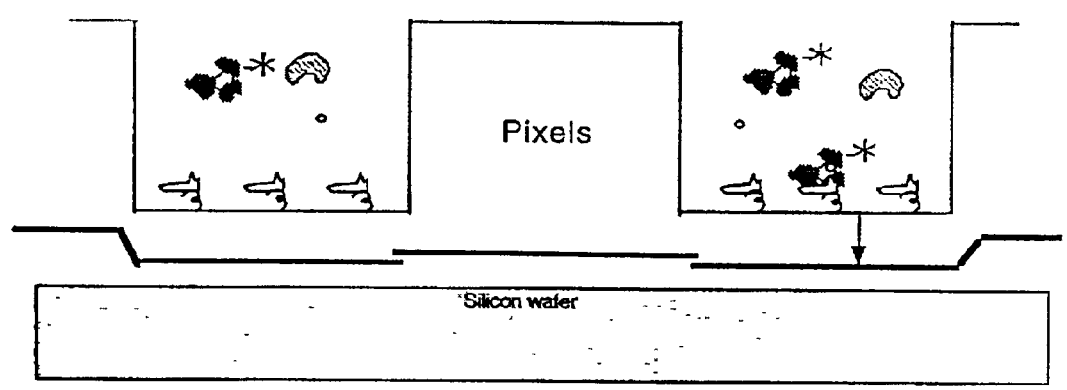

Example 18 describes, as shown in FIG. 17, the use of a CCD Detector as Solid Support in Amino Acid Sequence Analysis. FIG. 17 illustrates direct CCD molecule detection on a microchip. Biomolecular probes including, without limitation, elongation factors, synthetases or tRNAs, are immobilized directly onto the pixels of a CCD or they can be attached to a cover slip placed on the CCD surface. As shown, twenty different tRNAs, each with a different amino acid-specificity, are immobilized and the elongation factor is captured by binding to the AA-tRNA. Alternatively, the elongation factor can be immobilized and the tRNA labeled. Each amino acid is attached to its cognate tRNA by its cognate synthetase. The newly formed AA-tRNA binds to the immobilized elongation factor and is detected. The binding molecule (e.g., the elongation factor) can be labeled with a radioisotope, a chemiluminescent molecule or a fluorescent tag. After binding of the labeled molecule to the CCD array, photons or radioisotope decay products are emitted at the pixel locations where the labeled molecule has bound. Electron-hole pairs are generated in the silicon where the charged particles or radiation from the labeled molecule are incident on the CCD gates. Electrons are collected beneath adjacent CCD gates and are sequentially read out on a display module. The number of photoelectrons generated at each pixel is directly proportional to the number of labeled molecules bound and hence the amino acid cognate to the synthetases and tRNAs in each channel or well. Other proximity assays such as scintillation proximity assays are also within the scope of the present invention.

Example 19

Figure 18:
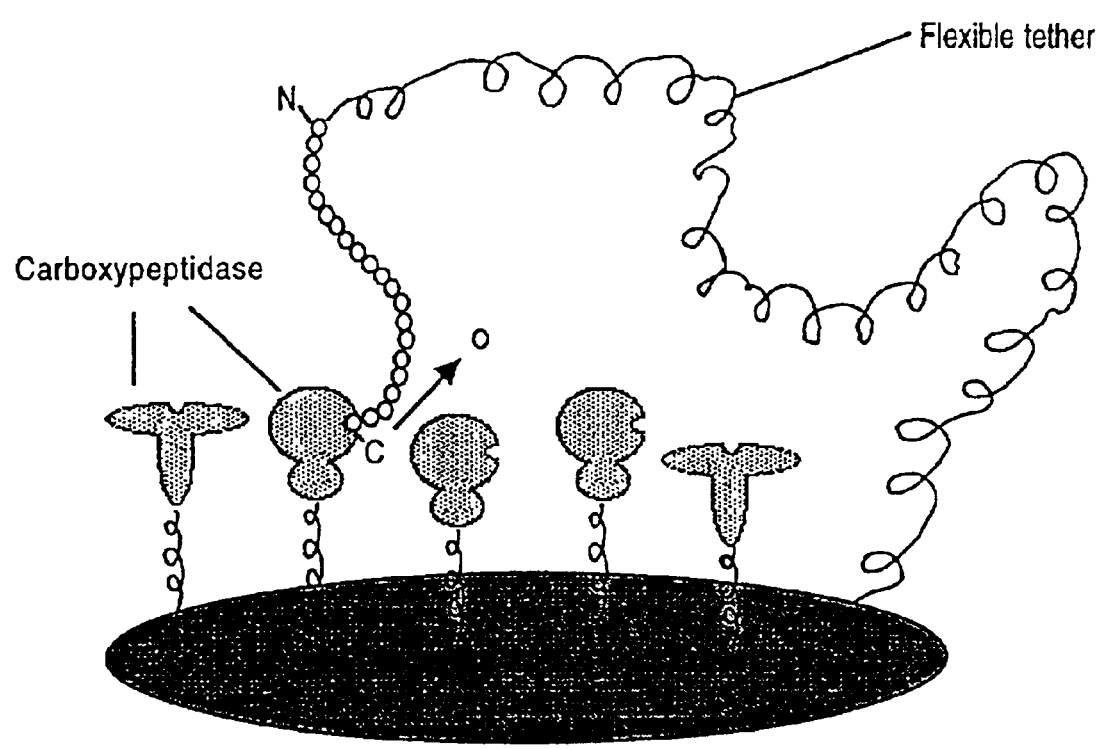
FIG. 18 illustrates a situation wherein the polypeptide or peptide to be synthesized and the carboxypeptidases are co-immobilized on the same surface via flexible tethers.

Example 19 describes a nanoparticle digestion chamber for use in one embodiment of the invention. The polypeptide targeted for sequence analysis and the carboxypeptidase enzyme can both be tethered (i.e., immobilized) on the same surface in the digestion chamber, which can be particularly tiny. See FIG. 18. Nanoparticles, especially magnetic nanoparticles, can be used in a chamber in which there is an especially high concentration of enzyme and substrate. The volume can be as small as 1 microliter or less. The nanoparticles are immobilized, and an effluent stream of liberated amino acids flows into the detector arrays. The carboxypeptidases such as carboxypeptidase P or carboxypeptidase Y can be tethered to a surface by its C-terminus. The protein target of sequencing can be immobilized using a long and flexible tether so that it has a free carboxy terminus, is confined to the surface but it has freedom to move about by diffusion and collide with the immobilized enzyme. Even though the absolute amount of target protein may be low, the concentration on the surface is high. In this way, the immobilized substrate does not have to diffuse very far before it collides with enzyme; thus the net reaction rate will be increased as compared with reaction rate for enzyme and substrate both in solution. In addition, the immobilized carboxypeptidase cannot serve as a substrate, which could complicate data analysis if amino acids were released from the immobilized carboxypeptidase as well as from the protein for which sequence data is sought.

The proteins and peptides are conjugated to the surface of vesicles using known methods. For example, they may be tethered covalently to the phosphatidylethanolamine in liposomes using amino reactive coupling. Phospholipid vesicles permit diffusion within the plane of the bilayer and will therefore permit frequent collisions of the co-immobilized elements. This ensures suitable reaction rates. These particles can be dispensed into wells containing the arrayed biorecognition elements for amino acid analysis described above or they can flow into microchannels for aminoacylation reactions, ternary complex formation and signal detection and decoding. This type of assay permits end group amino acid sequence analysis using the high-density amino acid analysis microarrays described above. Alternatively, they can be immobilized in flow streams with the effluent stream of liberated amino acids flowing through amino acid detection microfluidic arrays. Carboxypeptidases can be immobilized via the C-terminus, or the C-terminus can be blocked (for example, by conjugation of the C-terminus with biotin) to prevent autolysis.

Example 20

Figure 19A:
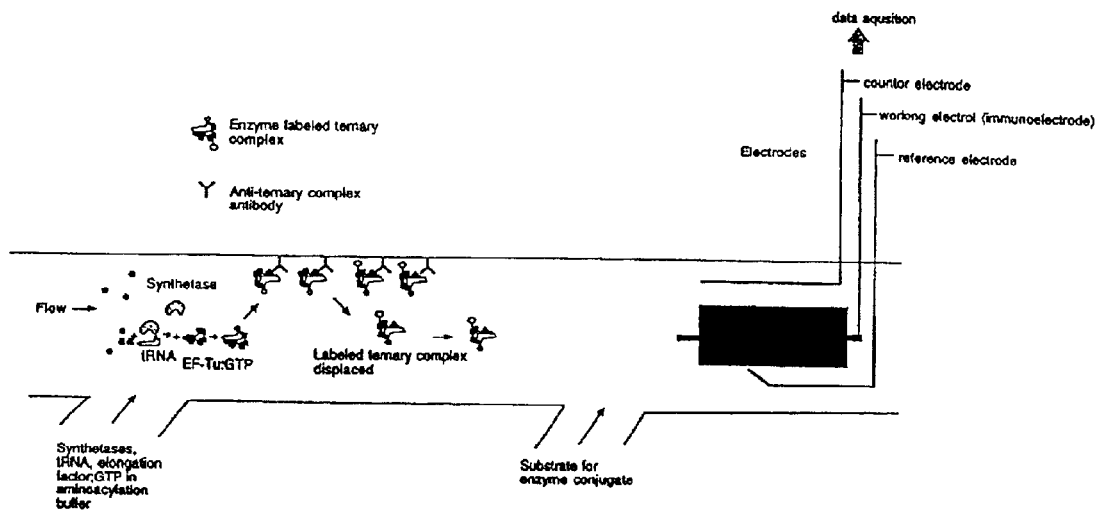
FIGS. 19A and 19B are schematic drawings of a microsystem amino acid analyzer using electrochemical detection. A continuous flow displacement format is shown.
Figure 19B:
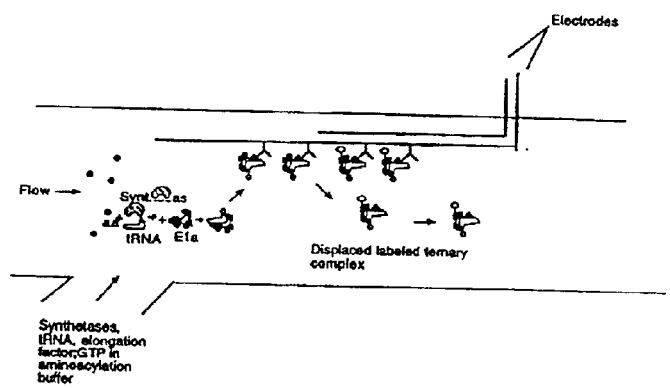

Example 20 illustrates the use of an electrochemical detector. FIGS. 19A and 19B are schematic drawings of a microsystem amino acid analyzer using electrochemical detection. A continuous flow displacement format is shown. In FIG. 19A the ternary complex is labeled with an enzyme label and reversibly bound inside a microchannel using an antibody that specifically binds the ternary complex. The reaction channel has an inlet for amino acids, an outlet, and is in fluid connection with two reservoirs. A reaction mixture containing a specific synthetase, cognate tRNA and EF-Tu:GTP is continuously pumped through the reaction channel from one reservoir. As amino acids flow into the reaction channel, those having a cognate synthetase and tRNA in the channel are converted into AA-tRNAs which bind the EF-Tu:GTP to form a ternary complex. The newly formed ternary complex displaces a proportionate amount of enzyme-labeled immobilized ternary complex that then flows downstream. The substrate for the enzyme label in a suitable buffer is pumped through the reaction channel downstream of the immobilized labeled ternary complexes. As the displaced enzyme labeled ternary complexes flow through the zones having its substrate, the enzyme generates its electrochemically detectable substrate, which is detected at the microelectrode placed in the flow channel. Microelectrode arrays are constructed for the continuous detection of all 20 primary amino acids simultaneously by using 20 reaction channels, each perfused with a different synthetase and cognate tRNA and having a microelectrode.

FIG. 19B shows an amino acid analyzer microbiosensor that uses continuous flow displacement with electrochemical detection. An antibody that specifically and reversibly binds the ternary complex is immobilized on the working electrode. The antibody is saturated with ternary complex labeled with an enzyme that catalyzes a reaction that produces a product that can be detected electrochemically. A reaction mixture containing substrate for the enzyme along with a specific synthetase, cognate tRNA and the elongation factor is pumped through the reaction channel from a reservoir using microfluidic pumping. Amino acids enter the channel, and those having a cognate synthetase and tRNA are converted into ternary complexes that displace a proportionate amount of the labeled ternary complex from the microelectrode. This results in a proportionate decrease in signal at the microelectrode. The decrease in signal at the microelectrode is proportionate to the concentration of the amino acid having a cognate synthetase and tRNA in the channel. As above, using the microelectrode arrays and methods of the present invention facilitates the analysis of all 20 primary protein amino acids simultaneously.

Nonenzyme electrochemical labels can also be conjugated to the tRNAs or elongation factors and used for electrochemical detection. For example, ferrocene is a electrochemical label that may be conjugated to the elongation factor or tRNAs. Takenaka et al. (1994) *Anal. Biochem.* 218:436–443 describe a method for the conjugation of ferrocene to DNA and an electrochemical detection system that allows femtomole detection of labeled DNA probes binding to complementary sequence.

Example 21

Example 21 further describes methods for the co-immobilization of carboxypeptidases with their substrate proteins to facilitate rapid digestion of tiny amounts of protein in tiny chambers. The method will also reduce the losses of protein samples by adsorption onto surfaces. Proteins need to collide in order to react and therefore it is not typical or obvious to immobilize two proteins that are to interact. However, by using long polar and flexible spacer arms or immobilizing the proteins onto a surface that permits collisions of immobilized proteins, not only will the two proteins interact, but the rate of reaction will be greatly increased due to increasing the local concentrations on the surface and thereby increasing the rate of collisions. If the coimmobilized proteins are tethered to liposomes via flexible tethers, they will be confined to a surface but will undergo frequent collisions due to the diffusion of the lipids to which they are attached within the two-dimensional plain of the lipid bilayer. This will decrease diffusion limitations by converting a three-dimensional random walk into a two-dimensional random walk and greatly decrease the number of collisions that reacting proteins make with the solvent before colliding with substrates.

The proteins may be coimmobilized to lipids in liposomes via crosslinking reagents or by other methods as reviewed in Keinanen K et a. (1994) *FEBS Lett* 346, 123–6. Methods for the conjugation of proteins to liposomes are well known in the arts. The carboxypeptides (e.g., carboxypeptidase Y) may be expressed with C-terminal extensions that are both flexible and polar that will be used as tethers.

By using an amino acid composition that is rich in glycine the tethers will be flexible since glycine has no side chain and only a hydrogen atom instead, it adds flexibility. Serine is a polar and uncharted amino acid, hence, it can be encoded into the tether. The C-terminal residue of the carboxypeptidase-tether may be a cysteine. This will permit thiol specific conjugation to surfaces or protein substrates of carboxypeptidases.

The particles bearing the co-immobilized protein substrate and exopeptidase may be placed in the microarrays for amino acid analysis for high throughput end group analysis. For example these particles may be placed into the microwell arrays shown in FIG. 8D.

Example 22

Figure 20:
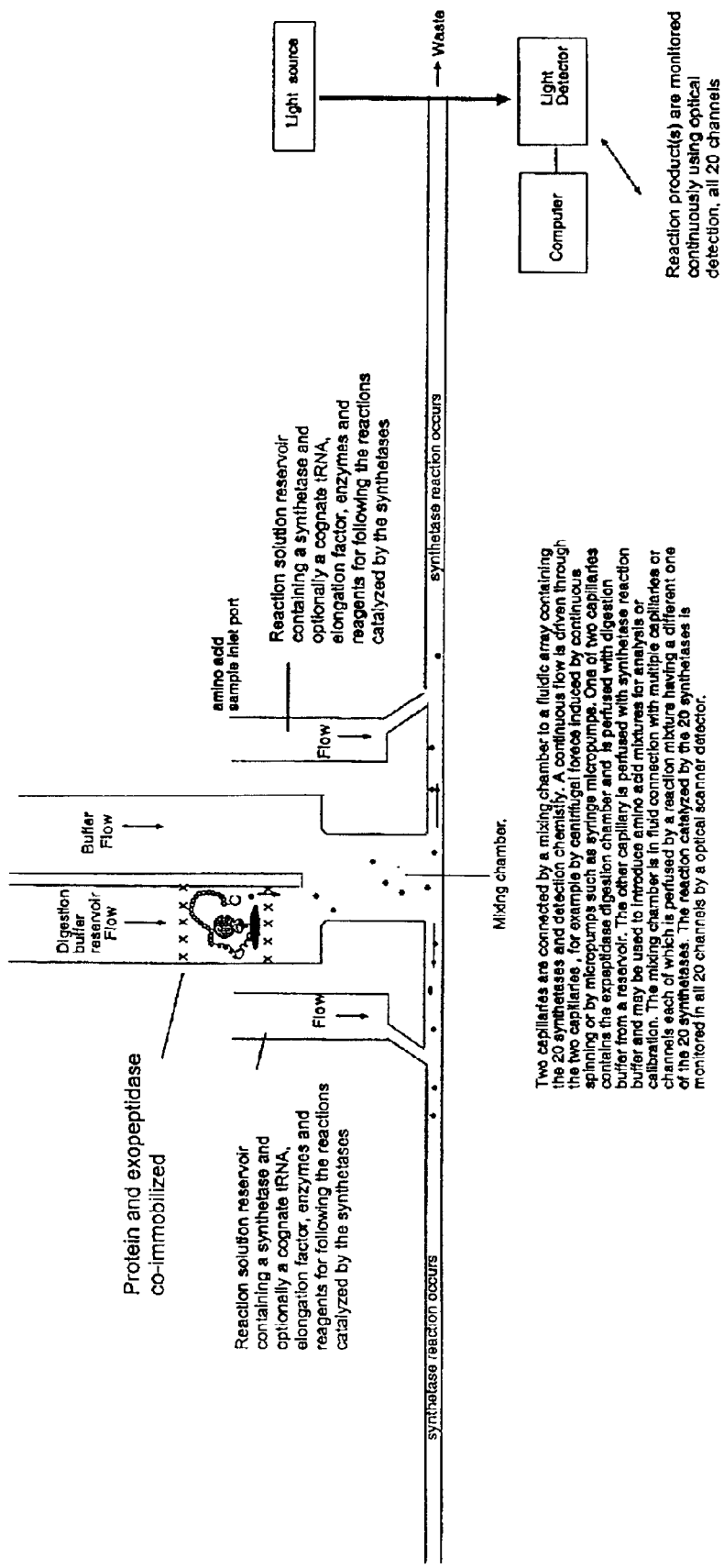
FIG. 20 is a schematic drawing of a continuous flow enzymatic amino acid analyzer and end group sequenator using optical detection.

Example 22 describes a continuous flow enzymatic amino acid analyzer according to the invention. FIG. 20 provides a schematic drawing of an embodiment according to this example. FIG. 20 shows a continuous flow enzymatic amino acid analyzer and end group sequenator using optical detection. The synthetase reactions are arrayed into 20 amino acid specific reaction channels or capillaries in fluid connection to a central circular chamber. Each of the amino acid specific reaction channels is in fluid connection to a separate reservoir containing a unique synthetase and optionally a cognate tRNA and EF-TU:GTP in reaction buffer. The exopeptidase digestion chamber is placed in a flow stream that connect with the circular chamber having the multiple inlets to the reaction channels. Inlets lead to the specific amino acid reaction channels having a different one of the synthetases and additional inlets will be employed for control channels or capillaries or for the analysis of multiple samples or duplicate assays.

The digestion chamber may be a sealed hollow fiber or may be encapsulated in a dialysis membrane having a molecular weight cutoff that allows free amino acids to pass freely and is impermeable to macromolecules. Alternatively, the protein substrates may be coimmobilized with the exopeptidases on a surface (for instance, as described above) and held in the flow stream by a porous support, magnetic force, immobilized ligand or in some other way. As the amino acids are liberated from the protein's termini by the exopeptidases, they flow through the digestion chamber and past a continuous flow mixer. The amino acids flow through the amino acid specific reaction channels. The amino acids having a cognate synthetase in each channel will react to form proportionate amount of product. In a preferred embodiment the flows are driven by centrifugal force and the system spins. A light source and computer linked detector are integrated into the system. The product of the synthetase reactions will be continuously monitored by the detector. The detector may be a scanning spectrophotometer, luminometer or fluorometer depending upon the assay used to follow the synthetase reactions. The amino acids will be identified from the location of the chamber in the array giving the signal as the synthetase reaction(s) are monitored in all chambers.

If enzyme labels or other detection reagents are employed in the assay the enzyme substrates, buffers, and reagents will be pumped or otherwise flowed through the reaction and control channels from a reservoir(s). Any continuous optical detection method may be used to follow the synthetase reaction(s) in a spatially distinguishable manner including chemiluminescent and bioluminescent assays by following the formation of the reaction products (e.g., PPi, AMP, AA-tRNAs, synthetase-AA-AMP).

In a preferred embodiment, the sequential proteolytic digestion of the target protein takes place within a sealed hollow fiber having a molecular weight cutoff such that amino acids pass freely but macromolecules do not. As amino acids are released by the exopeptidase, they diffuse through the pores of the fiber and enter the flowstream (FIG. 20A) and are carried to the microfluidic reaction and detection arrays. As shown, a laser beam or other light source excites the fluor bound to the AA-tRNA in the ternary complex, and the emitted light is detected by a detector, for example, a CCD detector. In this embodiment, the twenty microchannels can be in a circular array (carousel) and as the carousel rotates, the scanning detection systems detects whether there is labeled ternary complex in one or more microchannels. Fluid transport is optionally achieved by cetrifugal pumping as the microflow system spins. The optical detector and the light source may be stationary.

Example 23

Figure 21:
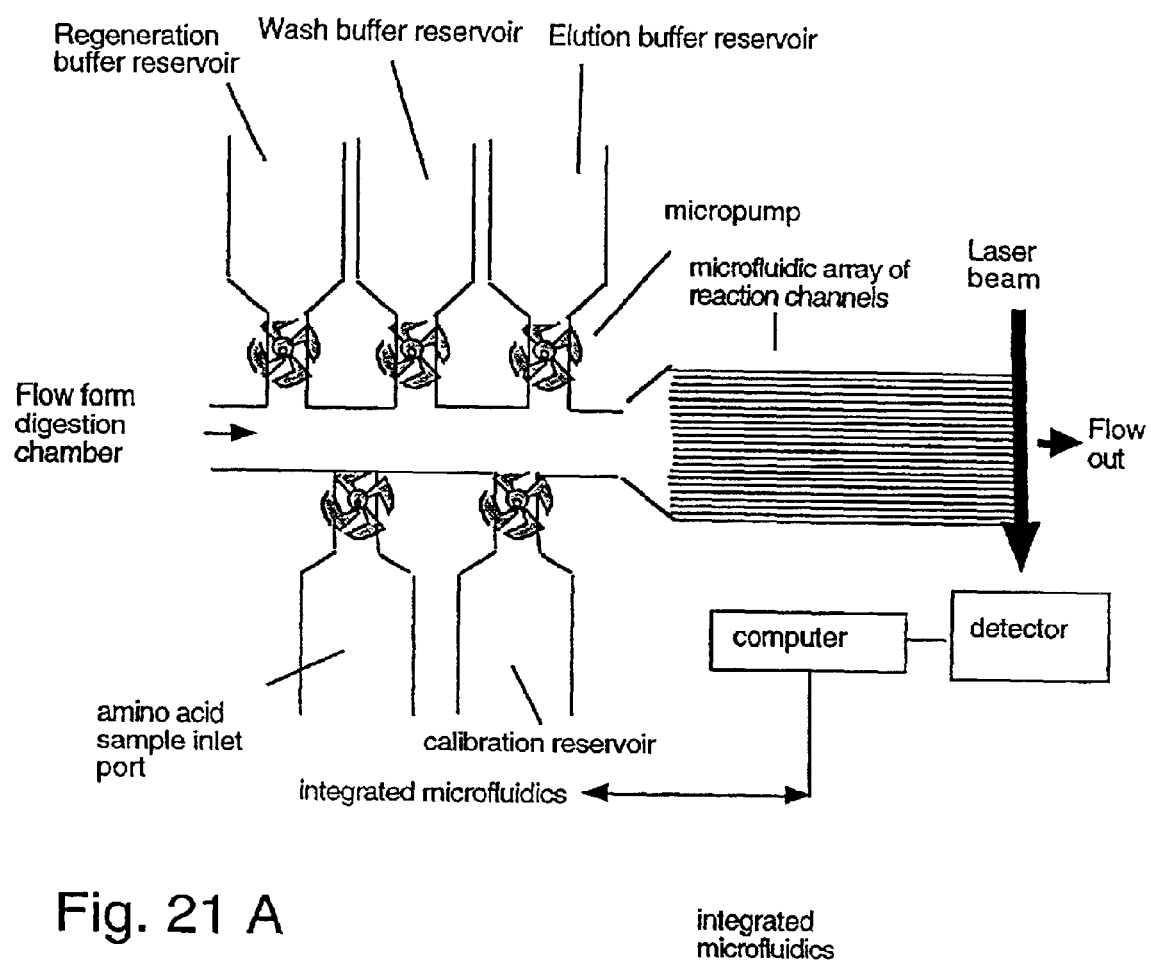
FIGS. 21A–21B illustrate a computer-controlled integrated microsystem for amino acid analysis and protein end group sequencing using affinity capture and detection of labeled AA-tRNAs on immobilized EF-Tu:GPT with automated calibration, washing, detection, elution, and regeneration of the capture site.
Figure 21:
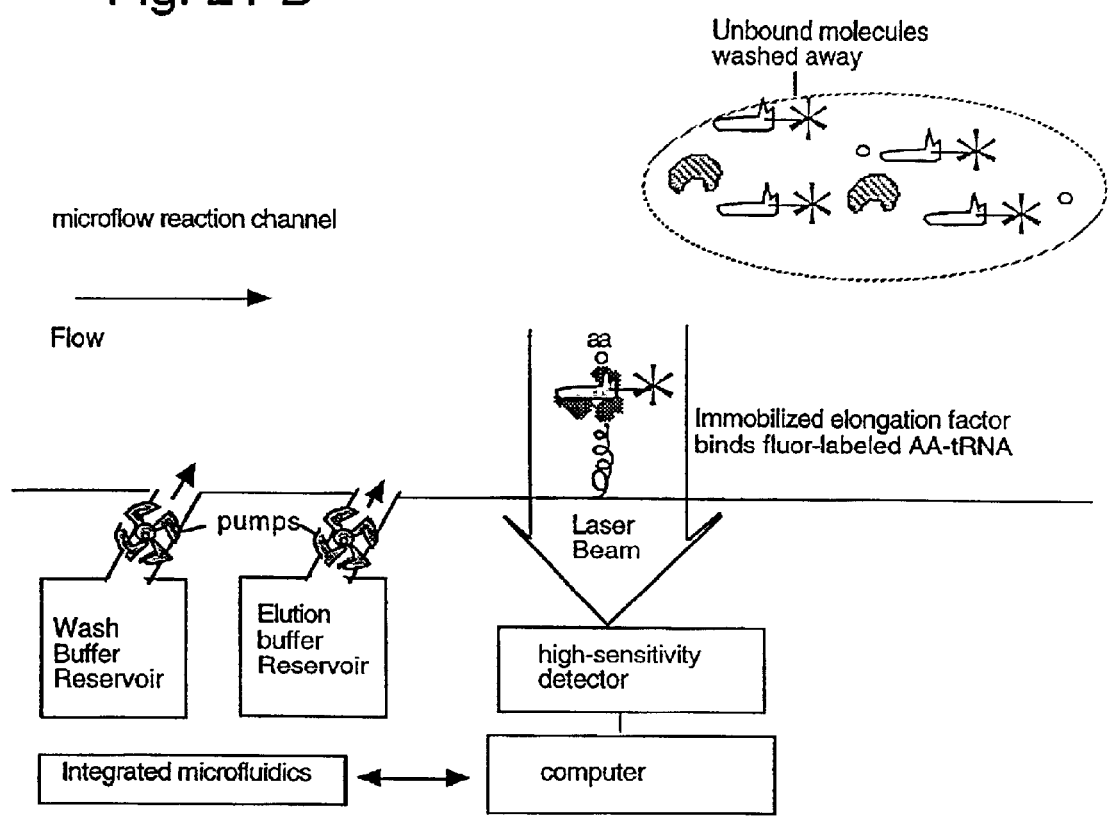

Example 23, as depicted in FIGS. 21A–21B illustrates a computer-controlled integrated microsystem for the analysis of one or more amino acids in a sample. In the particular embodiment of FIG. 21A, the sample comes from a digestion chamber providing protein amino acid analysis and/or protein end group sequencing. The system preferably uses affinity capture and detection of labeled AA-tRNAs on immobilized EF-Tu:GTP with automated calibration, washing, detection, elution, and regeneration of the capture site.

The elongation factor can be immobilized in the microflow channel as described above and depicted in FIG. 21B. Briefly, the elongation factor is expressed as a fusion protein having a C-terminal flexible tether (optimally composed of glycine residues to ensure flexibility and neutral polar amino acid residues such as serine) having an attachment site (e.g., a C-terminal cystine for thiol specific coupling to surfaces or a hexa-His tag or other ligand specific tag). The elongation factors are optionally immobilized onto transducers such as optical fibers or microelectrodes that are positioned in the microflow channel.

The automated system allows automated calibration with known concentrations of amino acids pumped through the microfluidic array from calibration reservoirs by microfuidic pumping, prewashing to remove unbound or weakly bound material, detection, elution of the labeled aminoacyl tRNAs with an elution buffer, and regeneration of the capture sites with a regeneration buffer all under computer control.

Preferably, all fluidic handling (volumes and flow rate of respective solutions) and data acquisition or image acquisition (series of fluorescent images) are synchronized by means of a computer. The wash buffer reservoir, calibration reservoirs, elution buffer reservoirs, and regeneration buffer reservoirs are in fluid connection with the microfluidic array such that solutions from these reservoirs are pumped through the microfluidic reaction channel arrays as shown in cases where a labeled probe (for example fluorescently labeled oligonucleotides or peptide oligonucleotides that bind to the captured AA-tRNAs) are used for detection, additional reservoirs are added to automatically deliver the probes.

An amino acid sample inlet port is also depicted. The amino acid specific reaction solution reservoirs join the corresponding reaction channel in the array as described above (e.g., FIG. 5A) are not shown. The digestion chamber (not shown) is as described above, and amino acids flow continuously from the digestion chamber through the main channel. A computer controlled valve optionally diverts the flow of the amino acid mixture pumped from the digestion chamber into a waste reservoir during the automated steps of washing, detection, elution, and capture site regeneration. An additional reaction channel(s) can be added to serve as a control. In this case the reaction solution reservoir is the source of reaction solution buffer through the control channel without a synthetase, therefore, no AA-tRNAs are formed in the control channel.

An exemplary experimental procedure for amino acid analysis using this instrument where the elongation factor is immobilized onto optical fibers would be as follows:

1. Equilibrate the reaction channels with reaction buffer and determine a base line by applying excitation input light and detecting the emitted light.

2. Amino acid mixtures of known concentrations will be pumped through the reaction channels from calibration reservoirs and the signals will be determined as outlined below to establish a calibration curve.

3. Add amino acid sample to the sample inlet port or allow the sample to be pumped through the reaction channels from an exopeptidase digestion chamber such as described in FIG. 5A and above. As amino acids enter each reaction channel they react with cognate synthetases and tRNAs forming AA-RNAs that are captured by the immobilized elongation factors.

4. In the case where the amino acid samples flow from the digestion changer, a computer controlled micropump will stop the flow. Then the computer controlled micropump will pump wash buffer through the reaction channels.

5. If a fluorescently labeled AA-tRNA probe is employed, the probe will be pumped through the channels automatically following the automated washing step using computer controlled micropumps.

6. Wash buffer will again be pumped through the channels.

7. Where fluorescently labeled tRNAs are employed, steps 4 and 5 will be omitted.

8. The input light will be applied at the excitation wavelength and the emitted light intensity will be measured by the detector. The fluorescence intensity will be correlated with the concentration of amino acid in the sample. Applying excitation input light at an appropriate wavelength, fluorophore generate photons of another wavelength and the emitted light intensity will be correlated with the amino acid concentration in the sample.

9. The elution buffer will be pumped through the reaction channels.

10. Regeneration buffer will be pumped through the channels to reactivate the sensor surface for another round for sampling.

11. A base line will be measured as in Step 1 and the next sample will be taken.

12. Where the amino acids flow from the digestion chamber, a computer controlled pump or valve will now start the flow of amino acids from the digestion chamber through the microchannel array for additional readings. The steps will be automatically repeated to detect the amino acids liberated by the exopeptidases continuously as a function of time. And the record of the amino acids detected will be used to computer a sequence.

13. The above steps may include an elution step after each reading of the captured fluorescent molecules. This step will be followed by reading the base line fluorescence and regenerating the binding site by pumping regeneration buffer through the reaction channels.

14. Suitable wash, elution, and regeneration buffers may be those described in Robeiro, et al. (1995) *Anal Biochem,*

228,330–335 for the affinity purification of AA-tRNAs on immobilized elongation factor Tu from *Thermus thermophilus* EF-Tu; GTP.

Example 24

Example 24 describes some of the preferred embodiment of spatially resolved homogenous binding assays as exemplified in end terminal protein sequencing. However, any sample of the 20 protein primay amino acids or a subset thereof can be analyzed. Microflow channel or microwell formats can preferably be used.

In terminal protein sequencing embodiments, the protein of interest is sequentially degraded, either from the amino terminus or the carboxy terminus. Alternatively, the protein can be totally digested, and one simultaneous measurement of all twenty primary amino acids can be made. Where the total digestion of the protein is carried out for the analysis of the amino acid composition of the protein, the proteases utilized can include those including but not limited to, one or more of the following: trypsin, chymotrypsin, staphylococcal V8 protease, aminopeptidase and a carboxypeptidase. Preferably, for a total digestion, there are a combination of proteases used. Where the carboxy terminus is the target, carboxypeptidase is used. The degradation can be carried out in a digestion chamber which is separated from the flow channel by a molecular sieve (e.g., a selectively permeable membrane, microdialysis membrane or microdialysis probe, through which free amino acids but not polypeptides of greater than about 6000 dalton molecular weight can pass in an unhindered fashion. The exopeptidase can be immobilized in the digestion (or reaction) chamber, either to a surface within the chamber or on a solid support such as a microbead within the chamber.

The free amino acids diffuse into a flowstream that enters a microfluidic array of reaction channels/capillaries. Through each reaction channel is pumped a reaction buffer having a different tRNA and its cognate synthetase along with EF Tu:GTP. When AA-tRNAs are formed and bound by the EF-Tu:GTP, the fluorescence changes. The fluor can be bound to the tRNA or to the EF-Tu:GTP provided that the specificity and the ability to bind ligands are not changed.

A fluor can preferably be bound to the tRNA or to the EF-Tu:GTP, provided that the specificity and the ability to bind ligands are not changed. Both tRNAs and EF-Tu:GTP have been fluorescently labeled and found to retain their binding specificities.

Reactive groups such as thiol, amine, or phosphorothioate can be introduced in nucleic acids for coupling of chromophores. For example, see Johnson et al. (1982) *J. Mol. Biol.* 156:113–140. Labeling of tRNAs can be achieved by hybridizing a fluorescently labeled oligonucleotide or peptide nucleic acid to the single stranded regions of the tRNAs. Alternatively, fluors can be covalently conjugated to the tRNAs (Janiak et al. (1990) *Biochemistry* 29; 4268–4277) labeled tRNAs by attaching fluorescein covalently to the thiouridine (s4U) at position 8 which is a conserved residue (U or s4U) in all tRNAs. The labeled tRNAs retained their abilities to be aminoacylated by the synthetases and recognized by the elongation factors. Upon binding of EF-Tu:GTP with the fluorescent AA-tRNA, the emission intensities increased. The emission intensity was nearly the same for all AA-tRNAs when bound to EF-Tu:GTP. The method of Janiak et al. can be used to label the t-RNA with fluorescein. Synthetic or enzymatic procedures have been established, allowing site-specific incorporation of thionucleotide(s) such as 4-thiouracil within RNA, and structural and biological activities remain intact (reviewed in Favre et al. (1998) *J. Photochem. Photobiol. B*42: 109–124).

Alternatively, the elongation factors may preferably be labeled with fluors. Many references can be found on modification of various groups in proteins or peptides with fluors. These are summarized in reviews or monographs; for example, see Haugland, R. P. (1992) *Handbook of Fluorescent Probes and Research Chemicals*, 5th ed., Molecular Probes, Eugene, Oreg. Although several groups can be used to couple to a chromophore, the thiol group is thought to be the best candidate in that many groups are thiol specific or selective, and thus unique labeling is possible. With site-directed mutagenesis a thiol group can be added to or deleted from a desired position. Since the three dimensional structure of the ternary complex of aminoacylated tRNA and EF-Tu-GTP has been solved (reviewed in Nissen et al. (1996) *Biochimie* 78:921–933), the contact sites between the elongation factor and AA-tRNAs are known. From the structure many amino acid residues on the protein's surface are available that do not interact with AA-tRNAs and are hence good candidates for labeling. The elongation factor can be conveniently labeled using a fluorescent GTP analog. Elongation factor Tu has been labeled with fluorescent GTP analogs, and it has been found to retain its specificity for AA-tRNAs. For example, the ribose of GTP was covalently modified with the dye rhodamine (Rh) to form GTP-Rh, and the GTP-Rh was used to label EF-Tu. The EF-Tu:GTP-Rh retained its specificity for AA-tRNA (Watson et al. (1995) *Biochemistry* 34:7904–12). GTP has been labeled with other fluors and used to label EF-Tu (Giovane et al. (1995) *Eur. J. Biochem.* 227:428–432; Eccleston et al. (1987) *Biochemistry* 26:3902–3907). EF-Tu complexed with fluorescent GTP analogues retains its specificity for AA-tRNAs.

Another way to fluorescently tag the elongation factor is to fuse it with the green fluorescent protein (Iwane et al. (1997) *FEBS Letts.* 407:235).

Since rhodamines absorb where fluorescein emits, they can be used as energy acceptors in fluorescence energy transfer assays. Watson (1995) et al. have shown that AA-tRNAs labeled with fluorescein specifically bind to EF-Tu:GTP labeled with rhodamine. They used fluorescence energy transfer to determine the macromolecular arrangement in the aminoacyl-tRNA-EF-Tu complex.

For the analysis of free amino acids in a sample, the sample liquid is placed in the reaction chamber, so that the amino acids pass through the molecular sieve and into the microchannels or microwells or into contact with the microspots for quantitation. In this embodiment, there is one measurement made for each amino acid, rather than a series of measurements for each amino acid over time.

In the microwell format, the sequential proteolysis is carried out as above. The released amino acids are dispensed in parallel into microwells each specific for a particular amino acid and containing the reagents necessary for the amino acid react with the cognate synthetase to form AA-tRNAs, which are bound by the EF-Tu:GTP. In one embodiment, the tRNA contains a bound fluor, for example as taught in Janiak et al. (1990) *Biochemistry* 29:4268–4277. The wells contain immobilized EF-Tu:GTP which will bind the AA-tRNA. The wells are emptied and desirably washed prior to excitation of the fluor and detection of the signal. In this embodiment, the twenty wells are repeated multiple times, and there is a sequential dispensing of exopeptidase digest into each set. A micropipettor can dispense the amino acid-containing dialysate from the digestion chamber. Detection of those wells in which there is AA-tRNA EF-Tu:GTP complex successively over time allows the determination of the terminal amino acid sequence of the protein. Where the exopeptidase is an amino peptidase, the N-terminal sequence of the protein is deduced; and where the exopeptidase is a carboxypeptidase, the C-terminal sequence of the protein is deduced. See FIG. 20 for a diagrammatic illustration of a microplate that can be used in this embodiment of the invention. The wells can alternatively comprise labeled tRNAs which can be immobilized to the bottoms of the microwells by binding to immobilized EF-Tu:GTP or a labeled oligonucleotide capable of binding to each particular AA-tRNA can be used to generate a signal in the presence of each particular AA-tRNA, in which case a washing step precedes signal determination. Samples can be taken every 5 min as described using reaction conditions with carboxypeptidase Y(For an example, see Patterson, D. M. (1995) *Anal. Chem.* 67:3971–3978).

Although the release of amino acids by the exopeptidase is nonlinear, by taking frequent time points one can generate rate curve information and the terminal sequence can be deduced.

To detect the presence of a particular amino acid covalently bound to its cognate tRNA, the well or microchannel is illuminated with light at the excitation wavelength and fluorescence is detected according to the wavelength of the emitted light. A laser of the desired wavelength of light can be used for the excitation.

In another embodiment, the free amino acids which leave the digestion chamber across the selectively permeable microdialysis membrane can be channeled to amino acid-specific channels, each of which are specific for a particular amino acid due to the presence of a particular aminoacyl tRNA synthetase and tRNA. The AA-tRNA can then be detected on an array containing the detectors with positional information related to a particular amino acid-specific ity of each channel and its particular synthetase and tRNA. Information from the detectors is transmitted to a computer where it is decoded to provide amino acid sequence information. The change in aminoacyl tRNA formed with time is directly related to the sequential endwise degradation of the protein of interest in the digestion chamber. See FIGS. 21A–21B for a diagrammatic representation of such a microfluidic system for endgroup analysis (in this diagram, C-terminal amino acid sequence analysis) and sequence. As the amino acids are liberated from the protein substrate in the digestion chamber and cross a microdialysis membrane, they enter a flowstream that carries them into the amino acid detector microfluidic array. The amino acid mixture, which over time is sequentially enriched for a particular amino acid according to its position within the protein of interest, flows into a central chamber and then the flowstream is split between the reaction channels, each specific for a particular amino acid. Each reaction channel is in fluid connection with a unique reservoir containing a particular tRNA and synthetase. The amino acids react with their cognate tRNAs and synthetases, and they are detected in a spatially resolved manner. An optical fiber can be coupled to the detector portion of the channel or channel accepting reacted material from the reaction channels, with the result that signals generated in response to laser excitation are fed to a computer which then translates the data into amino acid sequence information. Desirably, the channels are in fluid communication with waste receptacle(s) so that continuous flow can be accomplished as the protein of interest is sequentially degraded.

Alternatively, the microdialysis probe is attached to microchannels or microcapillaries that are perfused with a solution containing the twenty aminoacyl tRNA synthetases, EF-Tu:GTP and a tRNA species specific for one amino acid. As the amino acids diffuse across the microdialysis membrane and enter the detection chamber, they are converted to a proportionate amount of the ternary complex with EF-Tu:GTP, which complex displaces a corresponding amount of labeled ternary complex within the detection chamber. The labeled complex then flows to the detector and is quantitated. From the record of the passage of labeled molecules past the detector in the twenty channels each specific for a particular amino acid, the sequence of the protein of interest is deduced.

A further specific embodiment of the microwell format is one in which within each microwell or nanowell, there is a central spot in which the protein of interest is present together with an immobilized exopeptidase, for example, a carboxypeptidase. The amino acids freed by carboxypeptidase digestion of the protein of interest, diffuse to the twenty individual spots within the well, each of which is specific for a particular amino acid. Within the cognate spot, the amino acid is converted to the AA-tRNA by the action of the particular amino acid tRNA synthetase present. Hundreds to thousands of wells on a single plate or microchip allow the simultaneous analysis of many minute samples. In this embodiment, the synthetase and elongation factor are immobilized to a unique microspot. If evanescent excitation and/or detection are used, real time amino acid analysis is possible. As shown the tRNAs are fluorescently labeled, and the formation of the ternary complex is monitored by the change in fluorescence as the ternary complex forms. The amino acids are being released continuously so that the concentration in solution is highest for amino acids closest to the terminus where digestion occurs and they are detected first.

A tRNA specific for each amino acid to be analyzed is uniquely labeled. For example, each tRNA is tagged with a unique fluorescent dye. The labels may be attached directly to tRNAs. Alternatively, the dyes may be attached to surfaces e.g., proteins, nucleic acids, or nanoparticle and these surfaces may be attached to the tRNA. EF-Tu:GTP is immobilized to the bottom of chambers (e.g., microwells, or microflow channels). An amino acid sample along with the aminoacyl-tRNA synthetases and the uniquely labeled tRNAs are introduced into the chambers. The amino acids in the sample are attached to their cognate tRNAs, each bearing a unique label. The AA-tRNA-label complexes are then captured by the immobilized elongation factor:GTP and are detected. The unique labels on the tRNAs specific for each amino acid will allow the amino acid identity for each captured AA-tRNA-label to be identified. A wash step may be included to remove unbound substances. The captured AA-tRNA-labels may be read using a confocal fluorescent microscope fitted with a CCD camera, for example.

Example 25

Example 25 describes a computer-controlled integrated microfluidic system for amino acid analysis and end group sequencing. Twenty reservoir arrays, each specific for one of the naturally occurring amino acids, are each in fluid connection with a unique reaction channel. The laser and detector are connected to the reaction channels. The laser can be guided to the reaction channel array using optical fibers or waveguides., Alternatively, the detectors can be built in. Proximal CCD or other proximal detection systems such as a scintillation proximity system can also be utilized.

Figure 22:
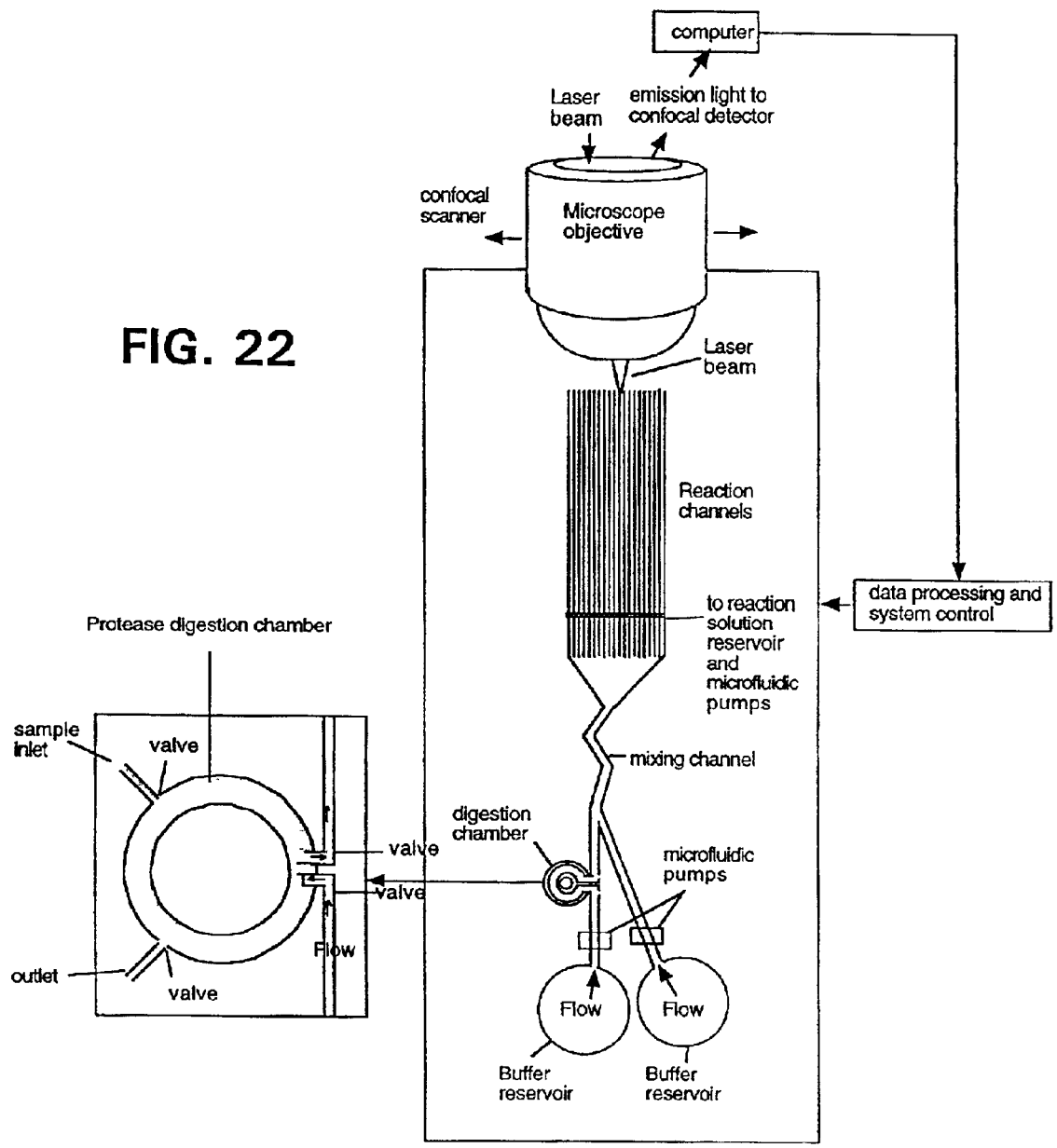
FIG. 22 is a schematic diagram of a microsystem for amino acid analysis with integrated on-chip enzymatic hydrolysis.

FIG. 22 is a schematic diagram of one such microsystem for amino acid analysis with integrated on chip enzymatic hydrolysis. Enzymatic hydrolysis of the protein or peptide sample occurs on-chip in a separate peptidase digestion chamber. The digestion chamber is in fluid connection with the amino acid analysis microfluidic arrays. A mixture of endopeptidases and exopeptidases are employed to achieve total hydrolysis. The proteases are immobilized on beads and placed into the digestion chamber or optionally are immobilized on the bottom of the chamber. In cases where polypeptides and peptides are analyzed, it is sufficient to use a mixture of carboxypeptides and aminopeptides to achieve total hydrolysis. In cases where larger proteins are analyzed, other proteases are immobilized in the digestion chambers along with the carboxypeptidases and aminopeptidases. Commercially available proteases that may be used in this system to achieve total enzymatic hydrolysis include but are not limited to, carboxypeptidase Y, carboxypeptidase P, carboxypepdidase A, aminopeptidase M, aminopeptidase L, trypsin, subtilisin, proteinase k, pepsin, papain, endoproteinase Glu-C, (proteinase V8), endoproteinase Asp-N, endoproteinase, Arg-C, elastase, collagenase, chymotrypsin, cathepsin C, acylamino acid peptidase.

The peptidase digestion occurs in the microfabricated digestion chamber that is in fluid connection with the amino acid detection microfuidic array as described above. The digestion is sealed from the flow stream connecting it to the microfuidic amino acid detection array using valves that are opened and closed by a computer. A circular digestion chamber is shown which may have circular pumping of the digestion buffer thereby providing convection within the channel to facilitate rapid and complete digestion. After the digestion has been completed, which can be determined by having an optical detector integrated into the digestion chamber, the amino acid mixture is pumped from the digestion chamber through the amino acid analysis microfluidic array using microfluidic pumping. The amino acids are analyzed on the chip as described above (e.g., in FIG. 5A).

Example 26

Figure 23:
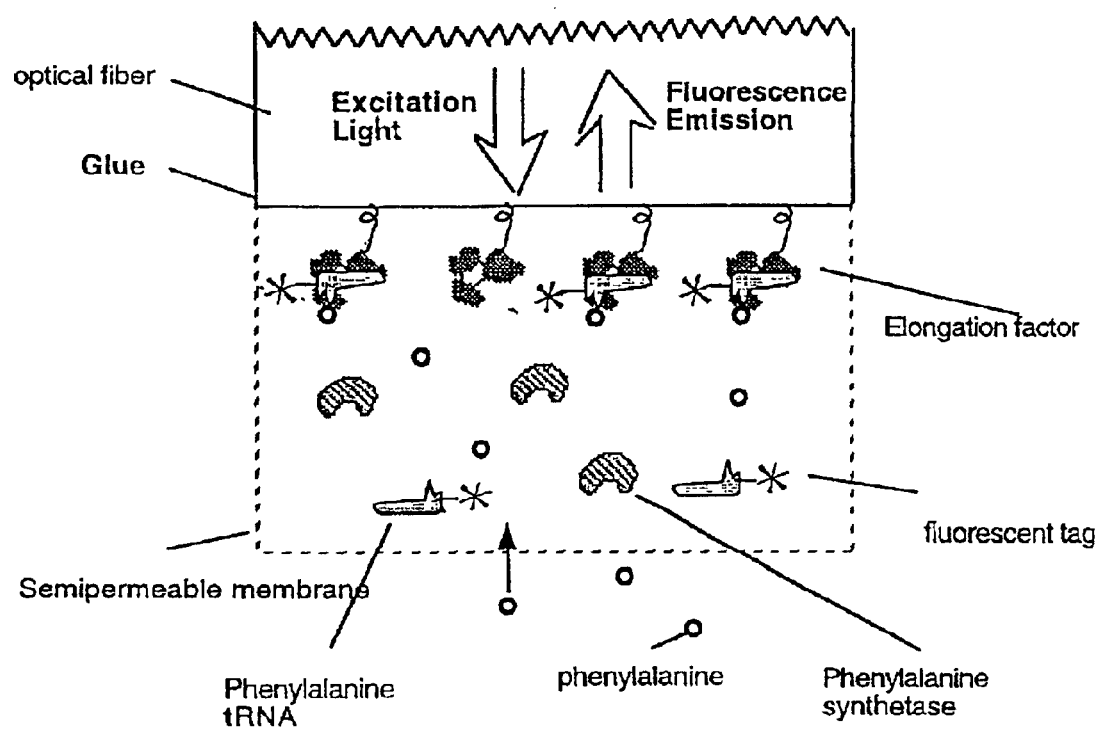
FIG. 23 is a schematic illustration of a single amino acid affinity biosensor. The specific example is detection of phenylalanine in a sample.

Example 26 describes an amino acid affinity biosensor according to the invention. FIG. 23 depicts a specific example of detecting the amino acid phenylalanine in a sample, biosensors to other amino acids are within the scope of the invention, either used alone or in combination. For example, this simple affinity biosensor format can be used for any of the 20 primary protein amino acids by substituting the corresponding cognate synthetase and tRNA in place of the phenylalanine specific synthetases and tRNAs.

In FIG. 23, the elongation factor is immobilized on an optical fiber probe, and a synthetase and fluorescently labeled tRNA cognate for the amino acid being analyzed by the sensor is held next to the sensor by semipermeable membrane. Amino acids cross the semipermeable membrane into the biosensor containing phenylalanine aminoacyl-tRNA synthetase and fluorescently labeled phenylalanine tRNA. The synthetase attaches the phenylalanine to its cognate tRNA. The newly formed AA-tRNA specifically binds the immobilized elongation factor and is captured on the surface and detected. The membrane has a molecular weight cutoff such that amino acids can freely cross the membrane but macromolecules (tRNAs and synthetases) cannot.

Example 27

Example 27 describes label displacement assays according to the invention. In preferred embodiments, microarray systems can be provided and a labeled ternary complex is reversibly immobilized inside a flow channel or microwell.

In a preferred embodiment, an electrochemical detection method for detecting the amino acids is used. The ternary complex label can be an electrogenic label such as an enzyme as in FIG. 24A. The substrate for the enzyme is introduced into the flow channel via a microchannel in fluid connection with the channel. The substrate is converted to product by the enzyme conjugate and the product is detected by a microelectrode positioned within the channel or well. In another format the labeled ternary complex is reversibly immobilized on the microelectrode surface.

For example, the enzyme horseradish peroxidase can be used with an electrogenic substrate to generate a detectable signal. When carried out in very small volumes, ultrasensitive electrochemical assays are achieved. The action of the enzyme upon the substrate generates a product detectable by the elecrode. As the amino acid sample enters the chamber, each amino acid is converted into a proportionate amount of the ternary complex (AA-tRNA-EF-Tu:GTP) which then displaces a proportionate amount of the reversibly bound labeled ternary complex. The displacment results in a proportionate decrease in signal at the microelectrode.

Alternatively the label can be an enzyme that catalyzes a chemiluminescent reaction. In this case also, the substrate is introduced into the flow channel via a microchannel in fluid connection with the channel. Optionally, the substrate for the enzyme conjugate can be immobilized within the well or on the inside surface of the flow channel. In this case, the displacement results in a proportionate change in the fluorescence signal generated as monitored by the optical detection device.

In another embodiment, as shown in FIG. 24B, the reversibly bound ternary complex which is to be displaced by an elongation factor is labeled with a flourescence label. In this case, the displacement of the labeled complex by the EFTu:GTP:aminoacyl tRNA complex reduces the flourescence signal in an amount related to the amount of amino acid in the sample. In these embodiments, the labeled ternary complexes are preferably irreversibly bound to an optical fiberor optical waveguide.

In another embodiment as shown in FIG. 24C, the displacement reaction alters the refractive index at the surface of the plasmon resonance detector when the reversiby bound macromolecule is displaced by an agent providing a different effect on the refractive index at the plasmon surface.

Example 28

Example 28 describes some preferred fluorescence energy transfer binding assays for amino acid analysis. The amino acids are detected by following the formation of the ternary complex using fluorescent resonance energy transfer assays. Since rhodamines absorb where fluorescein emits, these fluorescent labels are examples of labels that can be employed for FRET assays of the subject invention. However, other donor/acceptor pairs can be used. For example, the elongation factors may be labeled with rhodamines and the tRNAs labeled with fluorescein.(For example see Watson et al. (1995) *Biochemistry* 34:7904–7912.) Rhodamine-labeled GTP may be prepared as described in Cremo et al. (1990) *Biochemistry* 29:3309–3319 and may be complexed to the elongation factor as described above. Alternatively the rhodamine may be site specifically conjugated to another site in the elongation factor. And the tRNAs are labeled with fluorescein. For example, 5-(iodoacetamido) fluorescin (Molecular Probes, Eugene, Oreg.), may be conjugated a thiouridine (e.g., the thiouridine at position 8 in the tRNAs). For fluorescein, the excitation and emission wavelengths are 490 nm and 520 nm respectively.

Example 29

Example 29 describes various methods known to the art for arraying both proteins and nucleic acids are used in the arraying of the synthetases and tRNAs on microchips. For example, attachment of cDNA targets to a glass chip can be carried out using non-covalent charge interactions. In such a method, glass slides are coated with poly-L-lysine onto which cDNA clones or other nucleic acid molecules are printed (De Risi et al. (1997) *Science* 278:680–686). This method of attachment relies on the electrostatic interactions between the positively charged lysine residues and the negatively charged phosphate backbone of the nucleic acids and hence should also be suitable to pattern the 20 specific tRNAs on a chip. Several methods of constructing protein microarrays have also been developed and are known to those skilled in the art. For example, Behringer Mannheim (Indianapolis, Ind.) developed a method that deposits arrays of 100–200 spots (~80 um in diameter) on the flat bottom of wells (Ekins, R. P. (1998) *Clin. Chem.* 44:2015–2030).

In addition to the requirement of high sensitivity, the enzymatic amino acid analyzers of the present invention provide spatially resolved detection. Highly resolved optical detection of fluorescent labels enables the quantitation of captured ligands on arrays of many thousands of bioaffinity molecules simultaneously. Spatially resolved fluorescence detection in miniaturized systems can be achieved by direct imaging through a microscope, through optical fibers, or through optical waveguides. Fluorescent signals pass through spatial and spectral filters to the detection system. Ultrasensitive, spatially resolved detection on high-density arrays may be achieved with confocal laser scanners or imaging CCD cameras, which are known in the art. A schematic illustration of a preferred amino acid analyzer microarray detection system of the present invention is shown in FIG. 3. Upon excitation by a laser, a CCD camera detects the pattern of fluorescent molecules on the surface, and image analysis software correlates the position of the fluorescent signal with the identity of the amino acids. Formation of the ternary complex on the surface can be measured quantitatively using a modified epifluorescence microscope equipped with a CCD camera. Real-time ultra-sensitive measurements can be made, for example, by using evanescent wave excitation and an intensified video CCD camera. Many tiny spatially resolved wells or microflow channels can house the patterned array of recognition elements. Thousands of these chambers can be constructed on a single chip or plate. Fluorescent array detectors can quantitate end-labeled nucleotides at subattomole levels. Label-free probes can be detected using surface plasmon resonance (Thiel et al. (1997) *Anal. Chem.* 69:4948–4956), although array density and sensitivity do not match those of the fluorescence systems.

Example 30

Example 30 further describes the use of bead arrays for amino acid analysis. In one embodiment, fluorescent beads with unique fluorescent profiles can be used to label different tRNAs or aminoacyl-tRNA synthetases and used to create a fluorescence-based array capable of simultaneously assaying multiple amino acids in a sample.

A tRNA Bead Array

For example, a tRNA attached to a unique label (e.g., bead) is reacted with its cognate synthetase and amino acid forming AA-tRNA-bead. The labeled AA-tRNA is then bound to EF-Tu:GTP that is labeled with a distinguishable label (for example a fluorescent dye). A tRNA specific for each amino acid to be analyzed is immobilized on a unique bead type. Then the beads are mixed together and reacted with the amino acid sample and synthetases. AA-tRNAs form on the beads. Labeled EF-Tu:GTP is added to the array. The EF-Tu:GTP then binds the AA-tRNAs on the beads. The samples may be read in a flow cytometer which allows each microsphere to be identified and the corresponding binding signal, from the fluorescently labeled EF-Tu:GTP that has bound the AA-tRNA-microsphere, to be read.

A tRNA specific for each amino acid to be analyzed in the bead array is immobilized to a unique bead set. Uniquely distinguishable beads are commercially available (For example, polystyrene microspheres with various surface chemistries suitable for protein and nucleic acid immobilization may be purchased from Luminex, Corporation, Austin, Tex. or from Bangs Laboratories, Inc., Carmel, Ind.). Numerous methods exist for coupling macromolecules to surface groups on beads as taught, for example, in Lundbald, 1991, *Chemical Reagents for Protein Modification* $2^{nd}$ ed, CRC Press, Boca Raton, Fla. For example, heterobifunctional crosslinking reagents may be used for covalent coupling. A water-soluble carbodiimide which reacts with a carboxylic acid group on the bead and an amine group in the protein or nucleic acid may be employed. Another method uses an NHS-maleimide which reacts with an amine on the bead surface and a free sulfhydryl group on the molecule to be attached. These covalent coupling groups can also be used to attach intermediate reagents such as avidin for the attachment of biotinylated molecules, or an antibody which captures the analyte to be measured. A probe that specifically binds AA-tRNAs such as EF-Tu:GTP is labeled with a fluorescent dye. For example, EF-Tu:GTP may be labeled with a green fluorescent dye when the beads are distinguished by red and orange fluorescence By mixing the different sets of beads bearing the unique tRNAs, the assay will measure multiple amino acids in a sample in a single vessel (e.g., microwell or microchannel). The bead-tRNAs are then reacted with the aminoacyl-tRNA synthetases and amino acid sample in reaction buffer along with or followed by the fluorescent EF-Tu:GTP probe. The synthetases attach cognate amino acids in the sample to their specific tRNAs, each on a unique bead set, forming AA-tRNA-beads. The green fluorescent labeled EF-Tu:GTP binds the AA-tRNAs formed on each bead. After a short incubation period, the mixture of beads which now have various amounts of green fluorescence on their surface due to the binding of EF-Tu:GTP-green dye to the AA-tRNAs, are analyzed in a flow cytometer. Data acquisition, analysis, and reporting may be performed, for example, as described in Fulton et al, 1997 supra when using the bead sets available from Luminex. Using this approach, each bead is classified into its unique set on the basis of orange and red fluorescence and the green fluorescence value, corresponding to the amount of amino acid in the sample cognate to the tRNA on each bead type, is recorded.

Alternatively, the beads may be read in an optical fiber array detection system as taught in Michael et al. (1998) supra and U.S. Pat. No. 6,023,540 or in other schemes employing imaging detectors (for example, see Brenner et al. (2000) *Nature Biotechnology* 18: 630–634.

In additional, methods of the current invention aminoacyl-tRNA synthetases are attached to unique labels as mentioned above and the interaction of each labeled synthetase with its cognate amino acid is detected. This may be achieved, for example, by immobilizing each synthetase to a different microsphere having a distinguishable label as above and reacting the labeled synthetase with its cognate amino acid and fluorescently labeled ATP. The formation of the fluorescently labeled AA-AMP;synthetase-microsphere complexes can be read in a flow cytometer which allows each microsphere to be identified and the corresponding signal from the binding of fluorescently labeled AA-AMP to be read.

Aminoacyl-tRNA Synthetase Bead Arrays

In this example each aminoacyl-tRNA synthetase is immobilized to different bead type and the formation of amino acid-AMP-synthetase complexes is monitored. Aminoacyl-tRNA synthetases specific for each amino acid to be analyzed are immobilized to uniquely distinguishable beads. Thus, each unique bead type only substantially binds one amino acid, the one specific to the synthetase immobilized. The enzymes may be immobilized by adsorption, entrapment, or covalent attachment, for example. As described above, beads identified based on different ratios of orange and red fluorescence may be used. ATP is labeled with a different color fluorescent dye, for example, a green fluorescent dye. The synthetase bearing beads are mixed together and are mixed with the amino acid sample in reaction buffer along with the green fluorescent labeled ATP. Synthetases on the beads bind their cognate amino acids and the fluorescently labeled ATPs forming amino acid-AMP-green dye-synthetase-bead complexes. A washing step is optionally employed to remove fluorescent ATP that is not converted into amino acid-AMP-synthetase complexes. The green fluorescent dye emits at a different wavelength from the orange and red dyes, thus providing a third fluorescent signal that allows the amount of amino acids bound to the synthetase beads to be quantitated. Thus in each sample the amounts of multiple amino acids can be determined from the emission of a single fluorescent reporter molecule because the amino acid-specific ity of each bead classification in the bead array is known.

The amino acid-AMP-synthetase complexes may be detected using a flow cytometer, as described above for tRNA bead arrays. For example, the beads may be read in a FLOWMETRIX™ or LUMINIX® flow cytometry system (Luminex Corporation, Austin, Tex.: www.Luminexcorp.com). The FLOWMETRIX™ flow cymetry system may be configured for the Becton Dickinson (San Jose, Calif.) FACSCAN® flow cytometer based on a single 488-nm excitation laser. The flow cytometer analyzes individual microspheres by size and fluorescence, distinguishing three fluorescent colors, orange (585 nm), red (>650 nm) and green (530 nm). Using the LUMINIX® 100 analyzer, each bead set may be distinguished by a unique spectral address based on its 658 nm/712 nm emission ratio when excited by the 635 nm laser in the LUMINIX® 100 instrument. The LUMINIX® software uses this spectral profile to assign beads to their classification. Thus, multiple bead classifications can be combined in one sample, and the LUMINIX® software processes the signals to generate an array. In the LUMINIX® 100 analyzer, determination of the amounts of amino acid bound to each bead classification may be accomplished by coincident excitation of the beads with the 532 nm laser in the instrument. Thus, labeling bead bearing amino acid complexes with a green fluorescent reporter such as phycoerythrin (Molecular Probes, Eugene, Oreg.) which emits at 575 nm when excited at 532 nm, produces a third fluorescent signal that allows the amount of amino acids bound to the beads to be quantitated.

Microflow Bead Arrays

In another example of a bead array tRNAs or synthetases are immobilized onto uniquely distinguishable microbeads as described above. The microbeads (either synthetase or tRNA microbeads) are immobilized in a flow cell. The flow cell may be microfabricated on a glass surface, for example. The microbeads in solution are loaded into the flow cell through the inlet and pack against a support forming a packed planar array in each microchannel. Parallel microchannels are employed on the same microchip to permit simultaneous analysis of multiple amino acid samples. The bead array remains fixed as reagents and samples are pumped through each flow cell. Amino acid analysis is monitored optically by collecting and imaging fluorescent figures generated by the entire optical bead arrays onto a CCD detector followed by image processing. For example, with tRNA bead arrays, the amino acid samples along with the aminoacyl-tRNA synthetases and fluorescently labeled EF-Tu:GTP are pumped into the flow channels. Wash buffers may optionally be pumped through the flow channels. EF-Tu:GTP that is labeled with a green fluorescent dye binds AA-tRNAs on each bead type. After excitation with light at the appropriate wavelength(s) (e.g., 488 nm) each bead type is distinguished by its unique ratio of orange/red fluorescence and the amount of amino acid complexed to each bead is detected by the green fluorescence bound to each bead. The flow cell may be mounted on a fluorescence microscope fitted with a CCD camera.

Flow through chips can be made from glass or silicon, for example. In the case of fluorescence detection, excitation light is able to penetrate the chip substrate and excite the fluorescent reporter groups, and emission light is able to escape from within the chip. Optically conductive substrates with minimal autofluorescence are preferred. Glass has several advantages for use as a microarray substrate: a large body of research has been devoted to the immobilization of biomolecules onto glass substrates, glass has good tensile strength, and glass with low autofluorescence is available. The material is known as microchannel plate glass or glass capillary arrays and is commercially available from a number of vendors (e.g., Galileo Electro-Optics Corporation (Sturbridge, Mass.).

The use of CCD imaging rather than confocal scanning is preferred for detection. The microflow chip reader incorporates a microscope objective with matched microflow chip and CCD dimensions to achieve good lateral resolution. The light source is optimized to provide uniform illumination of all microflow channels. Detection is accomplished using a sensitive, CCD camera that images all microchannels at once.

Example 31

Example 31 describes a preferred method for the detection of one or more primary protein amino acids in a sample by biomolecular recognition wherein the coresponding aminoacyl-tRNA synthetases combine with the primary protein amino acid to yield a detectable product wherein said primary protein amino acids are selected from the group consisting essentially of arginine, alanine, cysteine, aspartic acid, glutamic acid, phenylalanine, glycine, histidine, isoleucine, lysine, leucine, methionine, asparagine, proline, glutamine, serine, threonine, valine, tryptophan, tyrosine. The detection of the primary amino acid may be qualitative and/or quantitative. It is important to note that the amino acids arginine, glutamic acid, and glutamine requires the presence of the cognate tRNA, or a fragment therof, to form the corresponding aminoacyl adenylate (AA-AMP).

This method is practiced by the steps of contacting said sample with an amount of the aminoacyl-tRNA synthetase specific to the primary protein amino acid sufficient to form a detectable product and then detecting the detectable product. The amount of the synthetase is determined by the activity of the synthetase enzyme used, the concentration of the substrates, and the desired length of the assay period. One of ordinary skill in the art would appreciate how to experimentally determine a suitable amount of enzyme. The detecting step is preferably accomplished by use of a spatial array, labeling, bonding assay, surface plasma resonance, or piezo electric based process as described above.

In a further embodiment of the method, a tRNA specific to the primary amino acid is contacted with the synthetase under reaction conditions sufficient to form the aminoacyl-tRNA and the aminoacyl tRNA product is detected.

Suitable reaction conditions for both synthetase reactions A and B include:
1. 30 mM HEPES-KOH, pH 7.6, 10 mM MgCl2, 50 mM KCl, 1 mM dithiothreitol, 1 mM ATP, 1–300 uM tRNA, 1 nM-300 uM aminoacyl-tRNA synthetase(s), inorganic pyrophosphatase (10 U/ml)23–37° C.
2. 50 mM Tris-HCl, pH 7.9, 10 mM MgCl2, 50 mM KCl, 2 mM dithiothreitol, 2 mM ATP.
3. 80 mM Tris-HCl, pH 7.8, 100 mM KCl, 10 mM MgCl2, 3 mM ATP, 35° C.
4. 100 uM tRNA, 150 mM Tris-HCl, pH 7.5, 75 mM KCl, 10 mM MgCl2, 5 mM ATP, 1 nM-300 uM aminoacyl-tRNA synthetase.

In a further embodiment of the method, an aminoacyl-tRNA is complexed with an elongation factor and the complex of the aminoacyl-tRNA with the elongation factor is determined. The complexing reaction buffer and conditions used to form the ternary complex will be according to the elongation factor used. Suitable reaction buffers and conditions are well known to those of skill in the art. The elongation factor preferably should be in molar excess over the aminoacyl tRNA formed. The amount therefore depends upon the amount of amino acid in a sample. Dynamic range finding methods which are well known to one of ordinary skill in the art can be used to empirically ascertain the optimum amounts of reactants, synthetase, and elongation factor in an assay.

A preferred elongation factor is EF-Tu:GTP from *Thermus thermophilus*. In this case, for instance, tRNA aminoacylation and binding to elongation factor:GTP complexes may be conducted at room temperature (25° C.) in a suitable buffer e.g., 20 mM imidazole-HCl (pH 7.5) 3 mM KCl, 0.5 mM DTE (1,4-dithioerythritol), 5 mM MgCl, 5 mM ATP, 1 mM GTP. NH$_4$Cl is used to stabilize the EF-Tu:GTP-AA-tRNA complex and binding buffers. However, NH$_4$Cl may also inhibit the synthetases(see Ribeiro et al. (1995) et al. supra.). Suitable wash buffers would therefore be:

50 mM Tris/HCl, pH 7.5; 50 mM NH$_4$Cl, 50 mM KCl, 10 mM MgCl$_2$, 1 mM GTP, and 5 mM beta-mercaptoethanol.

50 mM HEPES, pH 7.5, 150 mM NaCl, 50 mM NH$_4$Cl, 10 mM MgCl$_2$, 5 mM beta-mercaptoethanol, and 50 uM GTP.

Elution of AA-tRNA from Ef-Tu:GTP buffers would be:
100 mM sodium borate, pH 7.5, 1 M NaCl, 10 mM MgCl$_2$, beta-mercaptoethanol, 50 uM GTP or 50 mM HEPES, pH 7.5, 150 mM NaCl, 5 mM beta-mercaptoethanol, 50 mM NH$_4$Cl, 10 mM MgCl$_2$, and 1 mM GTP.

In a preferred embodiment one or both of the aminoacyl tRNA or the elongation factor is labeled with a flourescent label to facillitate detection of the ternary complex. Both tRNAs and EF-Tu:GTP have been fluorescently labeled and found to retain their binding specificities for one another. For example, see Johnson et al. (1982) *J. Mol. Biol.* 156:113–140; Watson et al. (1995) *Biochemistry* 34, 7904–7912 for methods and compositions of such labeling.

Optical detection methods are particularly apt when a flourescent label is used. In general, a fluorescent probe is captured on the microarray via formation of the ternary complex above, the unbound material is washed away and the fluorescence bound to each element in the captured portion is visualized by fluorescence detection. Confocal scanners and/or CCD cameras are preferably employed for detection in microarrays and may be used in the subject invention. However, miniaturized lasers or LEDs and miniaturized light detectors are well known to one of ordinary skill in the art and may be used in the subject invention.

The invention has many other possible embodiments and should not be construed as limited to the above described embodiments or examples as set forth herein. Rather, these embodiments and examples are provided so that the disclosure will be thorough and complete, and fully convey the scope of the invention to those skilled in the art. In particularly, the invention may be practiced with any number of the 20 protein primary amino acids, and wherein the number 20 has been described, it is not intended to limit the assay to only twenty amino acids or twenty samples thereof.

Example 32

Example 32 describes some useful tRNAs and tRNA analogs of the invention. tRNAs may be obtained to form high affinity AA-tRNA:elongation:GTP complexes using in vitro selection to elongation factor:GTP complexes (e.g., Frehan T W et al. (199) *JBC* 274:666–72.) RNAs, DNAs and proteins are now commonly subjected to engineering for optimal function in a particular assay. For example, a DNA aptamer can be "evolved" to as a t RNA. Certainly, RNAs can be evolved to behave as tRNAs although they are not formally a tRNA. Minihelix tRNAs that act as tRNAs have been described. (e.g., Musier-Forsyth K. et al. (1991) *Proc. Natl. Acad. Sci. USA* 88:209–13. The substitution of such tRNA functional analogs for naturally occurring tRNAs is contemplated in this invention wherever tRNAs are recited.

Example 33

Example 33 describes methods for in vivo amino acid analysis. The detection system is isolated from the more complicated sample environment by a dialysis membrane or microsieve to bar access of interfering high molecularweight substances from the detector. Minidialysis probes are well known in the art and microdialysis chambers and microchips for analysis have been described above. In conducting in vivo analyses, care should be taken to match the osmotic pressure on both sides of the membrane. (see Niwa O. et al. (1996) *Anal Chem.* 68:1865–1870. Miniature ultrafiltration probes have also been described (Schneiderheinze J, M. (1996) *Anal Chem.* 68:3758–3762).

Microdialysis offers a means of continuously sampling without major disturbances the free endogenous amino acids from any fluid compartment or organ of a living organism. For example, glutamate, asparatate, and glycine are neurotransmitters in addition to playing a role in cellular metabolism. It is desireable to measure the concentration of amino acids continuously or repeatedly in living organisms (e.g., neuron glutamate or glycine levels and cell culture systems). This can be achieved forany one up to all twenty of the primary amino acids using microdialysis probes and sensors as invented herein. For a review of microdialysis see Denoroy L. et al. 1998 *Electrophoresis* 19:2841–7. Integrated biochemical microsystems have also been described (e.g., see Leistiko O., and Jensen (1998) *J. Micromech. Microeng.* 8:148–50.

Example 34

In one aspect of the invention, the AA-RNA is bound to a biomolecule that specifically binds AA-RNAs and the AA RNA is detected. A wash step is usually employed to remove unbound or weakly bound material. The bound RNA is then detected using known methods of RNA detection including but not limited to, RT PCR and mass spectroscopy.

Example 35

Electrochemical biosensors are also contemplated for use in detectingamino acids according to the invention. Two broad categories of electrochemical biosensors may be distinguished depending on the nature of the biomolecular recognition process: biocatalytic devices and affinity sensors. Microfabrication technology allows use of easy to use sensor strips (see Wang J., (2000) *Analytical Electrochemistry* Wiley-VCH, NY). Thin film lithographic processes can also be used for producing small electrodes in silicon (Fiaccabrino and Kondelka (199*) *Electroanalysis* 10:217; Erickson K. and Wildig O. (1993) *Clin. Chem.* 39:383. Microfabricated electrodes can be integrated with other microstructures (E.g., micropumps, microchannels, microdialysis probes, mixing chambers, and valves) to produce complete miniaturized analytical systems (micro-total analytical systems, i.e., "Lab on a Chip"). Larger scale sensor fabrication can be accomplished through lithography or also screen printing processes (Wring S. and Hart S. (1992) Analyst 117:1281. Electrical biosensors with biomolecular recognition molecules immobilized on or retained at electrodes and methods for immoblization are well known in the art. See Aizawa M. et al. (1980) *Anal. Chim. Acta* 115:61; Skladal S. (1997) *Electroanalysis* 9:737; Kobos R. K. (1987) *Trends Anal Chem.* 6:6)

Miniaturized electrochemical sensor arrays are known. Microlithographic techniques are often used for construction of amperometric array electrodes. Electrode arrays are used in connection with computer assisted pattern-recognition algorithms. The development of sensor arrays are reviewed by Diamond, D. (1993) *Electroanalysis.* 5:795).

All references cited in this specification, including the background, the summary, and the detailed description of the invention, are herein incorporated by reference in their entireties and to the extent that there is no inconsistency with the present disclosure.

What is claimed is:

1. A method for specifically detecting a primary amino acid in a sample, said method comprising:
    contacting said primary amino acid to be detected with a plurality of aminoacyl tRNA synthetases, wherein each member synthetase of said plurality differs from other member synthetases of said plurality according to the cognate primary amino acids thereof and wherein said plurality of tRNA synthetases comprises an aminoacyl tRNA synthetase cognate to said primary amino acid to be detected, and
    wherein said contacting is under reaction conditions capable of forming a product with said primary amino acid to be detected, wherein said product is selected from the group consisting of the aminoacyl-tRNA synthetase:amino acid AMP complex of said primary amino acid to be detected, inorganic pyrophosphate, the aminoacyl-tRNA corresponding to said primary amino acid to be detected, and AMP; thereby forming said product; and
    specifically detecting said product.

2. The method of claim 1, wherein said detecting detects inorganic pyrophosphate.

3. The method of claim 1, wherein said detecting detects an aminoacyl tRNA synthetase:aminoacyl-adenosine monophosphate complex of said primary amino acid.

4. The method of claim 1, wherein the sample comprises a plurality of primary amino acids.

5. The method of claim 1, wherein said plurality of aminoacyl tRNA synthetase is immobilized on a solid support.

6. The method of claim 1, wherein said primary amino acid is phenylalanine.

7. The method of claim 1, wherein said primary amino acid is glycine.

8. The method of claim 1, wherein said primary amino acid is aspartic acid.

9. The method of claim 1, wherein said sample is a biological sample.

10. The method of claim 9, wherein said sample is a blood sample or a serum sample.

11. The method of claim 1, wherein said sample is a N-terminal or C-terminal digest of a polypeptide or protein.

12. The method of claim 1, wherein said sample is a hydrolysate of a protein.

13. The method of claim 1, wherein said contacting is with an aminoacyl tRNA synthetase for each of the 20 primary amino acids.

14. The method of claim 1, wherein said product is labeled and said detecting is by means of said label.

15. The method of claim 1, wherein said product is directly detected.

16. The method of claim 1, wherein said product is indirectly detected.

17. The method of claim 4, wherein said method said plurality of amino acids in said sample are each to be specifically detected, and
    wherein said plurality of amino acids to be specifically detected in said sample is contacted with said plurality of aminoacyl tRNA synthetases, wherein in said plurality of aminoacyl tRNA synthetases there is a member cognate to each member of said plurality of primary amino acids to be detected; and
    wherein said contacting is under reaction conditions capable of forming a plurality of said products; and
    wherein said plurality of said products forms and comprises a product for each member of said plurality of the primary amino acids to be specifically detected, and
    wherein said detecting separately detects each member of said plurality of said products, and
    whereby each member of said plurality of said primary amino acids to be detected in said sample is specifically detected.

18. The method of claim 17, wherein the detecting is quantitative and the amount of each primary amino acid of said plurality of primary amino acids to be detected in said sample is thereby determined.

19. The method of claim 17, wherein said members of said plurality of aminoacyl tRNA synthetases are spatially resolved.

20. The method of claim 17, wherein said members of said plurality of aminoacyl tRNA synthetases are immobilized on a solid support.

21. The method of claim 17, wherein each of said plurality of aminoacyl tRNA synthetases is located at a known locus of a spatial array, and wherein said detecting is according to said known locus.

22. The method of claim 21, wherein each member of said plurality of products is labeled and said detecting is by means of detecting said label.

23. The method of claim 17, wherein a spatial array is formed by separately locating each of said aminoacyl tRNA synthetases at a known locus of a solid support selected from the group consisting of microtiter surface, microwell, microchannel and microcapillary array.

24. The method of claim 1, wherein the detecting is quantitative and the amount of said primary amino acid in said sample is determined.

25. The method of claim 1, wherein said primary amino acid to be detected is contacted with its cognate tRNA and the product is the aminoacyl tRNA of the primary amino acid to be detected.

26. The method of claim 25, wherein said primary amino acid to be detected is contacted with a plurality of tRNAs,
   wherein each member tRNA of said plurality of tRNAs differs from other member tRNAs of said plurality of tRNAs according to the cognate primary amino acids thereof;
   wherein said plurality of tRNAs has a member cognate to said primary amino acid to be detected; and
   wherein each member tRNA of said plurality of tRNAs is located separate from other member tRNAs of said plurality of tRNAs at a known locus on a spatial array;
   and wherein said aminoacyl tRNA of the primary amino acid forms at the known locus of the tRNA cognate to the primary amino acid to be detected; and
   wherein said detecting specifically detects said formed aminoacyl tRNA of the primary amino acid to be detected according to the known locus of the tRNA cognate to the primary amino acid to be detected.

27. The method of claim 26, wherein each of said member tRNAs of said plurality of tRNAs are immobilized on a solid support and said product is thereby immobilized on said solid support.

28. The method of claim 26, wherein each of said member tRNAs of said plurality of tRNAs is fluorescently labeled and said label is used to detect said product.

29. The method of claim 25, further comprising contacting said aminoacyl tRNA with an elongation factor binary complex with GTP or a GTP analog to form a ternary complex and by detecting said ternary complex.

30. The method of claim 29, wherein said factor is elongation factor Tu or elongation factor 1A in a complex with GTP or a GTP analog.

31. The method of claim 30, wherein said GTP analog is a nonhydrolyzable analog of GTP.

32. The method of claim 29, wherein said elongation factor is labeled.

33. The method of claim 26, wherein said spatial array is located on a solid support.

34. The method of claim 33, wherein said solid support is selected from the group consisting of microtiter surface, microwell, microchannel, glass chip, and microcapillary array.

35. The method of claim 1, wherein said product has a label detectable with a fluorescence detector, a proximity scintillation surface, a spectrophotometer, a luminometer, a scintillation counter, a Raman spectrophotometer, a charge coupled device camera, or a gamma counter.

36. The method of claim 1, wherein a molecular sieve through which compounds of greater than about 6 kDa cannot pass separates said sample from said aminoacyl tRNA synthetase.

37. The method of claim 25, wherein the detecting is quantitative and the amount of said primary amino acid to be detected in said sample is determined.

38. The method of claim 31, further comprising contacting said ternary complex with a biorecognition element; and detecting the interaction of said ternary complex with said biorecognition element.

39. The method of claim 26, wherein each member tRNA of said plurality of tRNAs comprises a unique distinguishing label for detection.

40. The method of claim 38, wherein said biorecognition element is bound to a transducer selected from the group consisting of a piezoelectric crystal, a surface plasmon resonance system, an acoustic wave sensor device, a fluorescence detector or a proximity scintillation surface to form a biosensor, and said detecting of said ternary probe is by means of said biosensor.

41. The method of claim 38, wherein said biorecognition element is bound to a transducer to create an amino acid biosensor.

42. The method of claim 38, wherein the biorecognition element is a ternary complex probe immobilized on a transducer.

43. The method of claim 42, wherein the transducer is an optical fiber, an electrode, a piezoelectric crystal, a thermistor or a planar wave guide.

44. The method of claim 29, wherein said tRNA for said primary amino acid to be detected is labeled with a detectable tag.

45. The method of claim 44, wherein said detectable tag is a fluorophore, a chromophore, a nanoparticle, a metal, an enzyme, a liposome-based label, an electrogenic label, ferrocine, biotin or a radioisotope.

46. The method of claim 29, wherein said elongation factor is labeled with a detectable tag.

47. The method of claim 29, wherein said ternary complex is detected using a ternary complex probe.

48. The method of claim 47, wherein said ternary complex probe is an antibody or an antibody fragment specific for said ternary complex.

49. The method of claim 47, wherein said ternary complex probe is a nucleic acid.

50. The method of claim 26, wherein each said member tRNAs of said plurality of tRNAs is labeled with a fluorophore, a chromophore, a nanoparticle, a metal, an enzyme, a liposome-based label, an electrogenic label, ferrocine, biotin or a radioisotope; and said product is the labeled aminoacyl tRNA corresponding to the labeled tRNA of the primary amino acid to be detected.

51. The method of claim 50, wherein said labeled aminoacyl tRNA is detected by fluorescence, chromophore, radioactive decay, an electrical signal, mass spectrometry, or chemiluminescence.

52. The method of claim 38, wherein biorecognition elements are arrayed on a film or scintillator sheet.

53. The method of claim 30, wherein the formation of the ternary complex employs dual distinguishable fluorescent labels, wherein said elongation factor is labeled with one detectable label and said tRNA for said primary amino acid to be detected is labeled with a second detectable label.

54. The method of claim 53, wherein said first label is sulforhodamine 101 sulfonyl chloride and said second label is fluorescein, and after formation of said ternary complex, the ratio of bound fluorescein and sulforhodamine 101 sulfonyl chloride labels is determined using a dual-channel laser scanning confocal microscope as a detection system.

55. The method of claim 25, further comprising contacting said aminoacyl tRNA with an aptamer to form a ternary complex and detecting said ternary complex.

56. The method of claim 1, wherein said primary amino acid to be detected is alanine, asparagine, aspartic acid, cysteine, glycine, histidine, isoleucine, leucine, lysine, methionine, phenylalanine, proline, seine, threonine, tryptophan, tyrosine, valine, arginine, glutamic acid, glutamine or valine;

with the proviso that when the primary amino acid in the sample is arginine, glutamic acid, or glutamine the amino acyl tRNA synthetase cognate to the primary amino acid is prebound to the tRNA cognate to the primary amino acid.

57. The method of claim 17, wherein said members of said plurality of products is detected by mass spectrometry.

58. The method of claim 25, wherein said detecting comprises contacting the aminoacyl tRNA with a labeled probe that binds the aminoacyl-tRNA and detecting said labeled probe.

59. The method of claim 58, wherein the labeled probe is an elongation factor, an antibody, or an aptamer.

60. The method of claim 26, wherein the plurality of amino acid synthetases has members cognate for each of the 20 primary amino acids and the plurality of tRNAs has members cognate for each of the 20 primary amino acids; wherein the 20 primary amino acids are alanine, asparagine, aspartic acid, cysteine, glycine, histidine, isoleucine, leucine, lysine, methionine, phenylalanine, praline, serine, threonine, tryptophan, tyrosine, valine, arginine, glutamic acid, glutamine and valine.

61. A method for specifically detecting a primary amino acid in a sample, said method comprising:

contacting said primary amino acid with an aminoacyl tRNA synthetase cognate to the primary amino acid to form a product, and specifically detecting product, whereby said primary amino acid is specifically detected and wherein said sample is selected from the group consisting of cerebrospinal fluids, fermentation broths, proteolytic digests, cell culture media, blood, or serum.

62. A method for specifically detecting a primary amino acid in a sample, said method comprising:

contacting said primary amino acid with an aminoacyl tRNA synthetase and tRNA cognate to the primary amino acid to form a product to form an aminoacyl tRNA of the primary amino acid; and contacting said aminoacyl tRNA with an elongation factor binary complex with GTP or a GTP analog to form a ternary complex;

and detecting said ternary complex.

* * * * *